United States Patent
Van Der Boom et al.

(10) Patent No.: US 9,707,540 B2
(45) Date of Patent: Jul. 18, 2017

(54) METAL-ORGANIC MATERIALS AND METHOD FOR PREPARATION

(71) Applicant: YEDA RESEARCH AND DEVELOPMENT CO. LTD., Rehovot (IL)

(72) Inventors: Milko E. Van Der Boom, Rishon Lezion (IL); Michal Lahav, Rehovot (IL); Shira Hamami, Rehovot (IL); Maria-Chiara Di-Gregorio, Rehovot (IL); Qiang Wen, Rehovot (IL); Sreejith Shankar Pooppanal, Rehovot (IL)

(73) Assignee: YEDA RESEARCH AND DEVELOPMENT CO. LTD., Rehovot (IL)

( * ) Notice: Subject to any disclaimer, the term of this patent is extended or adjusted under 35 U.S.C. 154(b) by 0 days.

(21) Appl. No.: 15/079,903

(22) Filed: Mar. 24, 2016

(65) Prior Publication Data

US 2016/0271582 A1  Sep. 22, 2016

Related U.S. Application Data

(63) Continuation-in-part of application No. 14/904,708, filed as application No. PCT/IL2014/050635 on Jul. 13, 2014.

(60) Provisional application No. 61/846,021, filed on Jul. 14, 2013.

(51) Int. Cl.
C07D 213/06 (2006.01)
B01J 20/22 (2006.01)
C07D 213/42 (2006.01)

(52) U.S. Cl.
CPC ......... *B01J 20/226* (2013.01); *C07D 213/06* (2013.01); *C07D 213/42* (2013.01); *C07B 2200/13* (2013.01); *C07C 2103/74* (2013.01)

(58) Field of Classification Search
None
See application file for complete search history.

(56) References Cited

FOREIGN PATENT DOCUMENTS

WO  WO 2013/058844 A1  4/2013

OTHER PUBLICATIONS

Adisa et al. "Methane storage in molecular nanostructures", Nanoscale. Jun. 7, 2012;4(11):3295-307.
Ban et al. "Microporous and Mesoporous Materials", Microporous and Mesoporous Materials vol. 173, Jun. 2013, pp. 29-36.
Batten S.R. "Topology of interpenetration" CrystEngComm. 2001;3(18):67-72.
Batten et al. "3D networks constructed using both coordinative and hydrogen bonding: synthesis, structure and magnetic properties of M (tcm) 2 (H2O) 2• Me4pyz, M⊕=⊕ Co, Ni" CrystEngComm. 2001;3(8):33-5.
Biradha et al. "Coordination Polymers Versus Metal-Organic Frameworks", Cryst. Growth Des., 2009, 9 (7), pp. 2969-2970.
Boterashvili et al. "Integrated and Segregated Au/γ-Fe2O3 Binary Nanoparticle Assemblies". Angewandte Chemie International Edition. Dec. 3, 2012;51(49):12268-71.
Bridgeman, JA, "On the origin of paramagnetism in planar nickel(II) complexes", Dalton Trans. Apr. 21, 2008;(15):1989-92.
Burlakov et al. "Reversing Ostwald Ripening" arXiv preprint arXiv:1412,6280. Dec. 19, 2014.
Caragheorgheopol et al. "Mechanistic aspects of ligand exchange in Au nanoparticles" Physical Chemistry Chemical Physics, 2008;10(33):5029-41.
Carne-Sanchez et al. "Metal-organic frameworks: from molecules/metal ions to crystals to superstructures", Chemistry. Apr. 25, 2014;20(18):5192-201.
Chen et al. "Metal-organic frameworks with functional pores for recognition of small molecules", Acc Chem Res. Aug. 17, 2010;43(8):1115-24.
Cho et al. "Growth-controlled formation of porous coordination polymer particles", J Am Chem Soc. Dec. 17, 2008;130(50):16943-6.
Choudhury et al. "Linear vs exponential formation of molecular-based assemblies", J Am Chem Soc. Jul. 14, 2010;132(27):9295-7.
Cockroft et al. "Electrostatic control of aromatic stacking interactions" Journal of the American Chemical Society. Jun. 22, 2005;127(24):8594-5.
Cook et al. "Metal-organic frameworks and self-assembled supramolecular coordination complexes: comparing and contrasting the design, synthesis, and functionality of metal-organic materials", Chem Rev. Jan. 9, 2013;113(1):734-77.
Eddaoudi et al. "Systematic design of pore size and functionality in isoreticular MOFs and their application in methane storage" Science. Jan. 18, 2002;295(5554):469-72.
Evans et al. "Crystal engineering of NLO materials based on metal-organic coordination networks", Acc Chem Res. Jul. 2002;35(7):511-22.

(Continued)

*Primary Examiner* — Heidi Reese
(74) *Attorney, Agent, or Firm* — Mark S. Cohen; Pearl Cohen Zedek Latzer Baratz LLP

(57) ABSTRACT

The present invention provides metal-organic materials, more specifically organometallic polymers, comprising polypyridyl organic ligands such as tetrakis(4-(pyridin-4-ylethynyl)phenyl)methane, tetrakis(4-(2-(pyridin-4-yl)vinyl)phenyl)methane, 1,3,5,7-tetrakis(4-(pyridin-4-ylethynyl)phenyl)adamantane or 1,3,5,7-tetrakis(4-(2-(pyridine-4-yl)vinyl)phenyl) adamantine, and metal ions structurally coordinated with said ligands, and having three-dimensional crystalline micro or sub-micro structure; as well as a method for the preparation thereof. These metal-organic materials are useful as adsorbents in processes for gas adsorption or separation.

24 Claims, 48 Drawing Sheets

(56) References Cited

OTHER PUBLICATIONS

Fenske et al. "Advances in switchable supramolecular nanoassemblies" Chemistry—A European Journal, Jan. 16, 2012;18(3):738-55.

Férey et al. "A chromium terephthalate-based solid with unusually large pore volumes and surface area" Science. Sep. 23, 2005;309(5743):2040-2.

Fujita et al. "Preparation, clathration ability, and catalysis of a two-dimensional square network material composed of cadmium (II) and 4, 4'-bipyridine" Journal of the American Chemical Society. Feb. 1994;116(3):1151-2.

Furukawa et al. "The chemistry and applications of metal-organic frameworks", Science. Aug. 30, 2013;341(6149):1230444.

Furukawa et al. "Ultrahigh porosity in metal-organic frameworks" Science. Jul. 23, 2010;329(5990):424-8.

Gao et al. "Growing crystalline zinc-1,3,5-benzenetricarboxylate metal-organic frameworks in different surfactants", Inorg Chem. Jan. 21, 2014;53(2):691-3.

Gu et al. "Size-dependent deformation of nanocrystalline Pt nanopillars", Nano Lett. Dec. 12, 2012;12(12):6385-92; including supporting information.

Guo et al. "Effect of cationic surfactants on structure and morphology of mesostructured MOFs", RSC Adv., 2012,2, 5424-5429.

Hasenknopf et al. "Self-assembly of a heteroduplex helicate from two different ligand strands and Cu(II) cations", Proc Natl Acad Sci U S A. Feb. 20, 1996;93(4):1397-400.

Hu, Moqing "Design, synthesis and Applications of Metal Organic Framework", A Thesis Submitted to the Faculty of the Department of Chemistry and Biochemistry Worcester Polytechnic Institute, 2011, pp. 1-80.

Hu et al. "Chemical bonding approach for fabrication of hybrid magnetic metal-organic framework-5: high efficient adsorbents for magnetic enrichment of trace analytes" Analytical chemistry. Jun. 28, 2013;85(14):6885-93.

Hunter et al. "The nature of. pi-. pi. Interactions" Journal of the American Chemical Society, Jul. 1990;112(14):5525-34.

International Search Report for PCT Application No. PCT/IL2014/050635 dated Sep. 14, 2014.

Islam et al. "Synthesis, Characterization, and Antimicrobial Activity Studies of Ni (II) Complex with Pyridine as a Ligand" Journal of Chemistry. Apr. 6, 2015;2015.

Jeon et al. "Tröger's-base-derived infinite co-ordination polymer microparticles", Small. Jan. 2009;5(1):46-50.

Jiang et al. "Porous metal-organic frameworks as platforms for functional applications" Chemical Communications. 2011;47(12):3351-70.

Jung et al. "Monitoring shape transformation from nanowires to nanocubes and size-controlled formation of coordination polymer particles", Angew Chem Int Ed Engl. 2008;47(11):2049-51.

Jung et al. "Bio-functionalization of metal-organc frameworks by covalent protein conjugation" Chemical Communications. Feb. 21, 2011;47(10):2904-6.

Kaminker et al. "Stepwise assembly of coordination-based metal-organic networks", J Am Chem Soc. Oct. 20, 2010;132(41):14554-61.

Kaminker et al. "Coordination-polymer nanotubes and spheres: a ligand-structure effect", Angew Chem Int Ed Engl. Mar. 28, 2011;50(14):3224-6; including Supplement—Supporting Information, pp. S1-S5.

Kitagawa et al. "Functional porous coordination polymers", Angew Chem Int Ed Engl. Apr. 26, 2004;43(18):2334-75.

Kondo et al. "Rational Synthesis of Stable Channel-Like Cavities with Methane Gas Adsorption Properties: [{Cu2(pzdc)2(L)}n] (pzdc=pyrazine-2,3-dicarboxylate; L=a Pillar Ligand)", Angewandte vol. 38, Issue 1-2 Jan. 15, 1999 pp. 140-143.

Kramer et al. "Self-recognition in helicate self-assembly: spontaneous formation of helical metal complexes from mixtures of ligands and metal ions" Proceedings of the National Academy of Sciences. Jun. 15, 1993:90(12):5394-8.

Kreno et al. "Metal-organic framework materials as chemical sensors" Chemical reviews. Nov. 9, 2011;112(2):1105-25.

Langford et al. "Scherrer after sixty years: a survey and some new results in the determination of crystallite size" Journal of Applied Crystallography. Apr. 1, 1978:11(2)102-13.

Le Fur et al. "Excavations in molecular crystals. Chemical Communications" 2003(24):2966-7.

Lei et al. "Synthesis, Characterization, and Oxygen Sensing Properties of Functionalized Mesoporous SBA-15 and MCM-41 with a Covalently Linked Ruthenium(II) Complex", J. Phys. Chem. C, 2007, 111 (30), pp. 11291-11301.

Li et al. "Pyrite nanocrystals: shape-controlled synthesis and tunable optical properties viareversible self-assembly", J. Mater. Chem., 2011,21, 17946-17952.

Li et al. "Metal-organic frameworks for separations" Chemical reviews. Oct. 6, 2011;112(4869-932.

Li et al. "Nanoscale 1, 3, 5, 7-tetrasubstituted adamantanes and p-substituted tetraphenyl-methanes for AFM applications". Organic letters. Oct. 17, 2002;4(21):3631-4.

Liu et al. "Hierarchically Nanostructured Coordination Polymer: Facile and Rapid Fabrication and Tunable Morphologies", Cryst. Growth Des., 2010, 10 (2), pp. 790-797.

Long et al. "The pervasive chemistry of metal-organic frameworks", Chem. Soc. Rev., 2009,38, 1213-1214.

Lu et al. "Shape controlled synthesis of superhydrophobic zinc coordination polymersparticles and their calcination to superhydrophobic ZnO", J. Mater. Chem., 2011,21, 8633-8639.

Lu et al. "Tuning the structure and function of metal-organic frameworks via linker design", Chem Soc Rev. Aug. 21, 2014;43(16):5561-93.

Maia et al. "GPU linear algebra libraries and GPGPU programming for accelerating MOPAC semiempirical quantum chemistry calculations" Journal of chemical theory and computation. Aug. 13, 2012;8(9):3072-81.

Mason et al. "Evaluating metal-organic frameworks for natural gas storage", Chemical Science; Journal vol. 5; Journal Issue: 1, Jan. 1, 2014, pp. 32-51.

Masoomi, M.Y. "Morphological study and potential applications of nano metal-organic coordination polymers", Morsali, A., RSC Adv., 2013, 3, 19191-19218.

Miller et al. "Infrared spectra and characteristic frequencies of inorganic ions" Analytical chemistry. Aug. 1952;24(8):1253-94.

Murashima et al. "Preparations, Crystal Structures, and Magnetic Properties of N, N-Dipyridylaminoxyl as a New Magnetic Coupler and Its One-Dimensional Cobalt (II) Chains" Inorganic chemistry. Apr. 10, 2012;51(9):4982-93.

Murray et al. "Colloidal synthesis of nanocrystals and nanocrystal superlattices", IBM Journal of Research and Development 45.1 (Jan. 2001): 47-56.

Ni et al. "Rapid production of metal-organic frameworks via microwave-assisted solvothermal synthesis", J Am Chem Soc. Sep. 27, 2006;128(38):12394-5.

Noorduin et al. "Rationally designed complex, hierarchical microarchitectures", Science. May 17, 2013;340(6134):832-7.

Northrop et al. "Coordination-driven self-assembly of functionalized supramolecular metallacycles" Chemical Communications. 2008(45):5896-908.

Nose et al. "Influence of the d Orbital Occupation on the Structures and Sequential Binding Energies of Pyridine to the Late First-Row Divalent Transition Metal Cations: A DFT Study" The Journal of Physical Chemistry A. May 19, 2014;118(37):8129-40.

Oh et al. "Chemically tailorable colloidal particles from infinite coordination polymers", Nature. Dec. 1, 2015;438(7068):651-4.

Oh et al. "Ion exchange as a way of controlling the chemical compositions of nano- and microparticles made from infinite coordination polymers", Angew Chem Int Ed Engl. Aug. 18, 2006;45(33):5492-4.

Park et al. "Self-supported organometallic rhodium quinonoid nanocatalysts for stereoselective polymerization of phenylacetylene", J Am Chem Soc. Jul. 12, 2006;128(27):8740-1.

Pevzner et al. "Confinement-guided shaping of semiconductor nanowires and nanoribbons: "writing with nanowires"", Nano Lett. Jan. 11, 2012;12(1):7-12.

(56) References Cited

OTHER PUBLICATIONS

Plietzsch et al. "Four-fold click reactions: Generation of tetrahedral methane-and adarnantane-based building blocks for higher-order molecular assemblies" Organic & biomolecular chemistry. 2009;7(22):4734-43.
Que et al. "Proton magnetic resonance study of the stereochemistry of four-coordinate nickel (II) complexes. Dihalobis (tertiary phosphine) nickel (II) complexes" Inorganic Chemistry. Jan. 1973;12(1):156-63.
Ranft et al. "Additive-mediated size control of MOF nanoparticles", CrystEngComm, 2013,15, 9296-9300.
Reichert et al. "Expanded tetrahedral molecules from 1, 3, 5, 7-tetraphenyladamantane" Macromolecules. Nov. 1994:27(24):7015-23.
Rieter et al. "Nanoscale metal-organic frameworks as potential multimodal contrast enhancing agents", J Am Chem Soc. Jul. 19, 2006;128(28):9024-5.
Roberts et al. "The relationship between Young's modulus of elasticity of organic solids and their molecular structure", Powder Technology vol. 65, Issues 1-3, Mar. 1991, pp. 139-146.
Rosenthal et al. "Pyridine Complexes of Nickel (II). Inorganic Chemistry" Jun. 1965:4(6):840-4.
Rowsell et al. "Strategies for hydrogen storage in metal-organic frameworks", Angew Chem Int Ed Engl. Jul. 25, 2005;44(30):4670-9.
Sader et al. "Calibration of rectangular atomic force microscope cantilevers", Rev. Sci. Instrum. 70, 3967 (1999).
Sanner M.F. "Python: a programming language for software integration and development" J Mol Graph Model. Feb. 1, 1999;17(1):57-61.
Schilling et al. "Fourfold Suzuki-Miyaura and Sonogashira Cross-Coupling Reactions on Tetrahedral Methane and Adamantane Derivatives", European Journal of Organic Chemistry vol. 2011, Issue 9, pp. 1743-1754, Mar. 2011.
Seo et al. "A homochiral metal-organic porous material for enantioselective separation and catalysis", Nature. Apr. 27, 2000;404(6781):982-6.
Seoane et al. "Multi-scale crystal engineering of metal organic frameworks" Coord. Chem. Rev. 2016, 307, 147-187.
Shankar et al. "Homogeneously Micro-structured Metal-Organic Coordination Polymers", 4th National Graduate Student, Symposium in Organic Chemistry, Sep. 10, 2012, 2 pages.
Shankar et al. "Metal-Organic Microstructures: From Rectangular to Stellated and Interpenetrating Polyhedra" Journal of the American Chemical Society. Dec. 26, 2014;137(1):226-31.
Sheldrick G.M. "Crystal structure refinement with SHELXL" Acta Crystallographica Section C: Structural Chemistry. Jan. 1, 2015;71(1):3-8.
Shi et al. "Facile synthesis of shape and size tunable porphyrinoid coordination polymers: from copper porphyrin nanoplates to microspindles", Chem Commun (Camb). May 7, 2011;47(17):5055-7.
Shirman et al. "Halogen-Bonded Supramolecular Assemblies Based on Phenylethynyl Pyridine Derivatives: Driving Crystal Packing through Systematic Chemical Modifications", Cryst. Growth Des., 2008, 8 (8), pp. 3066-3072.
Sindoro et al. "Colloidal-sized metal-organic frameworks: synthesis and applications", Acc Chem Res. Feb. 18, 2014;47(2):459-69.
Sindoro et al. "Shape-selected colloidal MOF crystals for aqueous use" Chemical Communications. 2013;49(83):9576-8.
Smulders et al. "Building on architectural principles for three-dimensional metallosupramolecular construction", Chem Soc Rev. Feb. 21, 2013;42(4):1728-54.
Spokoyny et al. "Infinite coordination polymer nano- and microparticle structures", Chem Soc Rev. May 2009;38(5):1218-27.
Stewart J.J. "Optimization of parameters for semiempirical methods V: modification of NDDO approximations and application to 70 elements" Journal of Molecular modeling. Dec. 1, 2007;13(12):1173-213.
Stock et al. "Synthesis of metal-organic frameworks (MOFs): routes to various MOF topologies, morphologies, and composites", Chem Rev. Feb. 8, 2012;112(2):933-69.
Sun et al. "Coordination-induced formation of submicrometer-scale, monodisperse, spherical colloids of organic-inorganic hybrid materials at room temperature", J Am Chem Soc. Sep. 28, 2005;127(38):13102-3.
Supplementary European Search Report for European Application No. 14825682.9 dated Jan. 26, 2017.
Tabellion et al. "Discrete supramolecular architecture vs crystal engineering: the rational design of a platinum-based bimetallic assembly with a chairlike structure and its infinite, copper analogue", J Am Chem Soc. Aug. 8, 2001;123(31):7740-1.
Tabor et al. "Surface forces and surface interactions", Journal of Colloid and Interface Science vol. 58, Issue 1, Jan. 1977, pp. 2-13.
Tao et al. "Shape Control of Colloidal Metal Nanocrystals", Small vol. 4, Issue 3 Mar. 3, 2008, pp. 310-325.
Thompson et al. "Molybdenum complexes of two new pyridyl-based tetranucleating bridging ligands with unusual geometries: one with a tetrahedral donor set, and one containing two orthogonal non-interacting components", Inorganica Chimica Acta vol. 256, Issue 2, 31 Mar. 1997, pp. 331-334.
Toma et al. "The coordination chemistry at gold nanoparticles" Journal of the Brazilian Chemical Society. 2010;21(7):1158-76.
Tomasik, P., Ratajewicz, Z., Newkome, G.R., Strekowski, L.E., In Chemistry of Heterocyclic Compounds: Pyridine Metal Complexes (Part 6, vol. 14). (John Wiley & Sons, Inc., 2008).
Tuxen et al. "Size-dependent dissociation of carbon monoxide on cobalt nanoparticles", J Am Chem Soc. Feb. 13, 2013;135(6):2273-8.
Vasylyev et al. "Inorganic-organic hybrid materials based on keggin type polyoxometalates and organic polyammonium cations" Journal of molecular structure. Aug. 31, 2003;656(1):27-35.
Voorhees P.W. "The theory of Ostwald ripening" Journal of Statistical Physics. Jan. 1, 1985;38(1-2):231-52.
Wang et al. "Facile synthesis of size-tunable micro-octahedra via metal-organic coordination", Chem Commun (Camb). Sep. 28, 2009;(36):5457-9.
Wang et al. "Metal-organic frameworks as a tunable platform for designing functional molecular materials", J Am Chem Soc. Sep. 11, 2013;135(36):13222-34.
Wang et al. "Colossal cages in zeolitic imidazolate frameworks as selective carbon dioxide reservoirs" Nature. May 8, 2008;453(7192):207-11.
Wei et al. "Nucleobase-Metal Hybrid Materials: Preparation of Submicrometer-Scale, Spherical Colloidal Particles of Adenine-Gold(III) via a Supramolecular Hierarchical Self-Assembly Approach", Chem. Mater., 2007, 19 (12), pp. 2987-2993.
Whitesides et al. "Self-assembly at all scales", Science. Mar. 29, 2002;295(5564):2418-21.
Whitesides et al. "Molecular self-assembly and nanochemistry: a chemical strategy for the synthesis of nanostructures" Science. Nov. 29, 1991;254(5036):1312-9.
"With correlation to spectra from AIST: Integrated Spectral Database System of Organic Compounds" (Data were obtained from the National Institute of Advanced Industrial Science and Technology (Japan)) http://sdbs.db.aist.go.jp/sdbs/cgi-bin/direct_frame_top.cgi.
Yaghi et al. "Reticular synthesis and the design of new materials", Nature. Jun. 12, 2003;423(6941):705-14.
Zhang et al. "Metal-ion-coated graphitic nanotubes: controlled self-assembly of a pyridyl-appended gemini-shaped hexabenzocoronene amphiphile", Angew Chem Int Ed Engl. 2009;48(26):4747-50.
Zhao et al. "Hysteretic adsorption and desorption of hydrogen by nanoporous metal-organic frameworks", Science. Nov. 5, 2004;306(5698):1012-5.
Zhao et al. "Two Dawson-templated three-dimensional metal-organic frameworks based on oxalate-bridged binuclear cobalt(II)/Nickel(II) SBUs and Bpy linkers", Inorg Chem. Aug. 18, 2008;47(16):7133-8.

(56) References Cited

OTHER PUBLICATIONS

Zhao et al. "Tuning the topology and functionality of metal-organic frameworks by ligand design", Acc Chem Res. Feb. 15, 2011;44(2):123-33.

Zhuang et al. "Introduction of cavities up to 4 nm into a hierarchically-assembled metal-organic framework using an angular, tetratopic ligand" Chemical Communications. 2010;46(29):5223-5.

Fig. 2A
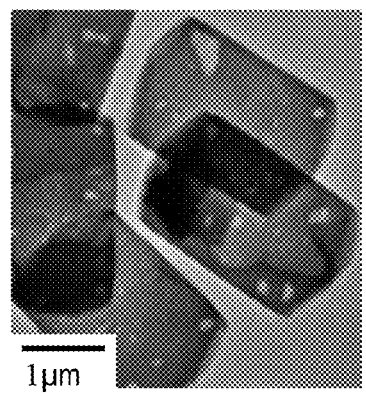
Fig. 2B
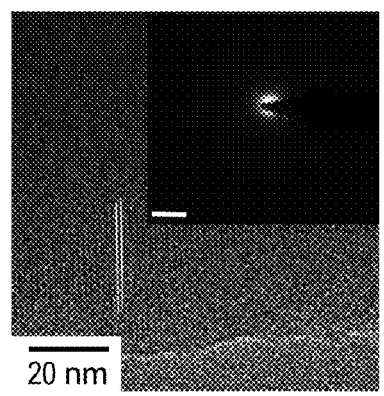
Fig. 3A
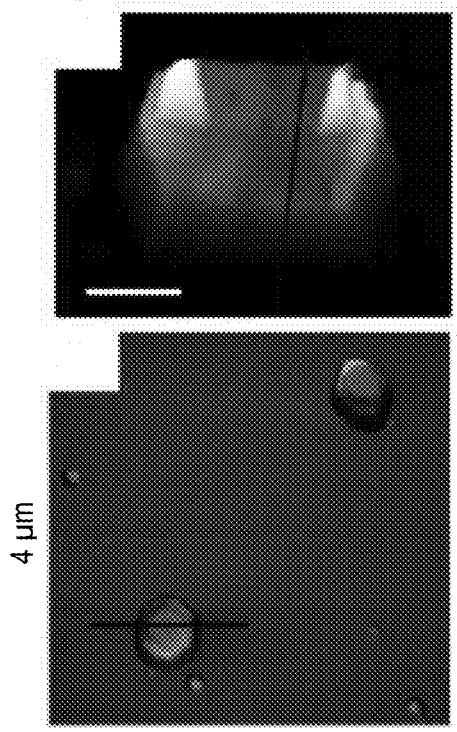
Fig. 3C
Fig. 3B
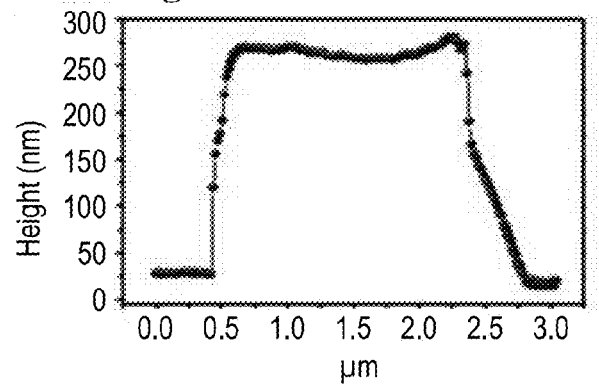
Fig. 3D
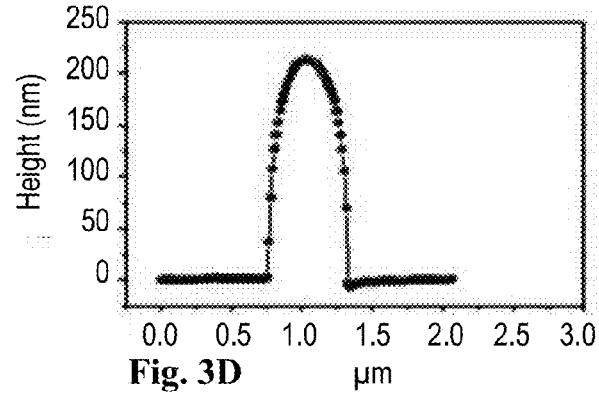

Fig. 10
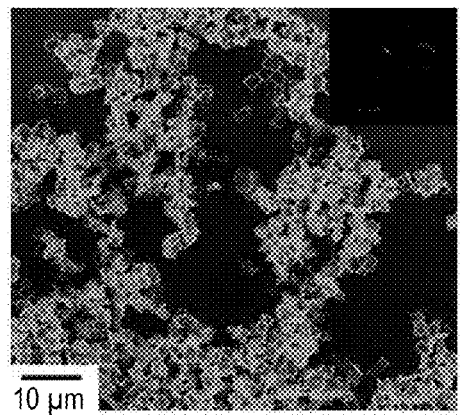
Fig. 11: panel A, panel B and panel C
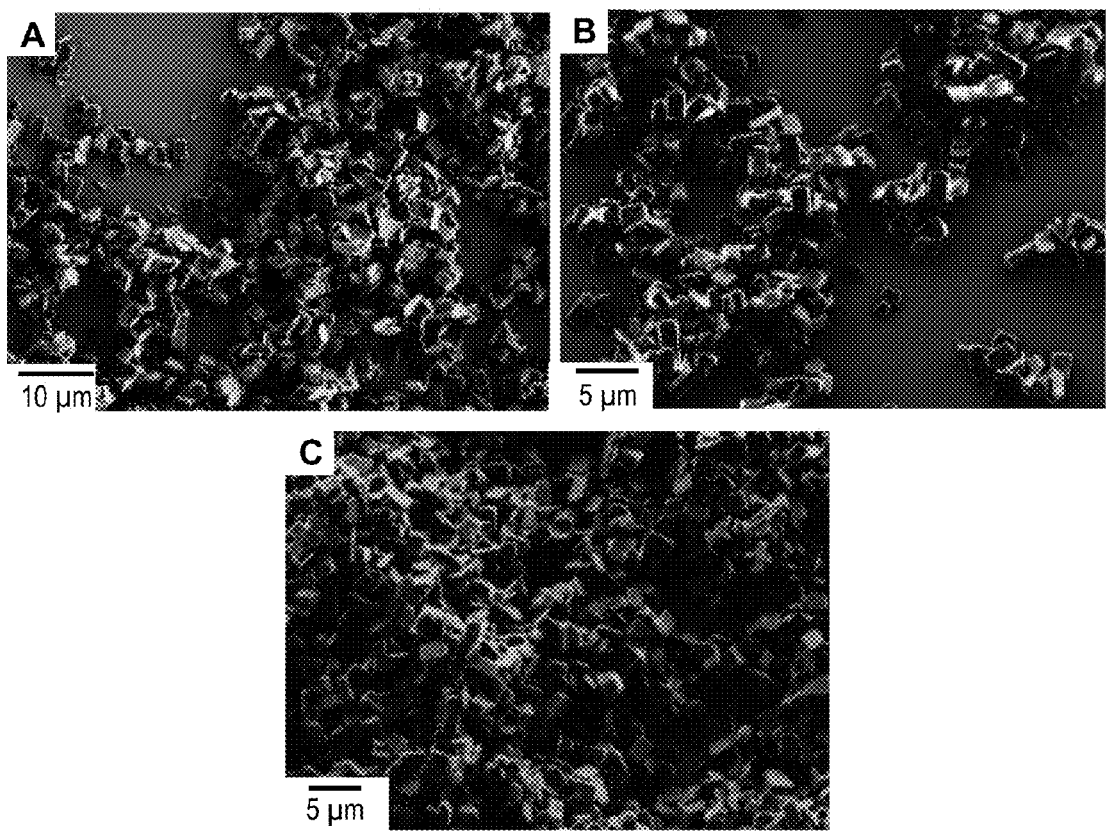

Fig. 12: panel A and panel B
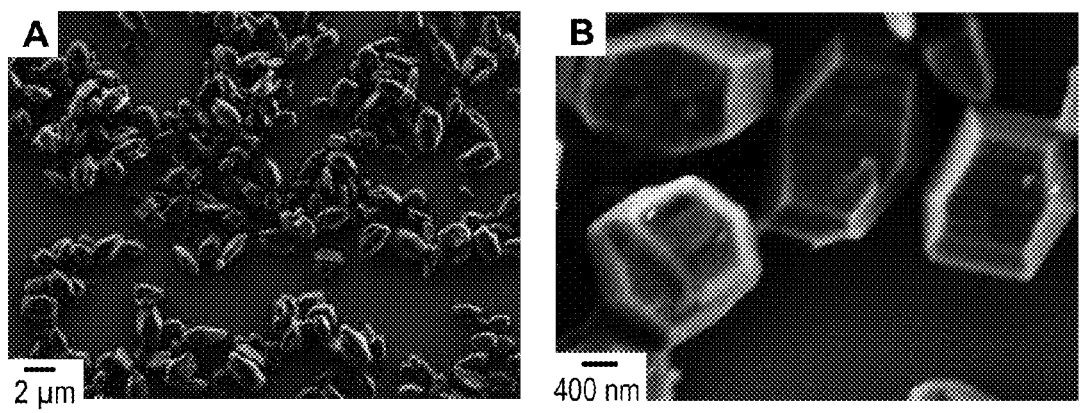
Fig. 13: panel A, panel B, panel C and panel D
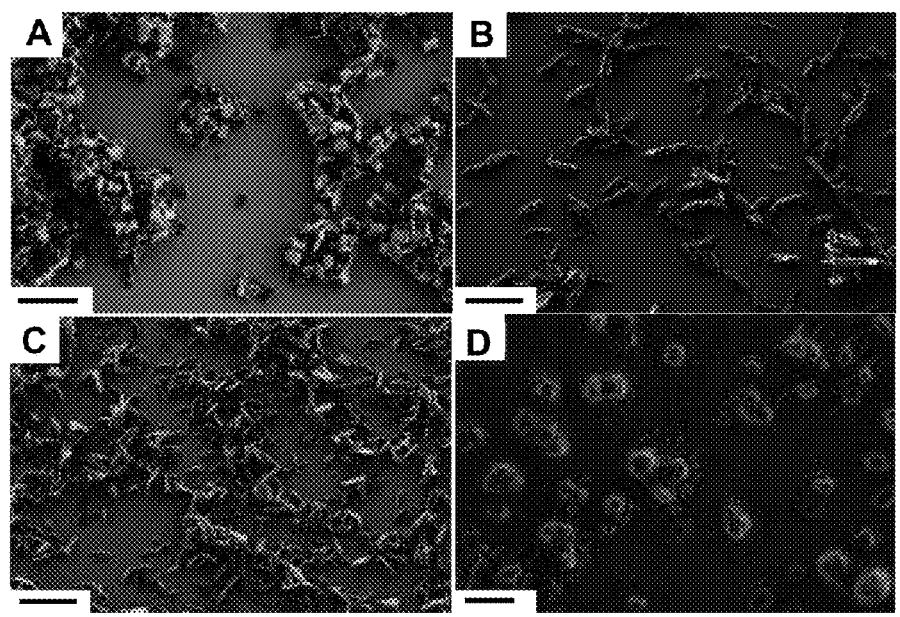

Fig. 14: panel A, panel B, panel C and panel D
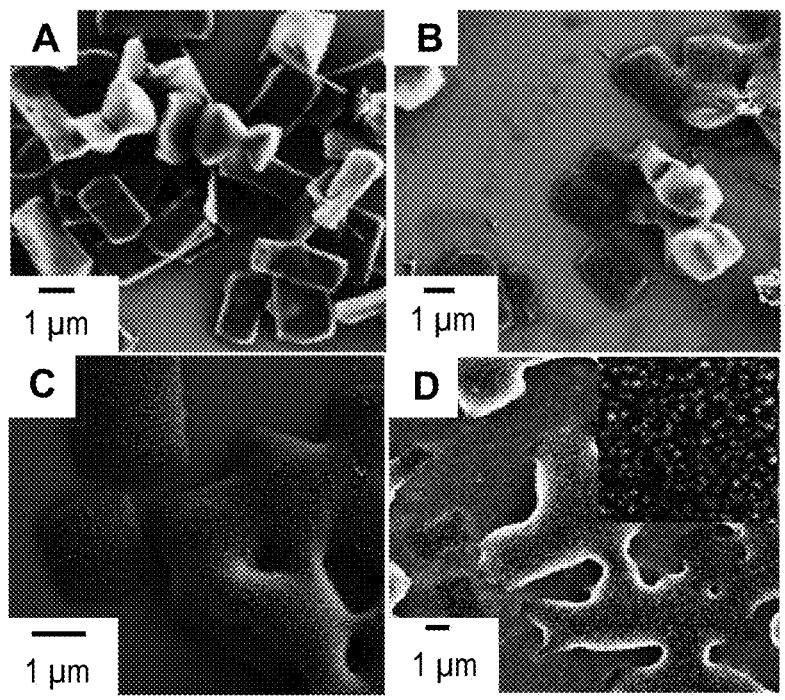
Fig. 15: panel A, panel B, panel C and panel D
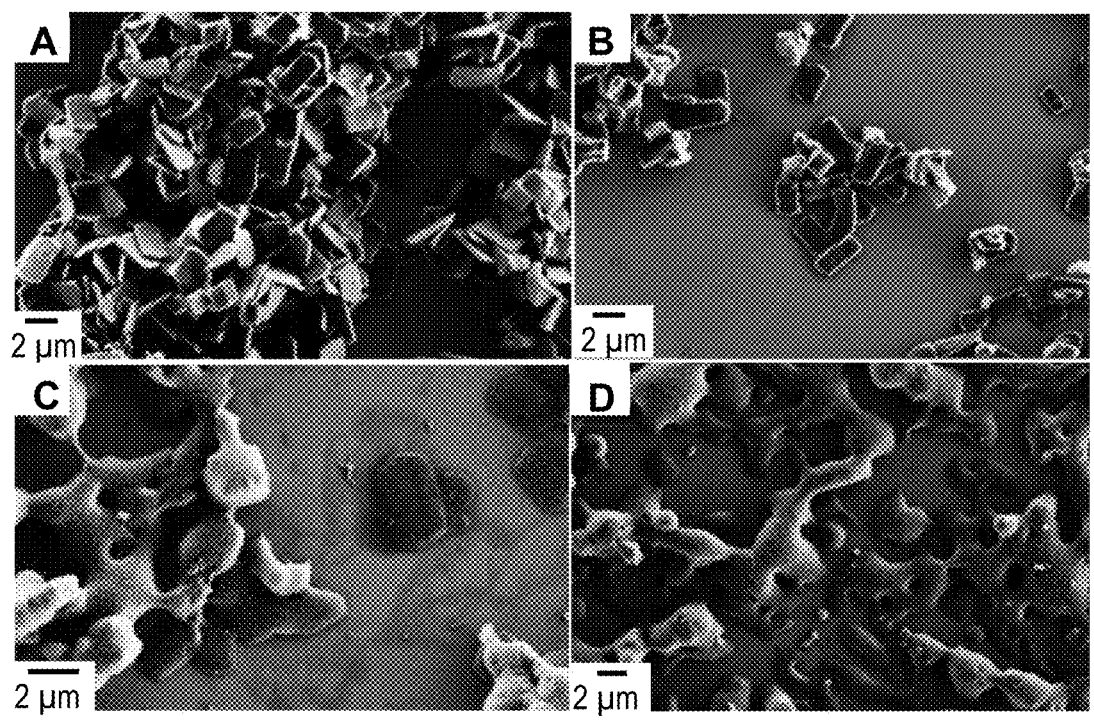

Fig. 16: panel A, panel B, panel C and panel D
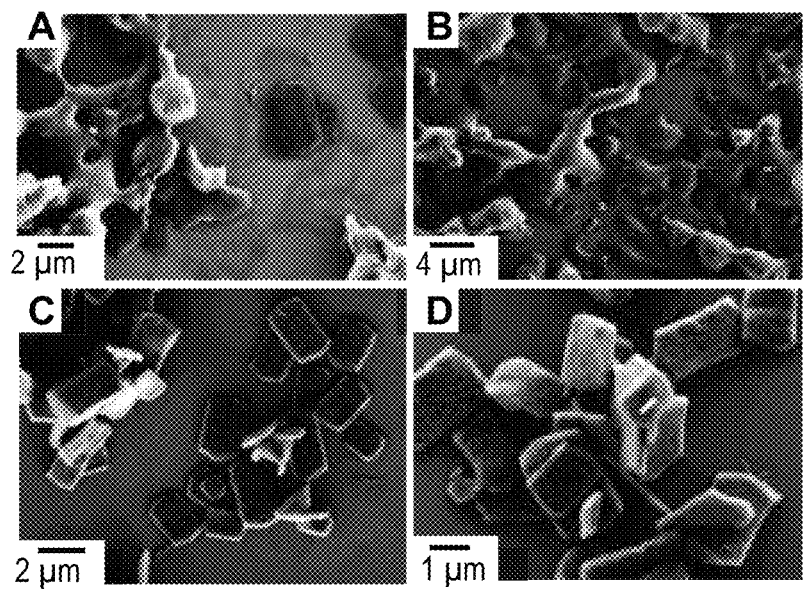
Fig. 17
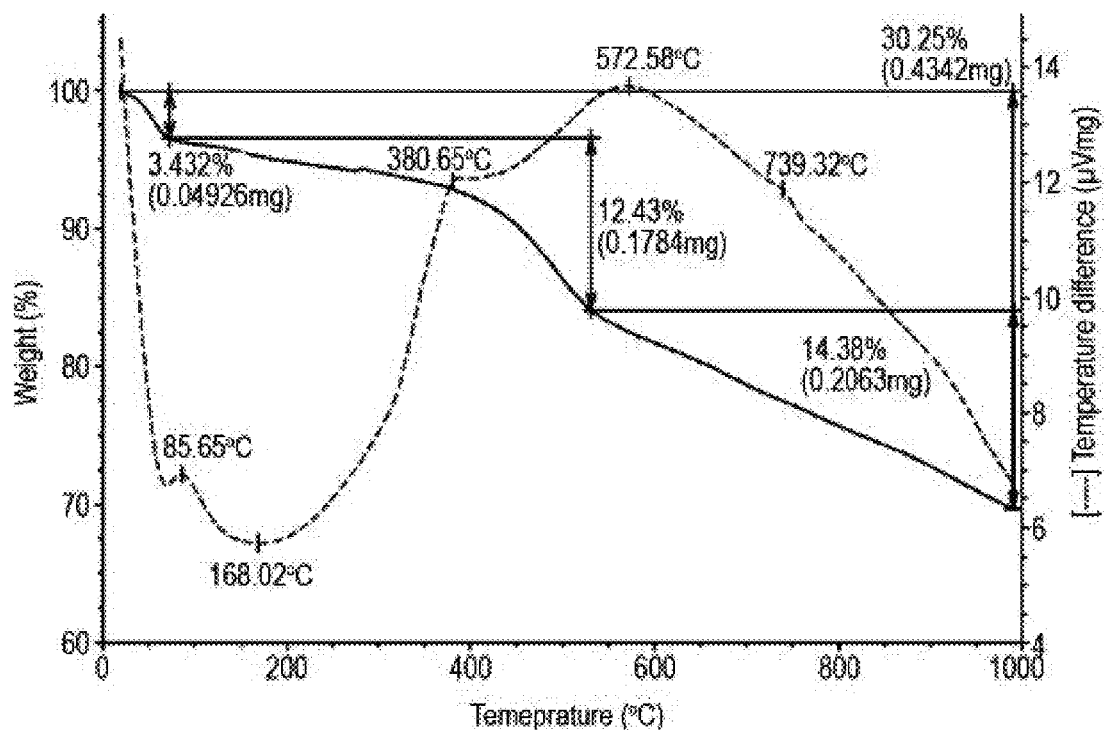

Fig. 23: panel A, panel B and panel C
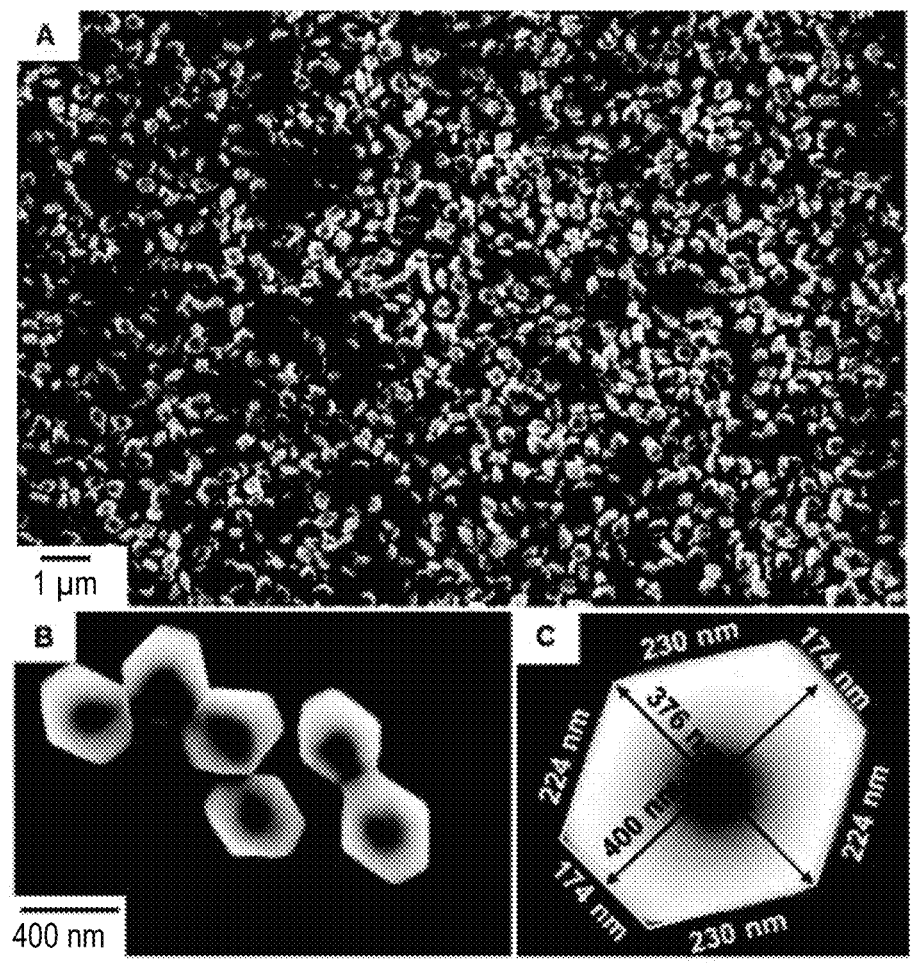

Fig. 24: panel A, panel B, panel C, panel D, panel E and panel F
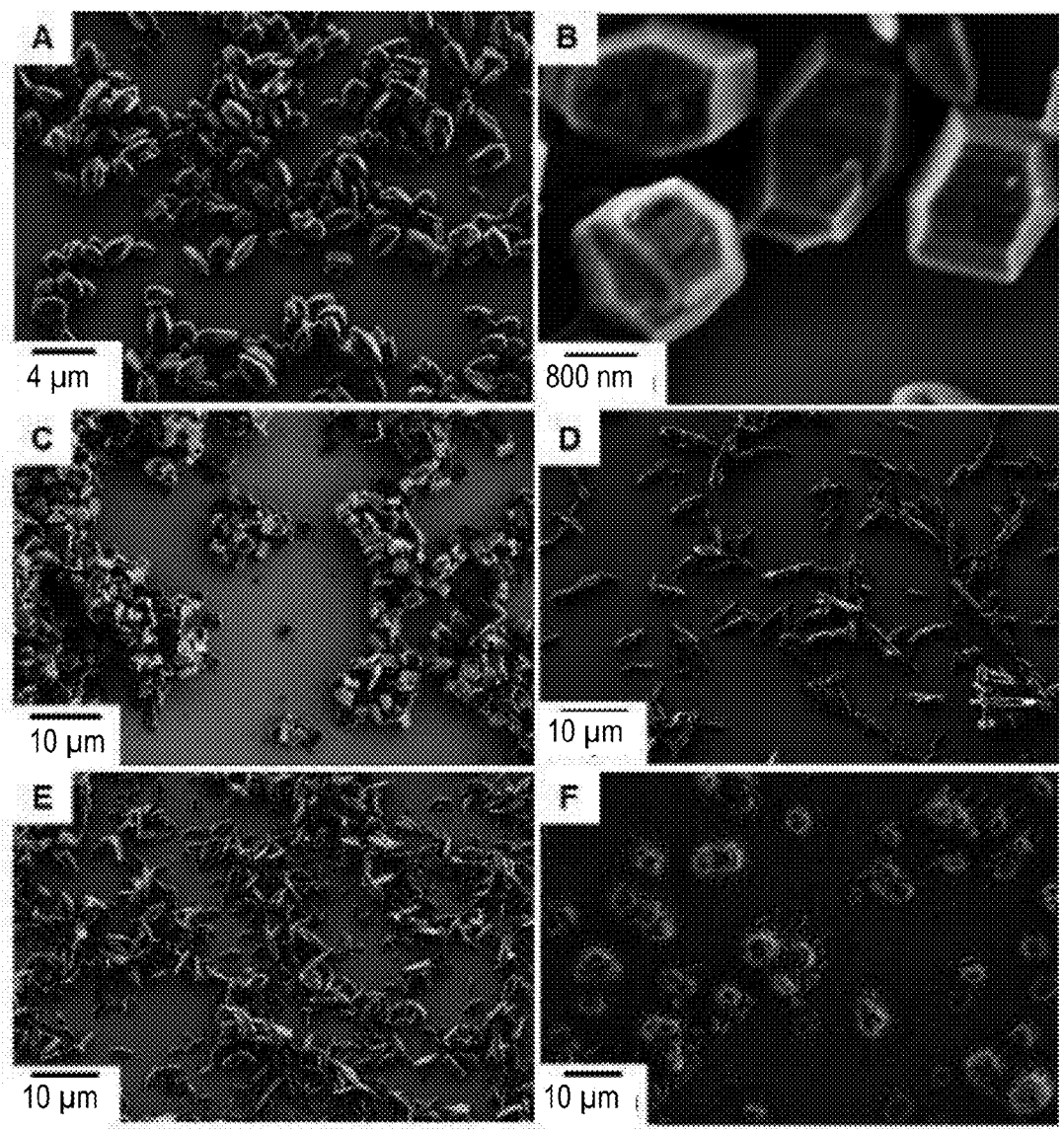

Fig. 25: panel A, panel B, panel C and panel D
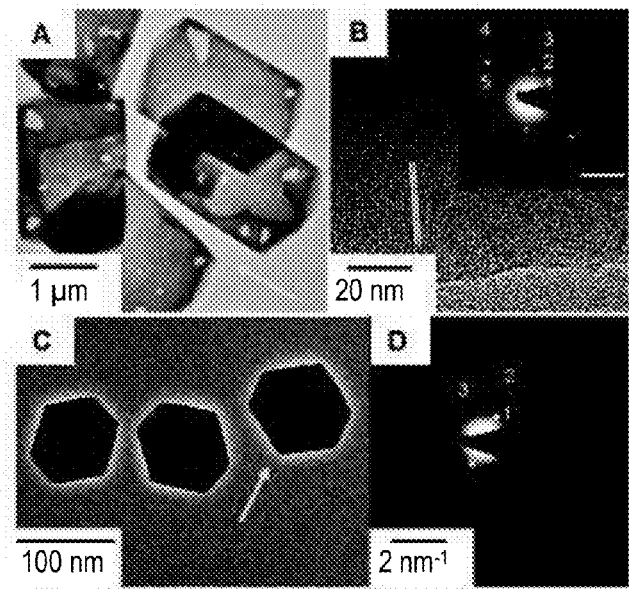
Fig. 26
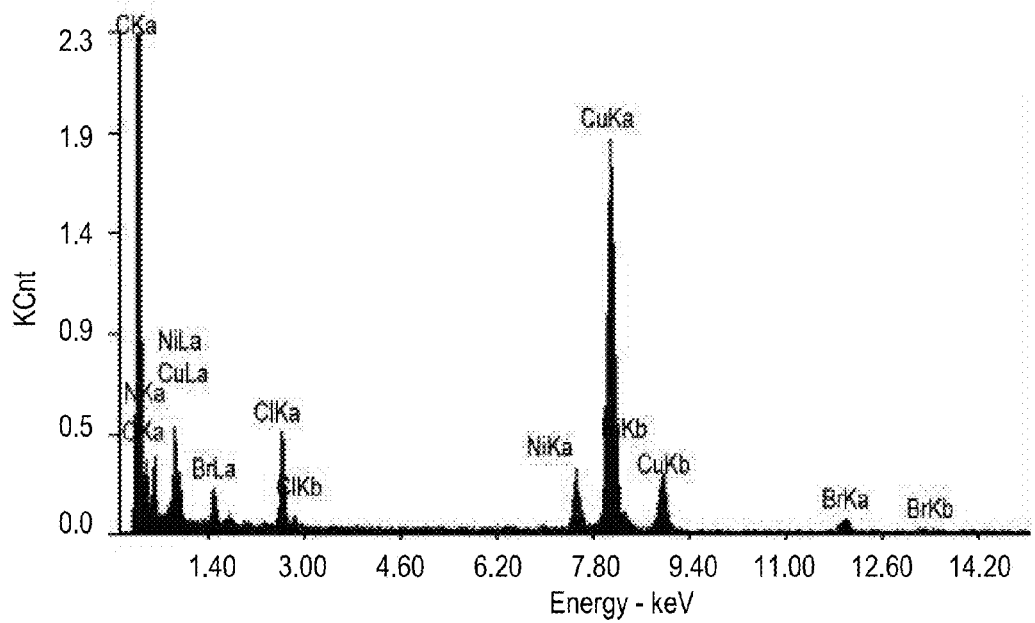

Fig. 27
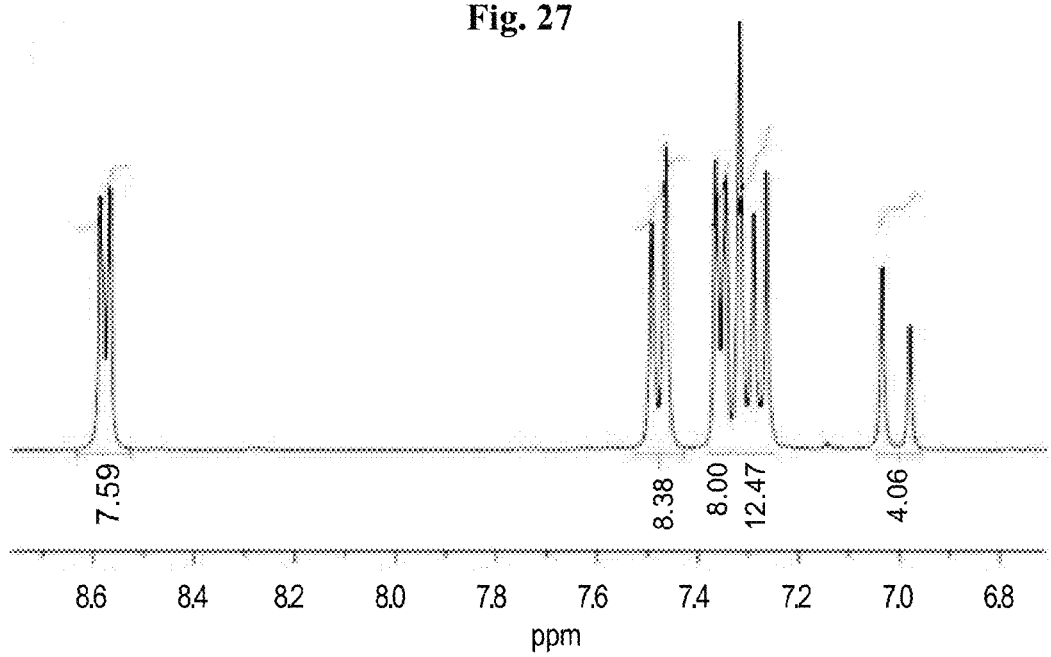
Fig. 28: panel A, panel B, panel C, panel D, panel E, panel F and panel G
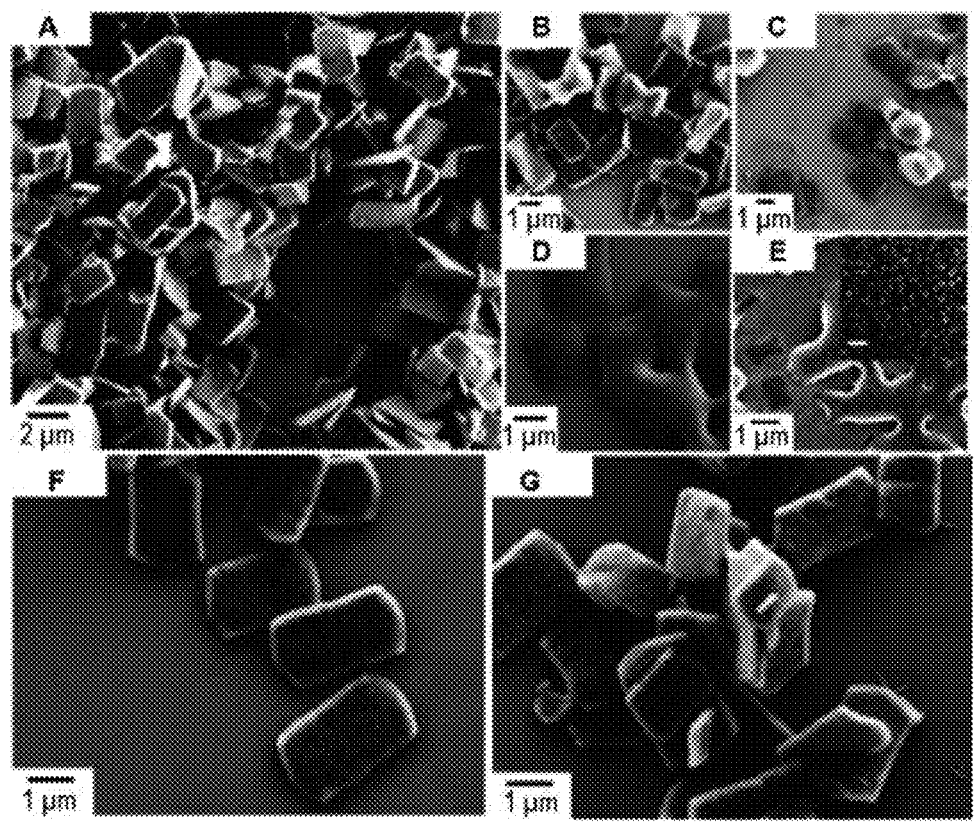

Fig. 29: panel A, panel B, panel C, panel D, panel E and panel F
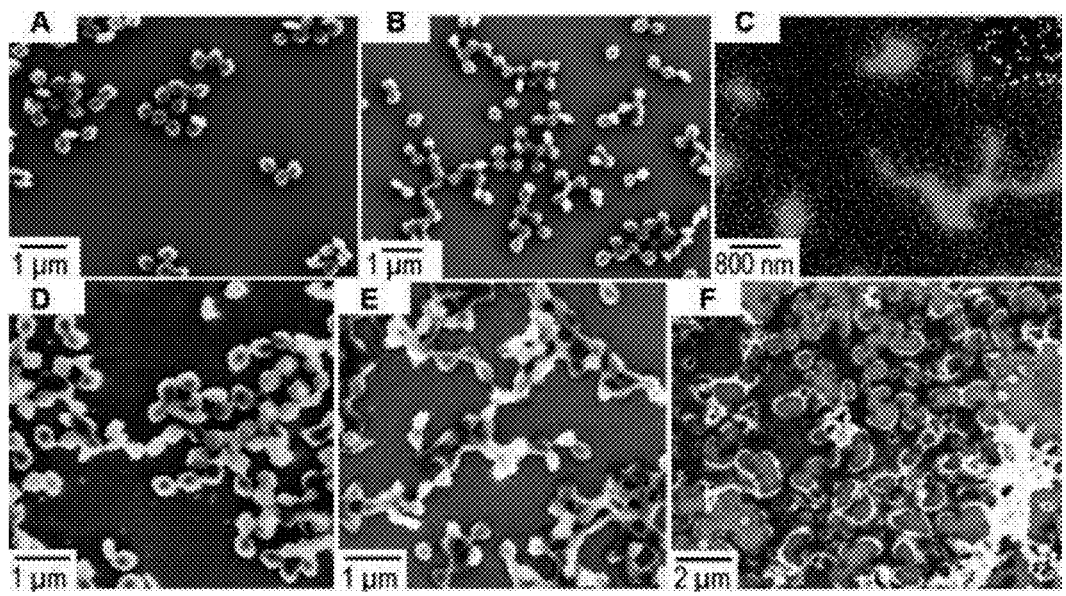
Fig. 30
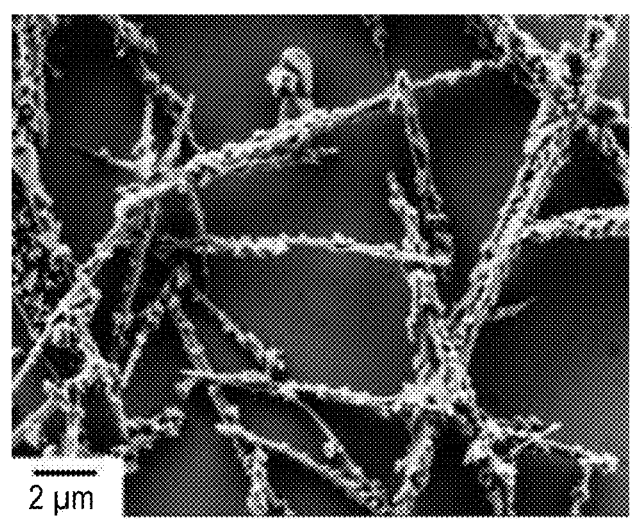

Fig. 31: panel A, panel B and panel C

Fig. 32: panel A, panel B and panel C

Fig. 36: panel A and panel B
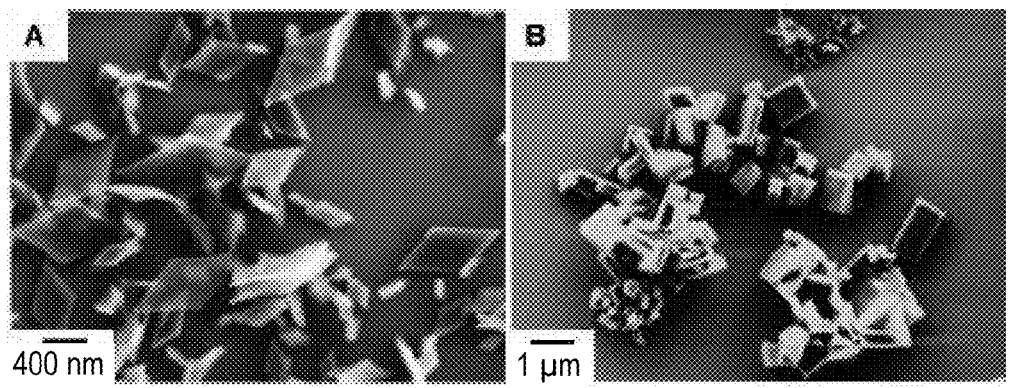
Fig. 37: panel A, panel B, panel C and panel D
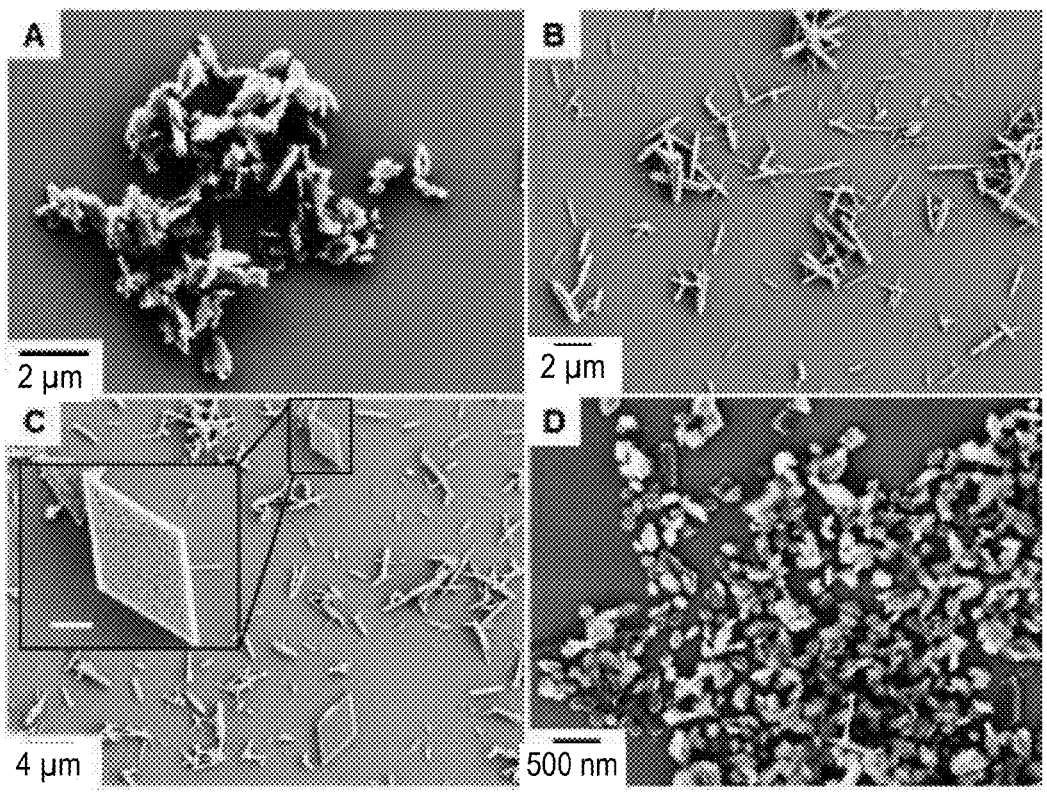

Fig. 38: panel A, panel B, panel C, panel D, panel E and panel F
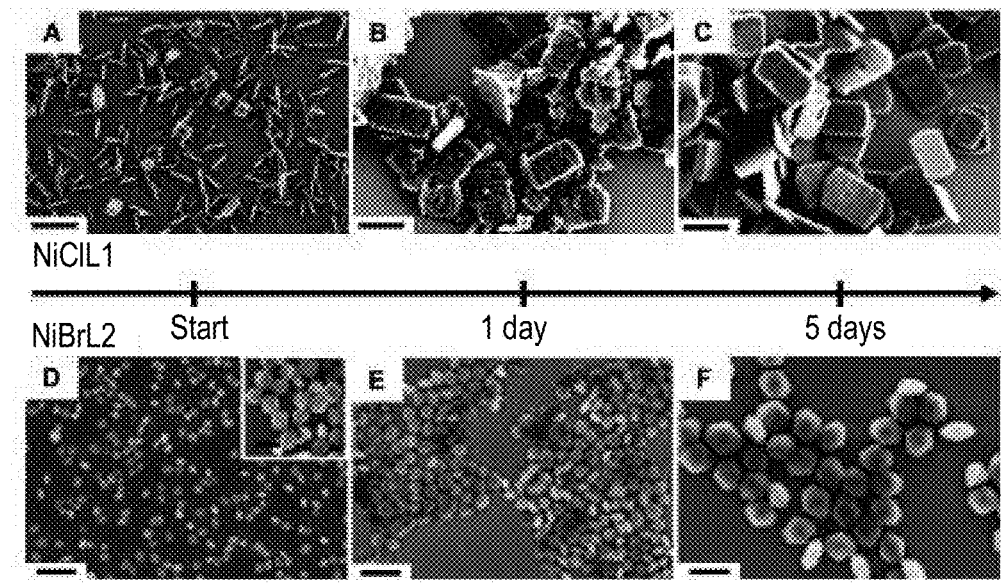
Fig. 39: panel A, panel B, panel C, panel D, panel D' and panel E
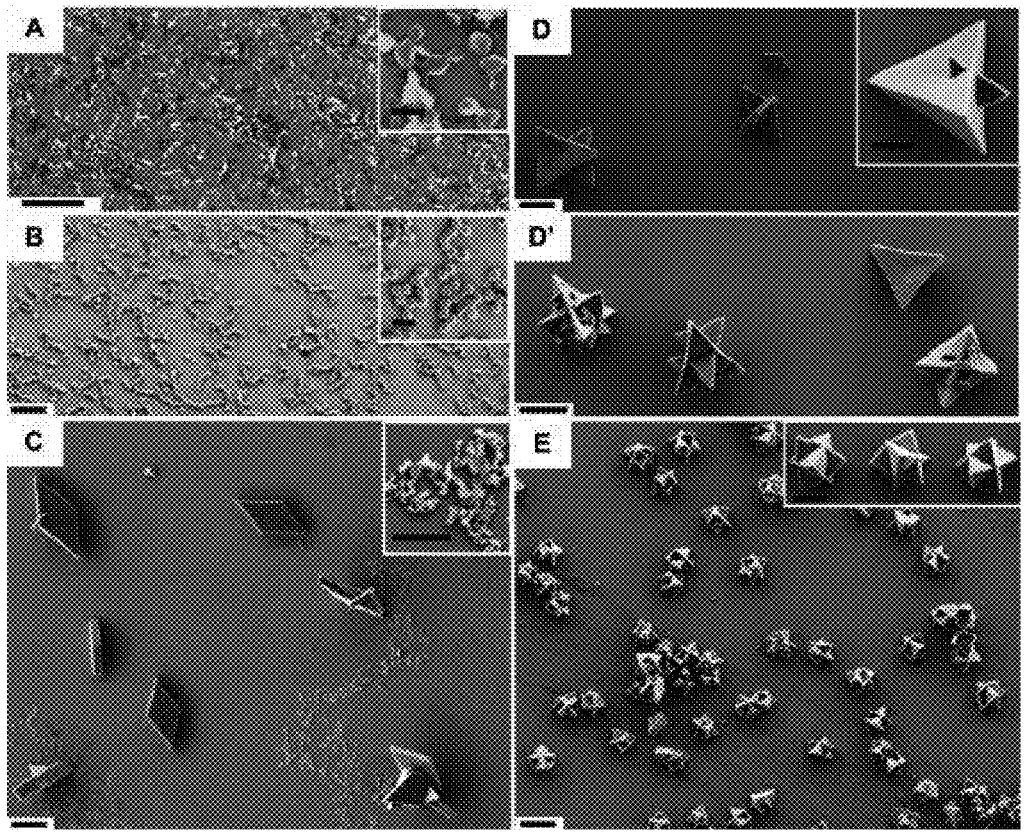

Fig. 40: panel A, panel B, panel C and panel D
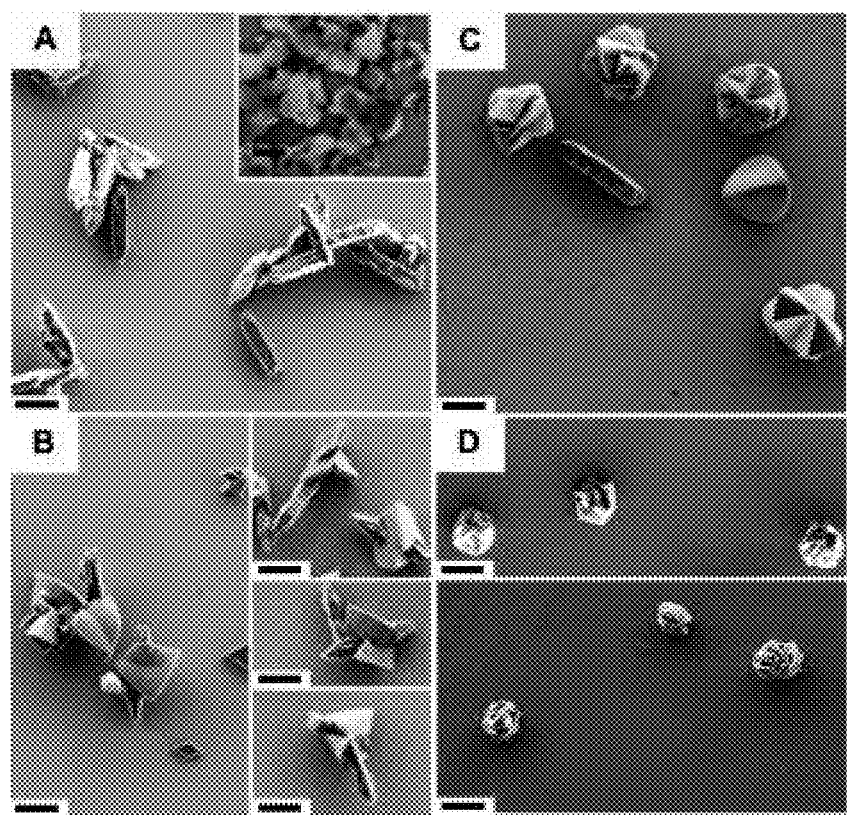

Fig. 43: panel A and panel B
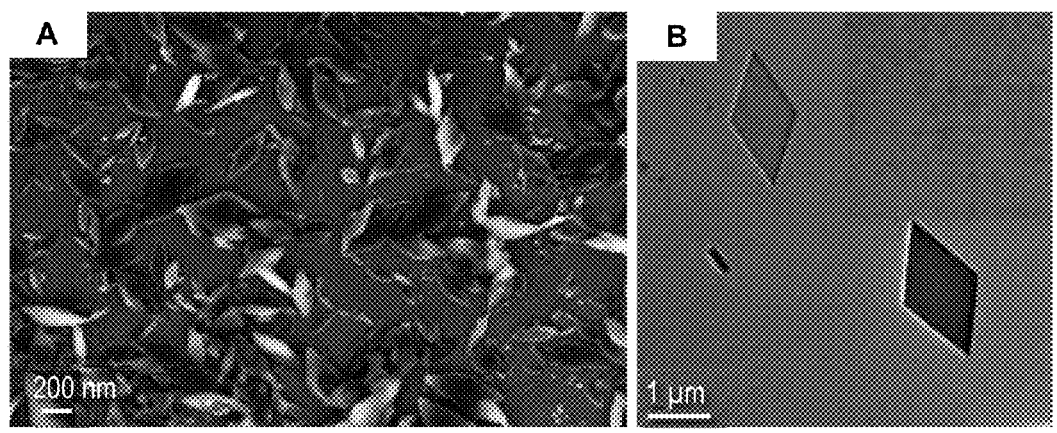
Fig. 44: panel A and panel B
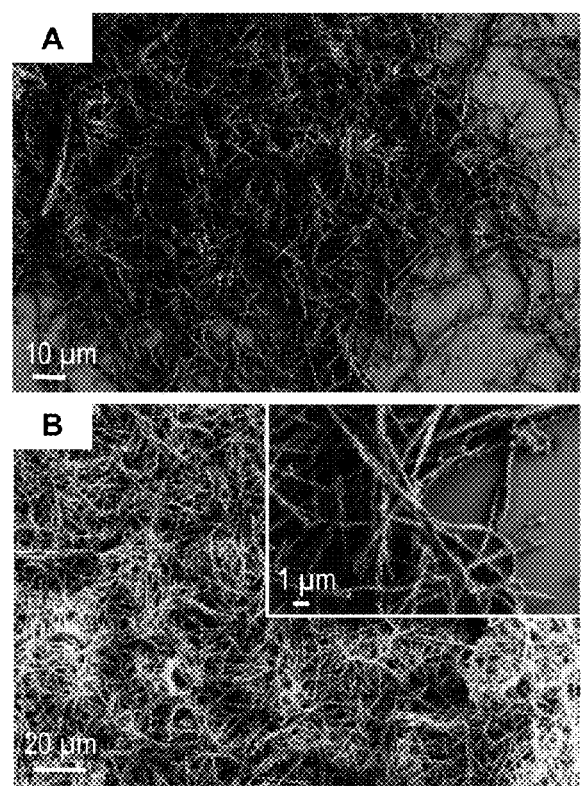

Fig. 47
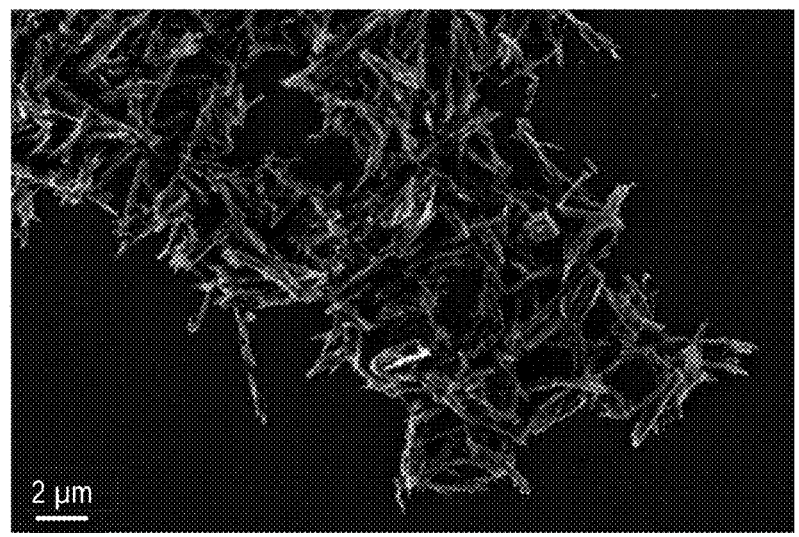
Fig. 48: panel A and panel B
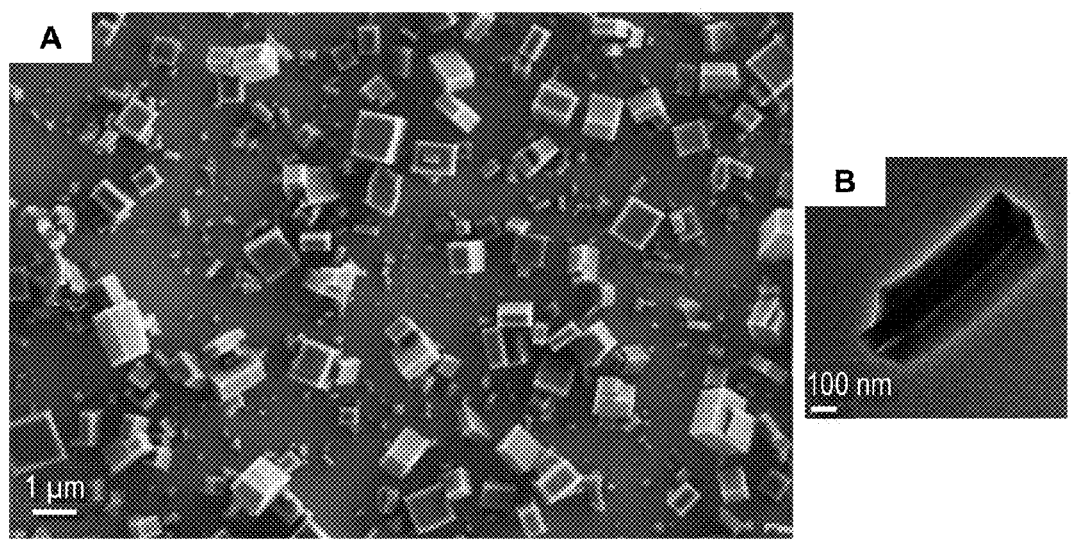

Fig. 49
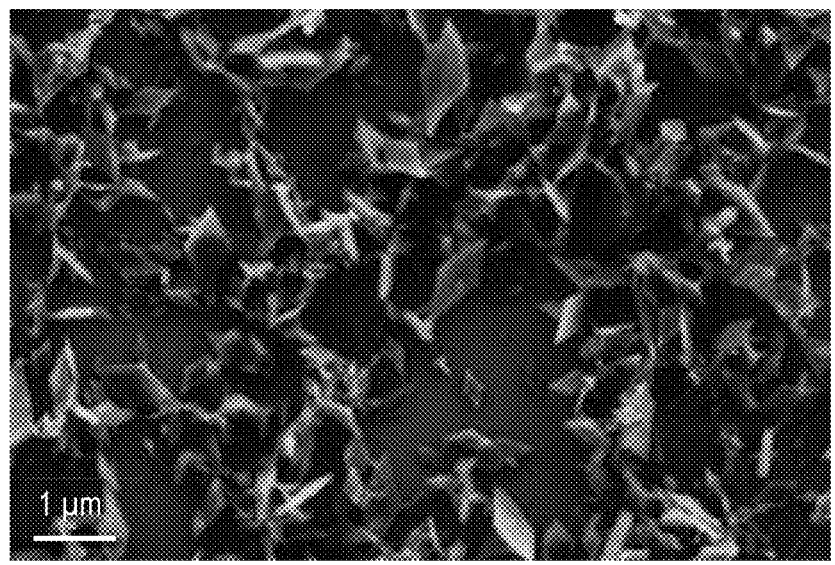
Fig. 50: panel A and panel B
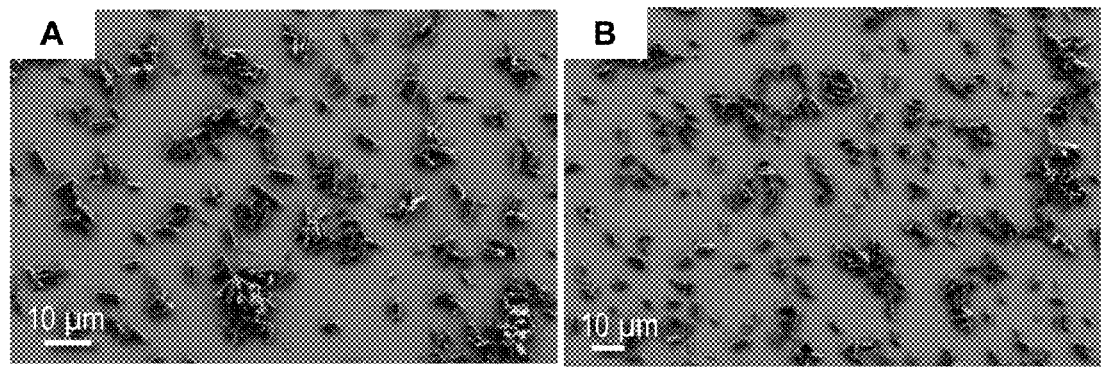

Fig. 51
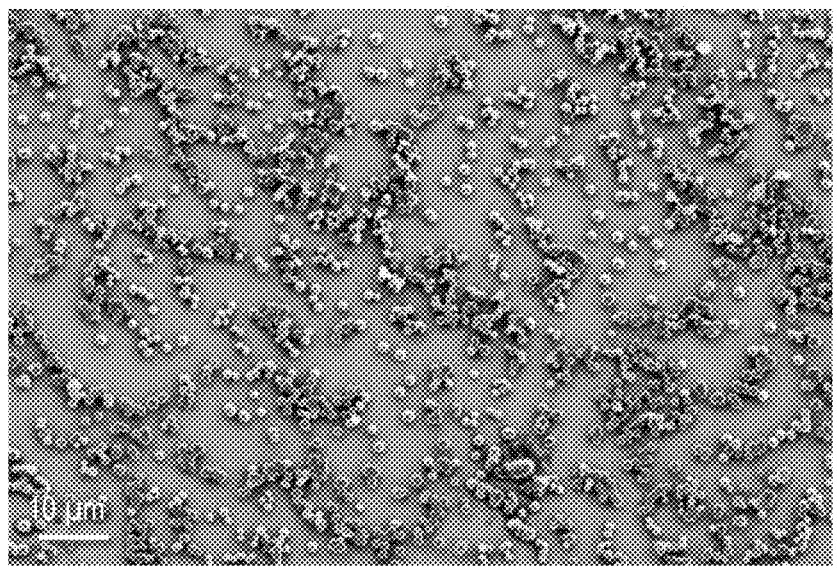
Fig. 52: panel A and panel B
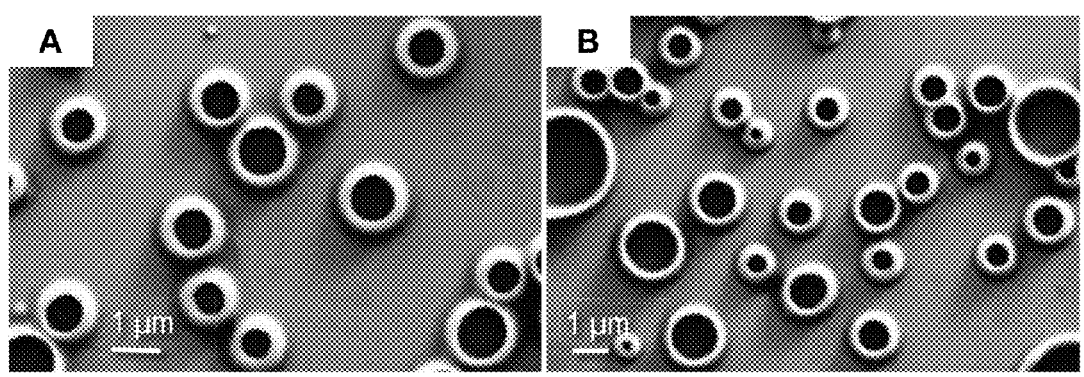

Fig. 57: panel A, panel B, panel C and panel D
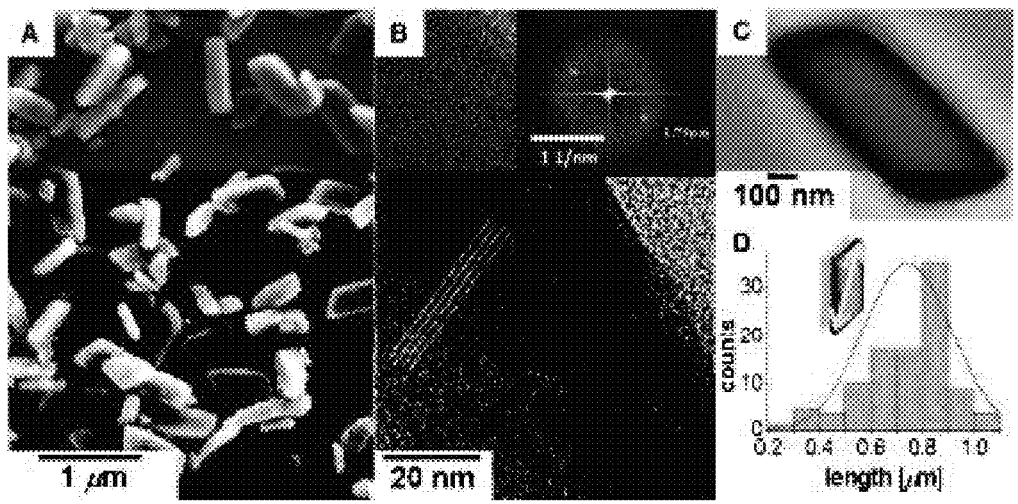
Fig. 58: panel A, panel B and panel C
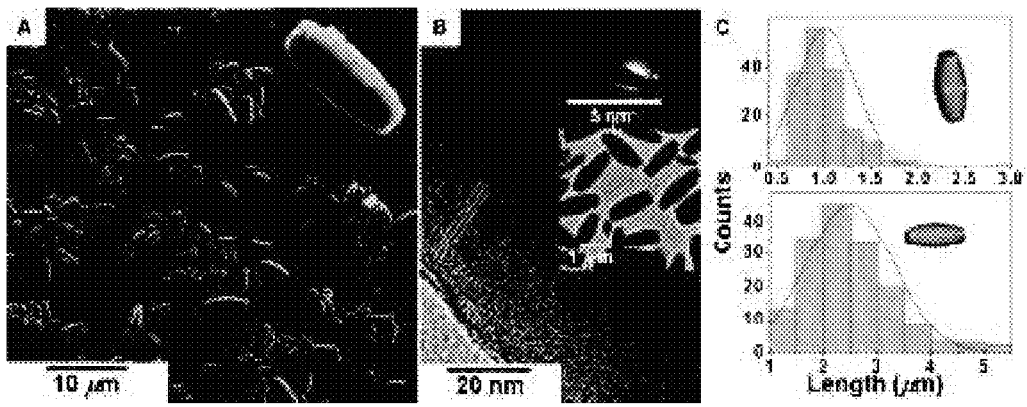

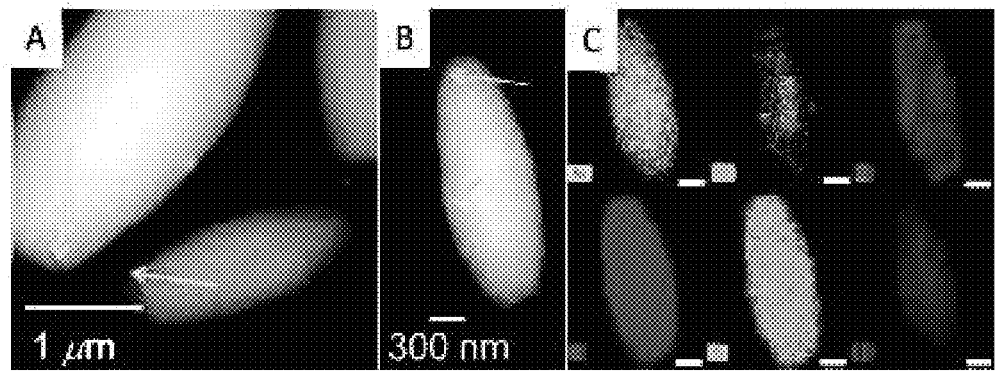
Fig. 59: panel A, panel B and panel C
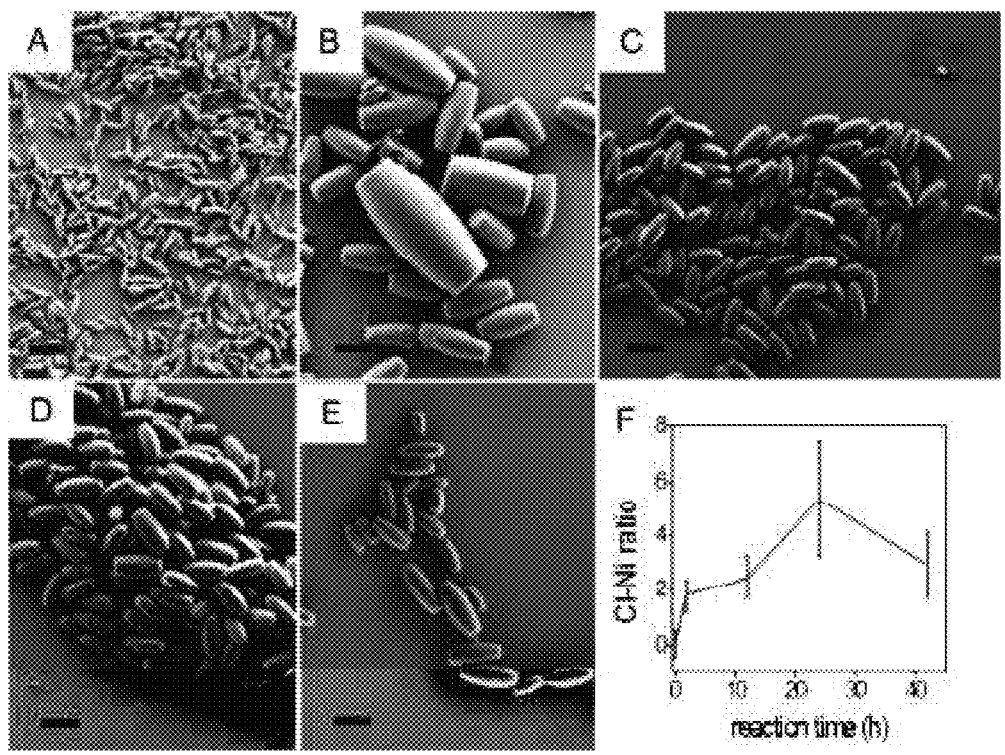
Fig. 60: panel A, panel B, panel C, panel E and panel F. Scale bar (panel A-E) = 2 μm

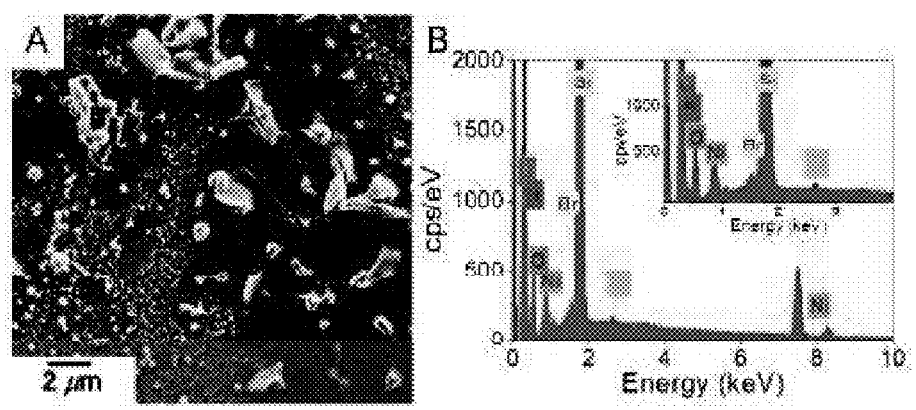
Fig. 61: panel A and panel B
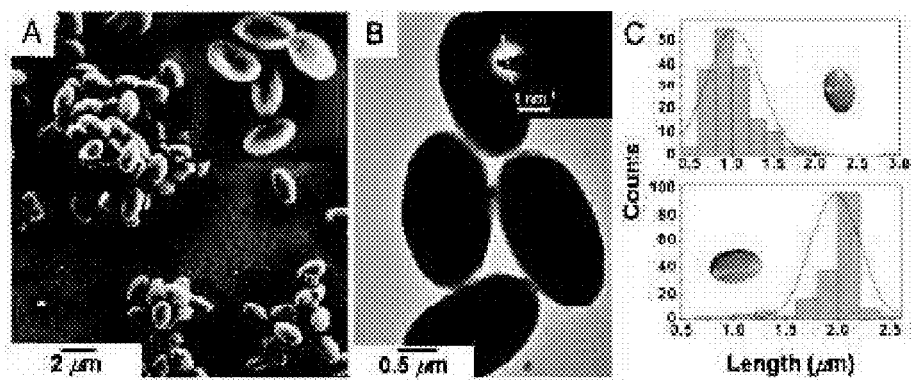
Fig. 62: panel A, panel B and panel C

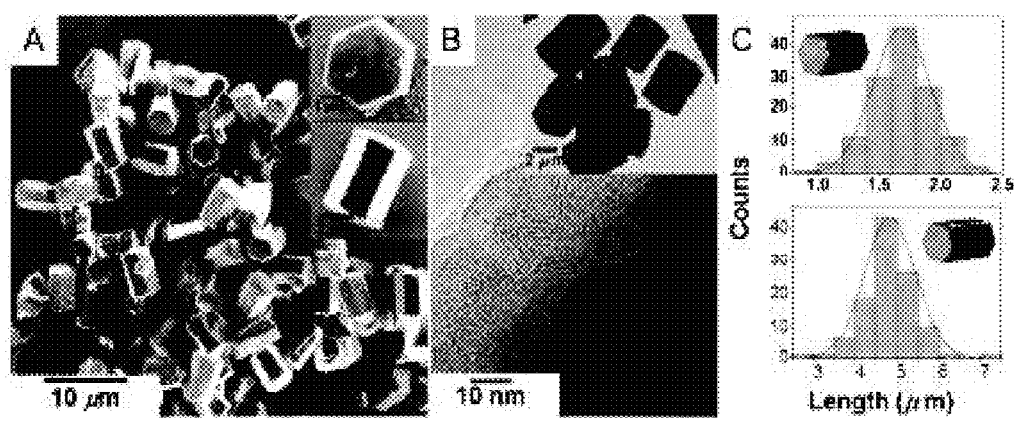
Fig. 63: panel A, panel B and panel C

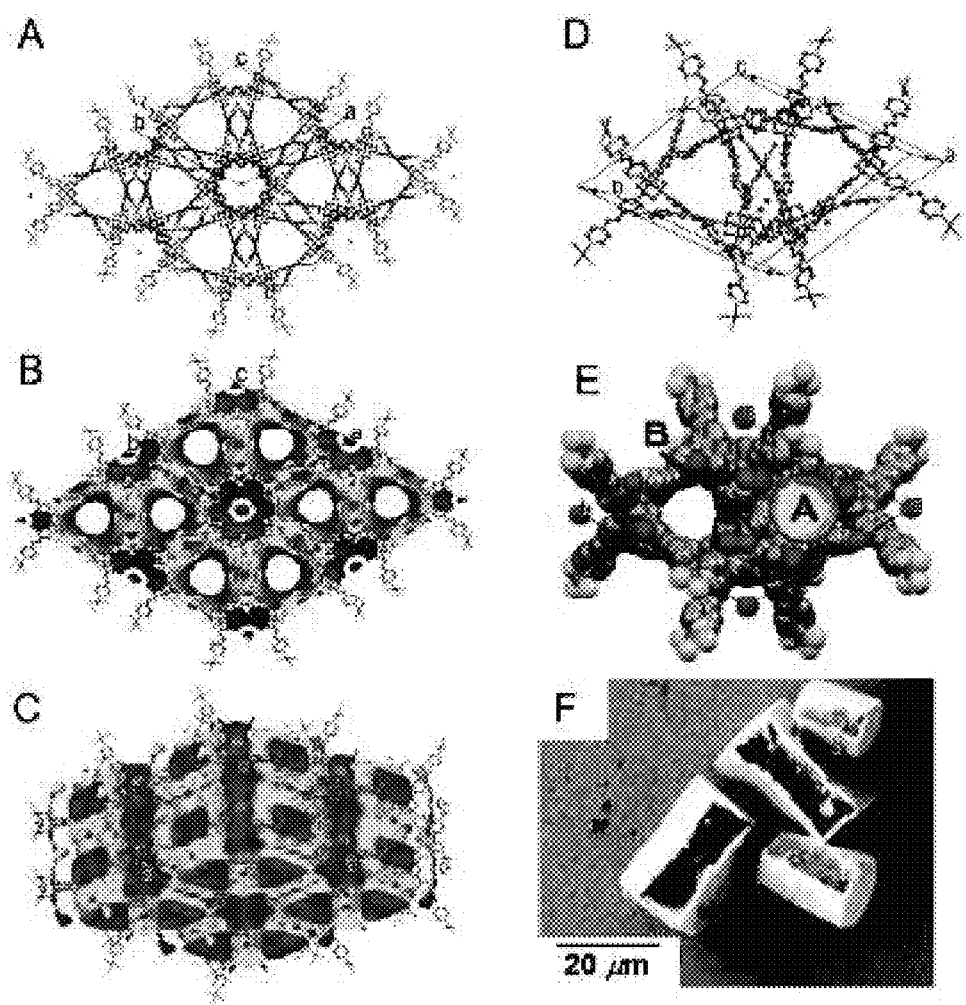
Fig. 64: panel A, panel B, panel C, panel D, panel E and panel F
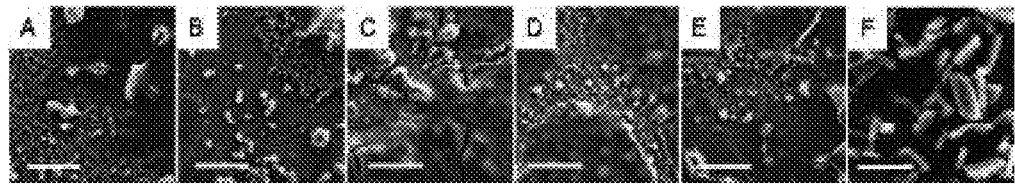
Fig. 65: panel A, panel B, panel C, panel D, panel E and panel F

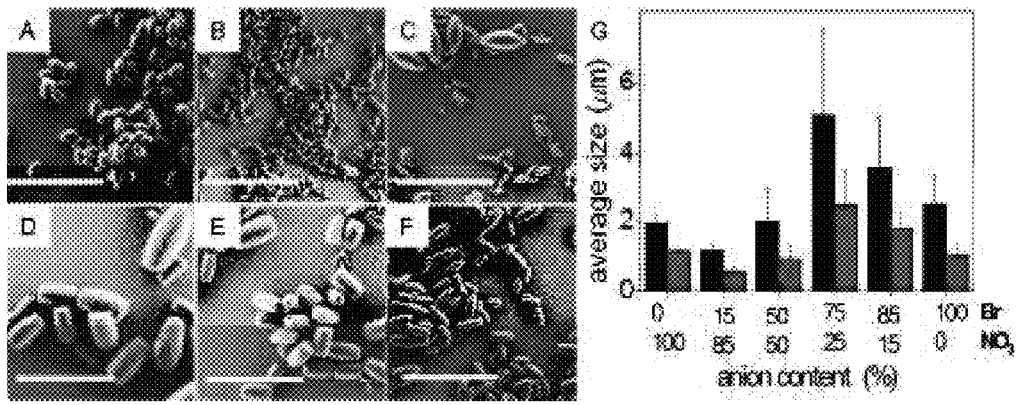
Fig. 66: panel A, panel B, panel C, panel D, panel E, panel F and panel G. Scale bar (panels A-G) = 10 μm
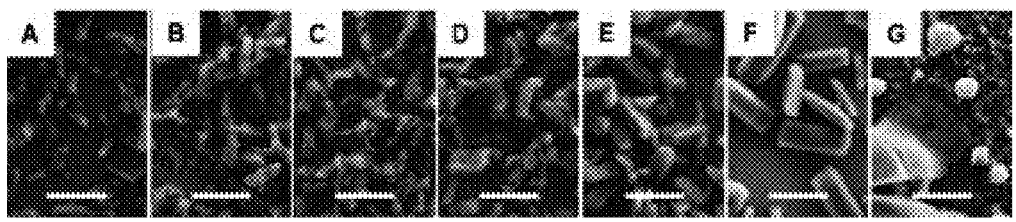
Fig. 67: panel A, panel B, panel C, panel D, panel E, panel F and panel G. Scale bar (panels A-G) = 1 μm
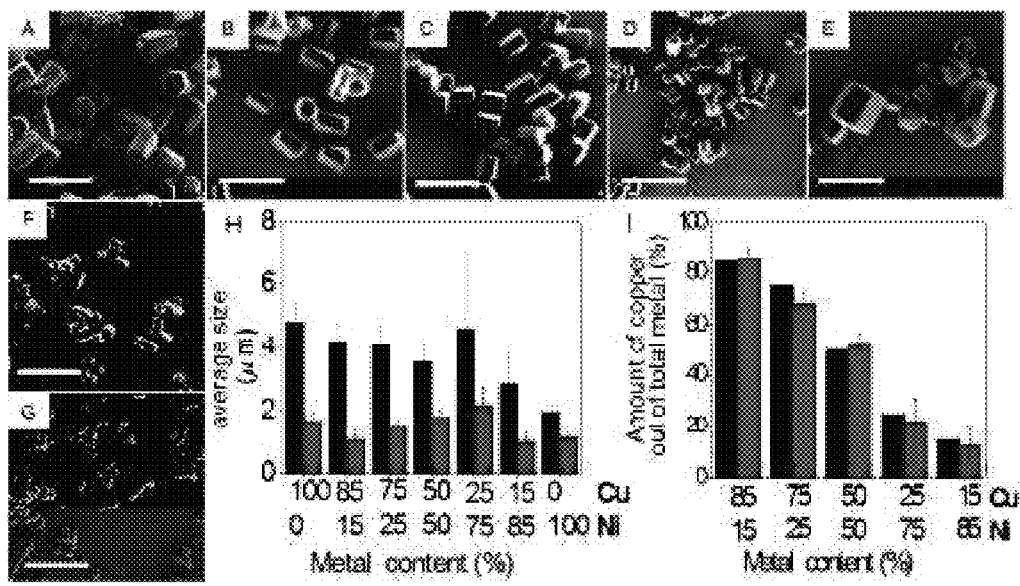
Fig. 68: panel A, panel B, panel C, panel D, panel E, panel F, panel G, panel H and panel I. Scale bar (panels A-G) = 10 μm

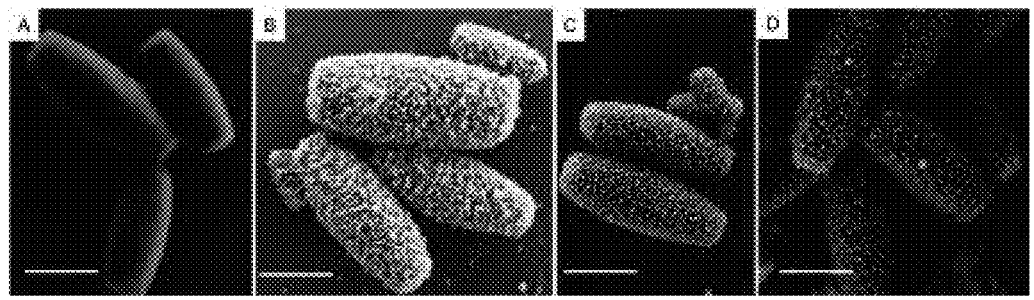
Fig. 69: panel A, panel B, panel C and panel D. Scale bar (panels A-D) = 1 μm
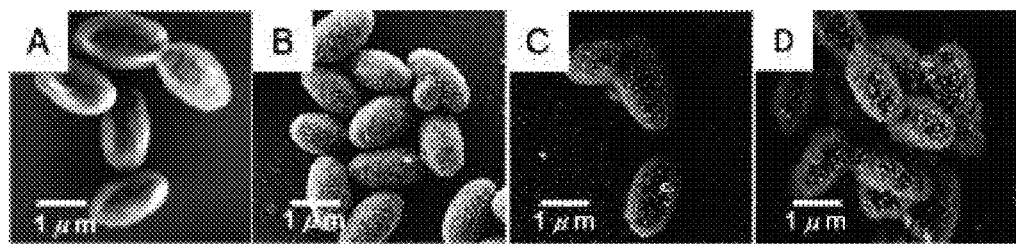
Fig. 70: panel A, panel B, panel C, and panel D
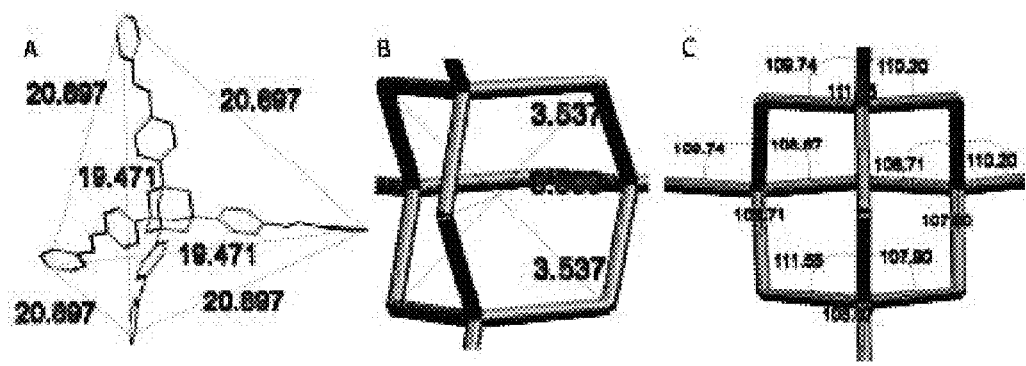
Fig. 71: panel A, panel B and panel C

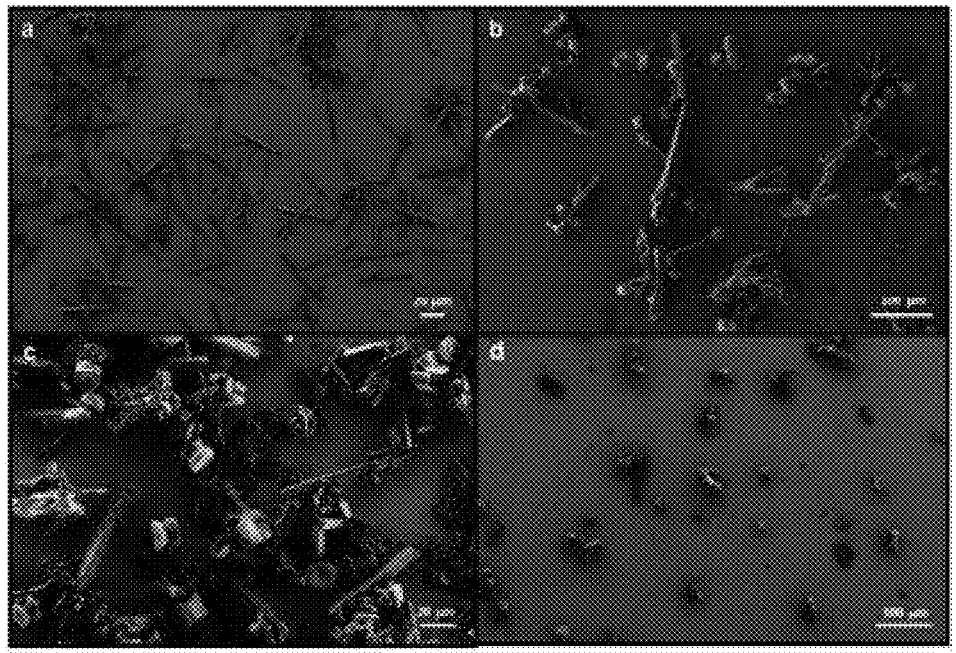
Fig. 72: panel A, panel B, panel C and panel D
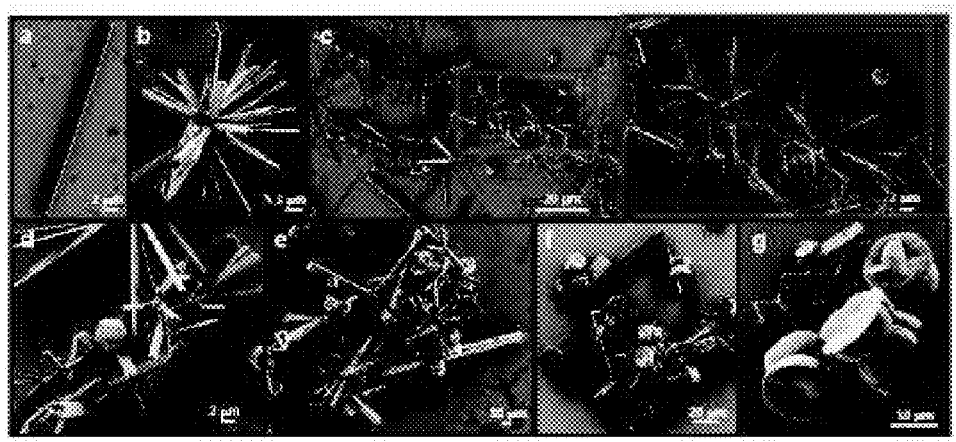
Fig. 73: panel A, panel B, panel C, panel D, panel E, panel F and panel G

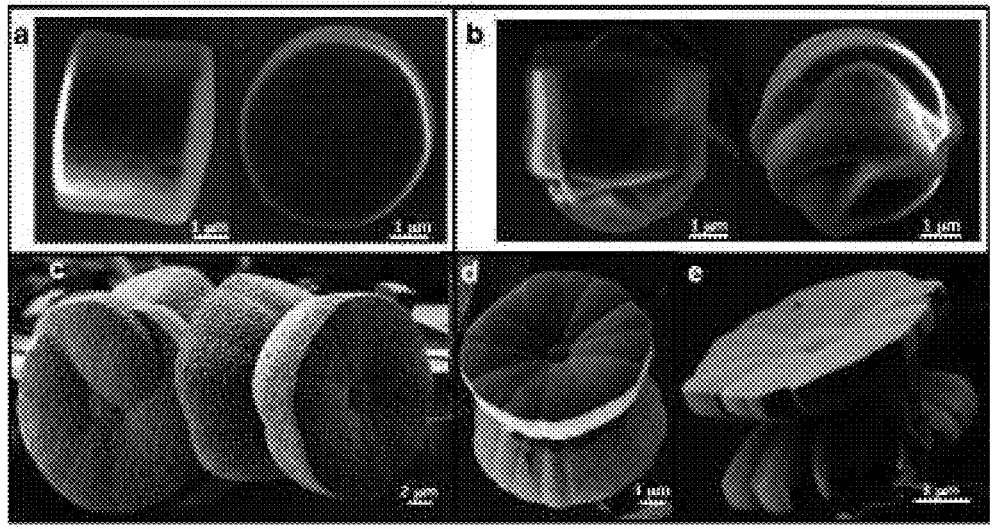
Fig. 74: panel A, panel B, panel C, panel D and panel E
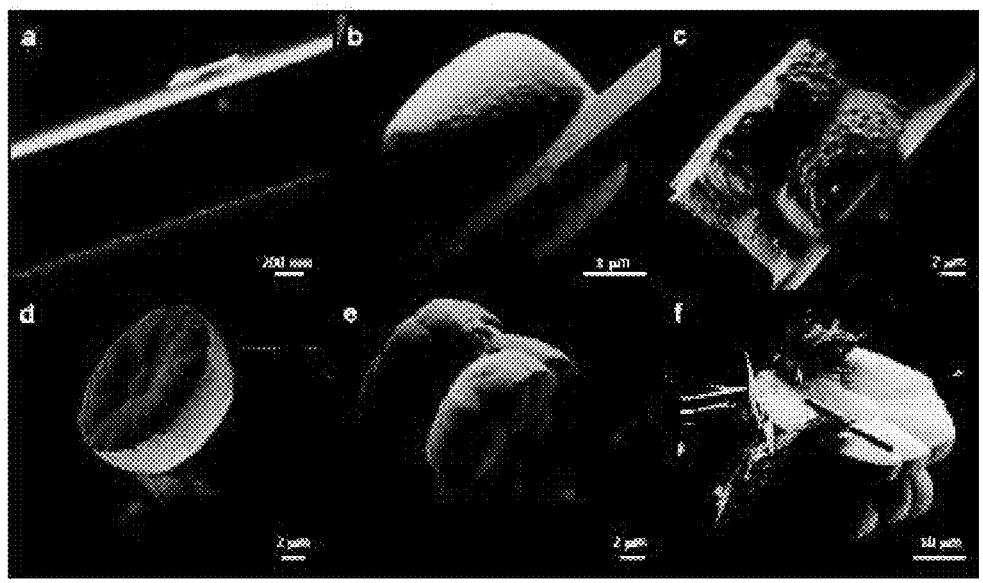
Fig. 75: panel A, panel B, panel C, panel D, panel E and panel F

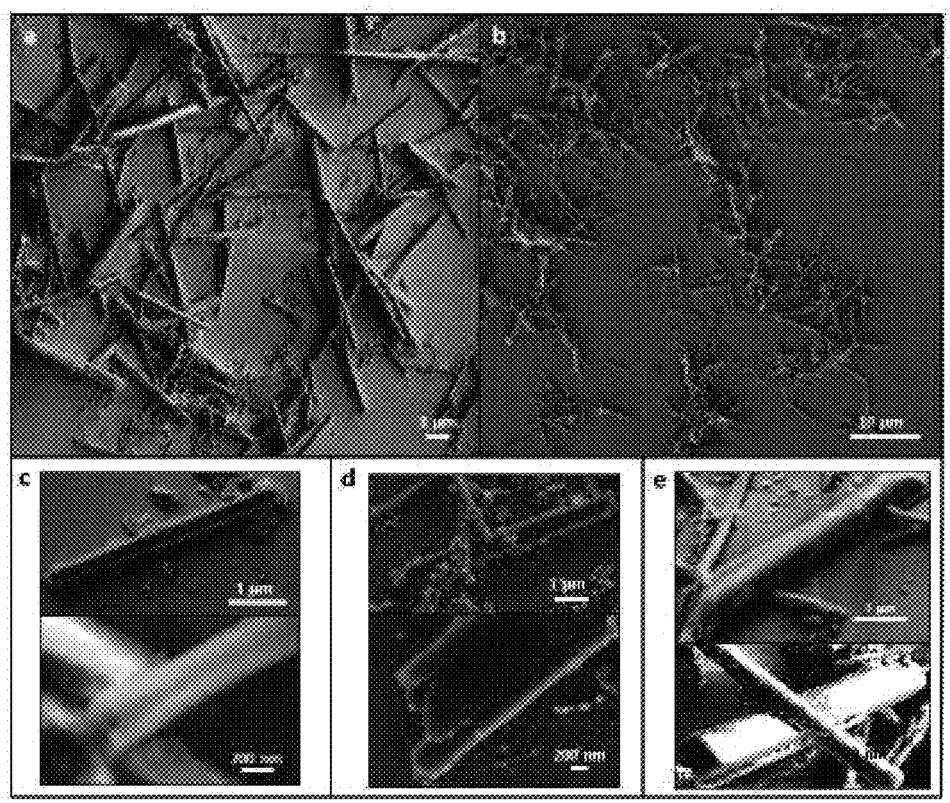
Fig. 76: panel A, panel B, panel C, panel D and panel E

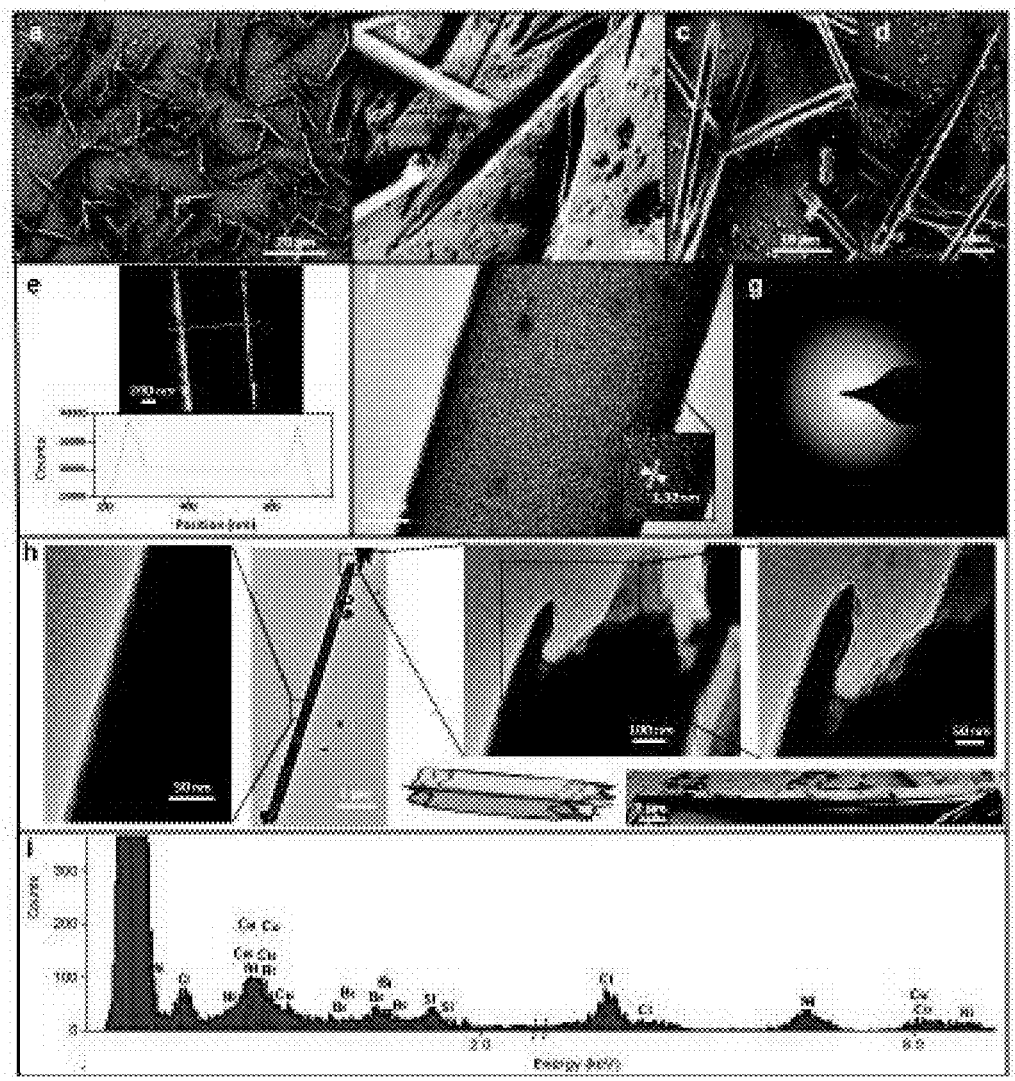
Fig. 77: panel A, panel B, panel C, panel D, panel E, panel F, panel G, panel H and panel I

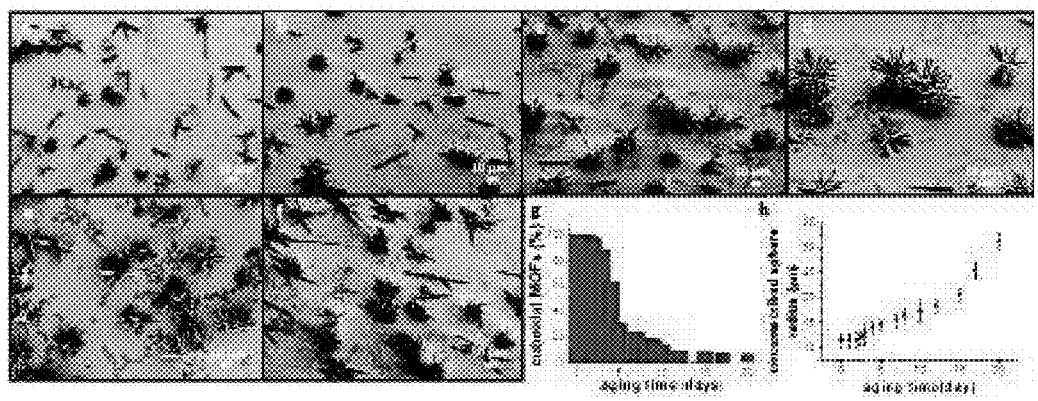
Fig. 78: panel A, panel B, panel C, panel D, panel E, panel F, panel G and panel H
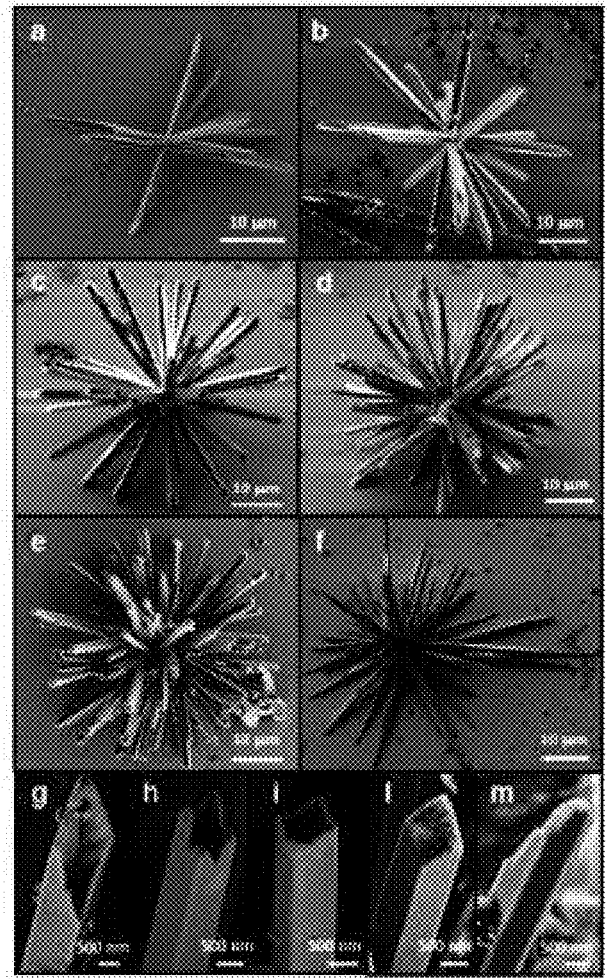
Fig. 79: panel A, panel B, panel C, panel D, panel E, panel F, panel G, panel H, panel I, panel L and panel M

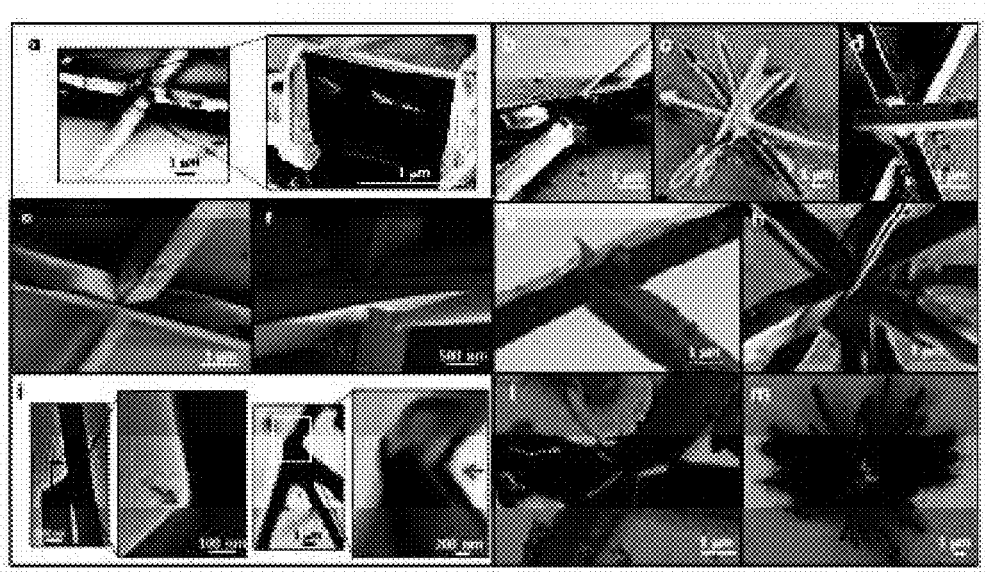
Fig. 80: panel A, panel B, panel C, panel D, panel E, panel F, panel G, panel H, panel I, panel L and panel M
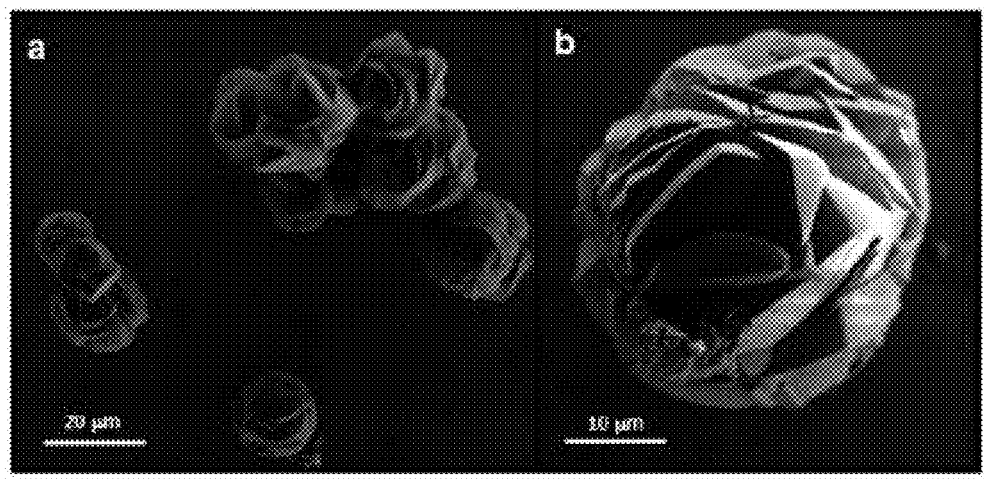
Fig. 81: panel A and panel B

METAL-ORGANIC MATERIALS AND METHOD FOR PREPARATION

CROSS-REFERENCE TO RELATED APPLICATIONS

This application is a continuation-in-part of U.S. application Ser. No. 14/904,708, filed on Jan. 13, 2016, which is a National Phase Application of PCT International Application No. PCT/IL2014/050632, filed on Jul. 13, 2014, which claims the benefit of U.S. Provisional Application No. 61/846,021, filed on Jul. 14, 2013, hereby incorporated by reference.

TECHNICAL FIELD

The present invention provides metal-organic materials comprising polypyridyl organic ligands and metal ions structurally coordinated with said ligands, and a method for the preparation thereof.

Abbreviations: AFM, atomic force microscope; CP, coordination polymer; DMF, dimethylformamide; EDS, energy dispersive spectroscopy; FC, field cooled; FT-IR, infrared Fourier transform spectrophotometer; MOF, metal-organic framework; RT, room temperature; RTP, rapid thermal processing; SAED, selected area electron diffraction; SEM, scanning electron microscope; SQUID, superconducting quantum interference device; TEM, transmission electron microscope; TGA, thermogravimetric analysis; XRD, X-ray diffraction; ZFC, zero field cooled;

BACKGROUND ART

Research related to metal-organic frameworks (MOFs) as well as coordination polymers (CPs) (for a perspective understanding of the differences between the terms CP, MOF and hybrid organic-inorganic materials, see Biradha et al., Cryst. Growth Des., 2009, 9, 2969-2970) has been treated with overwhelming interest by the scientific community of chemists and physicists due to tunable properties of these molecular assemblies by controlling their growth, size and shape, and their potential applications in the fields of catalysis, gas storage, separation, recognition and purification, optics, sensors, etc. (Zhao, et al., Science, 2004, 306, 1012; Yaghi, et al., Nature, 2003, 423, 705; Seo, et al., Nature, 2000, 404, 982; Kitagawa, et al., Angew. Chem., Int. Ed. 2004, 43, 2334; Evans, et al., Acc. Chem. Res. 2002, 35, 511; Rowsell, et al., Angew. Chem., Int. Ed. 2005, 44, 4670; Tabellion, et al., J. Am. Chem. Soc. 2001, 123, 7740; Lei, et al., J. Phys. Chem. C. 2007, 111, 11291; Zhao, et al., Inorg. Chem. 2008, 47, 7133; Chen, et al., Acc. Chem. Res. 2010, 43, 1115). It was in 1964 that J. C. Bailar defined the term "coordination polymer" (Bailar, J. C., Jr Prep. Inorg. React. 1964, 1, 1-57) and a wide variety of techniques such as solvothermal (Jung, et al., Angew. Chem., Int. Ed. 2008, 47, 2049-2051; Ni, et al., J. Am. Chem. Soc. 2006, 128, 12394-12395), precipitation (Oh, et al., Nature 2005, 438, 651-654; Oh, et al., Angew. Chem., Int. Ed. 2006, 45, 5492-5494; Sun, et al., J. Am. Chem. Soc. 2005, 127, 13102-13103; Park, et al., J. Am. Chem. Soc. 2006, 128, 8740-8741; Wei, et al., Chem. Mater. 2007, 19, 2987-2993) and reverse microemulsion (Rieter, et al., J. Am. Chem. Soc. 2006, 128, 9024-9025) methods have been employed in the generation of shape selective nano and micro structured CPs (Wang, et al., Chem. Commun. 2009, 5457-5459; Shi, et al., Chem. Commun. 2011, 47, 5055-5057; Liu, et al., Cryst. Growth Des. 2010, 10, 790-797; Lu, et al., J. Mater. Chem. 2011, 21, 8633-8639; Li, et al., J. Mat. Chem. 2011, 21, 17946-17952; Cho, et al., J. Am. Chem. Soc. 2008, 130, 16943-16946).

Structural uniformity is a prerequisite for many real-world applications including oriented fabrication of various materials, often in size-confined regimes (Tuxen, et al., J. Am. Chem. Soc. 2013, 135, 2273-2278). At the same time, structural diversity can lead to control of desired physical and chemical properties (Noorduin, et al., Science 2013, 340, 832-837; Pevzner, et al., Nano Lett. 2012, 12, 7-12; Whitesides, et al., Science 2002, 295, 2418-2421; Masoomi, et al., RSC Adv., 2013, 3, 19191-19218; Gu, et al., Nano Lett. 2012, 12, 6385-6392). Molecular self-assembly allows the construction of composite superstructures with unique structure and properties. Size and shape confined synthesis of such composites are advantageous for their intrinsic and complex multi-functionalities, allows addressing properties of individual components and the combination thereof, and the possibilities of their spatial integration into devices and onto surfaces (Carné-Sánchez, et al., Chem. Eur. J. 2014, 20, 5192-5201). Needless to say "structure dictates function at all scales" (Tao, et al., Small 2008, 4, 310-325).

Due to their unique, often porous structures and special properties achieved through synthetic tunability, MOFs have been actively studied over the last few decades (Furukawa, et al., Science 2013, 341, 1230444; Cook, et al., Chem. Rev. 2013, 113, 734-777; Long, et al., Chem. Soc. Rev. 2009, 38, 1213-1214). However, control over their spatial topologies at the micro and nano levels is still limited and difficult to achieve (Stock, et al., Chem. Rev. 2011, 112, 933-969; Sindoro, et al., Acc. Chem. Res. 2014, 47, 459-469). Many variables, e.g., anions, solvents, and electronic configuration, play a key role in the formation of geometrically well-defined and uniform shapes. Thus far, the shapes of MOFs are limited to simple polyhedra (Sindoro et al., Acc. Chem. Res. 2014, 47, 459).

SUMMARY OF INVENTION

One embodiment of the invention encompasses a metal-organic material comprising at least two metal ions and at least four ligands, wherein the ligand is represented by formula L4

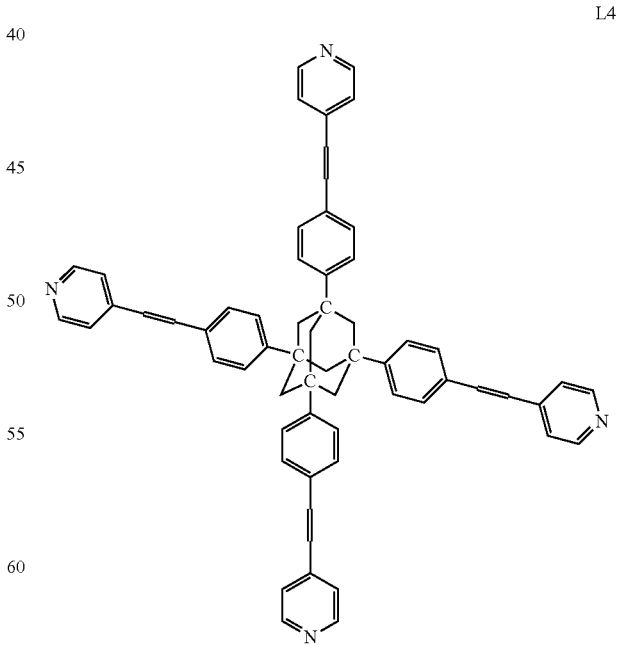

L4

In another embodiment, the metal ion is $Ni^{2+}$ or $Cu^{2+}$ and is present as a salt. The metal to ligand ratio may be 1:2 to 1:10 or 1:2 to 1:4. In one embodiment, the metal ion is present as a salt of NiBr$_2$, Ni(NO$_3$)$_2$, or Cu(NO$_3$)$_2$. In yet another embodiment, the metal ions are Ni$^{2+}$ and Cu$^{2+}$ in a ratio of 1:1. The metal ions may be present as NiBr$_2$ and Ni(NO$_3$)$_2$ in a 1:1 ratio. The metal-organic material may be crystalline and the crystalline material is in the shape of an egg, barrel, or hexagonal prism.

In yet another embodiment, the metal-organic material is coated with Au nanoparticles.

Another embodiment of the invention encompasses a metal-organic material comprising at least two metal ions and at least four ligands, wherein the ligand is represented by formula L3

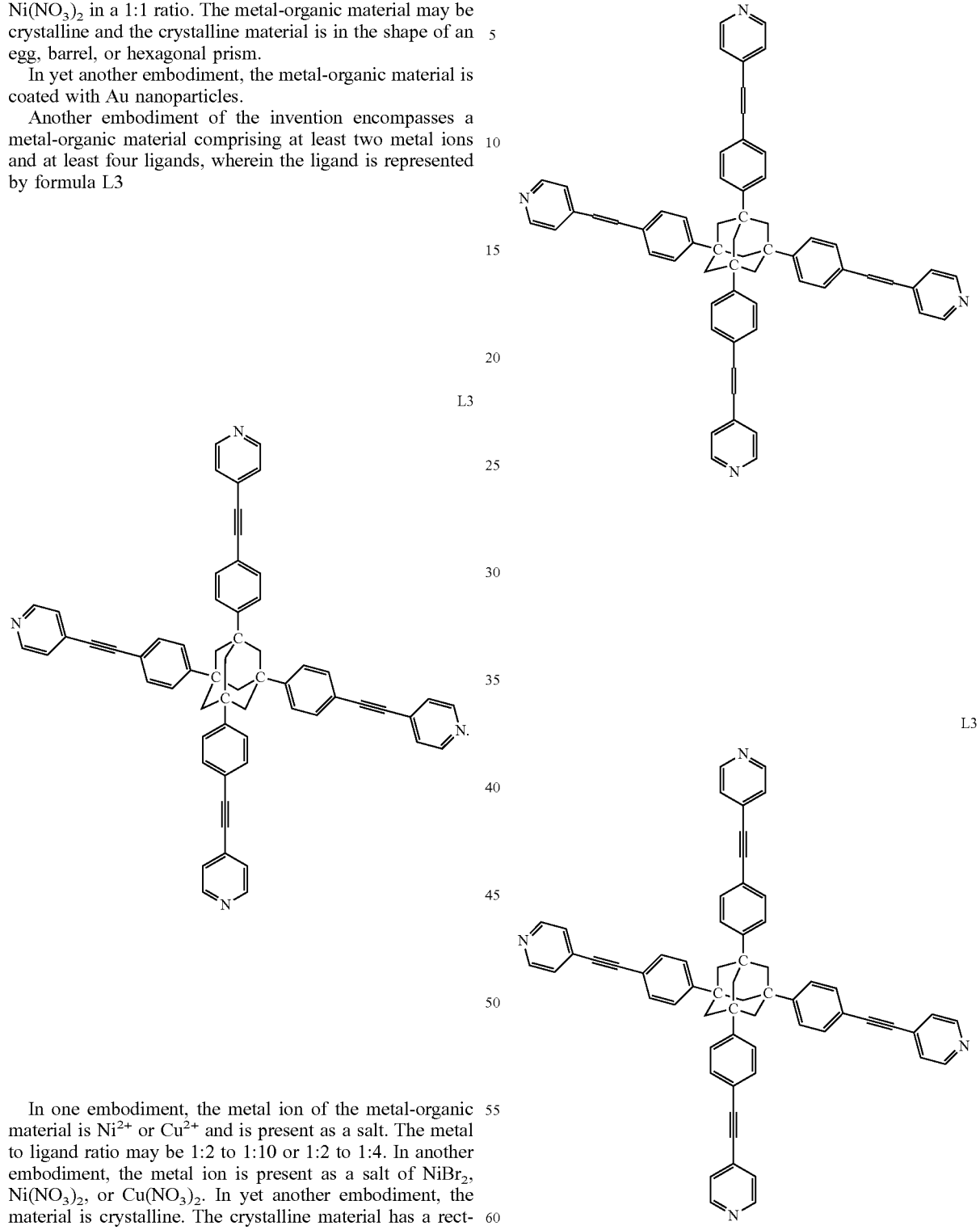

In one embodiment, the metal ion of the metal-organic material is Ni$^{2+}$ or Cu$^{2+}$ and is present as a salt. The metal to ligand ratio may be 1:2 to 1:10 or 1:2 to 1:4. In another embodiment, the metal ion is present as a salt of NiBr$_2$, Ni(NO$_3$)$_2$, or Cu(NO$_3$)$_2$. In yet another embodiment, the material is crystalline. The crystalline material has a rectangular cross-section, and this rectangular cross section is from about 400 nm to about 700 nm or from about 674 nm to about 361 nm. In one embodiment, the crystalline material is cylinder shaped or in an elongated cuboidal shape.

In another embodiment, the invention encompasses a compound of formula L3, formula L4, formula C, or formula E:

-continued

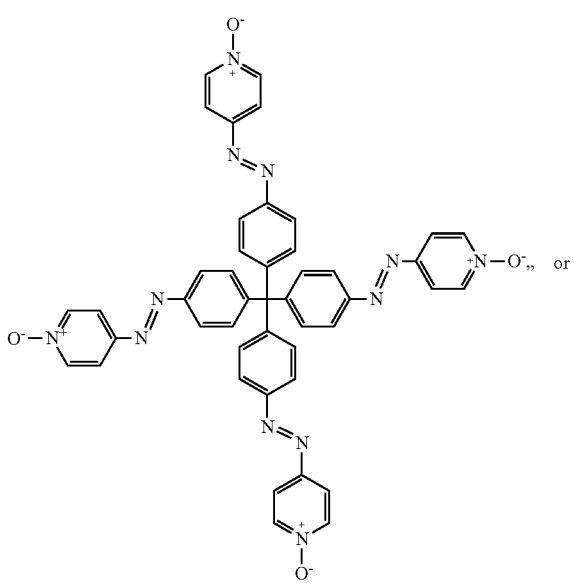

Formula C

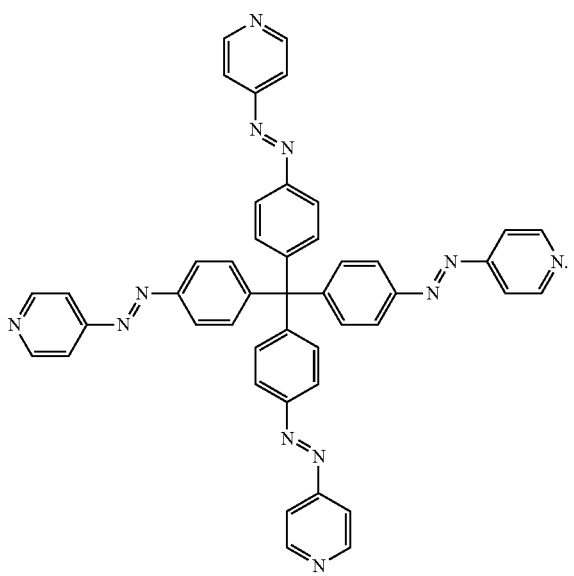

Formula E

In yet another embodiment, the compound L3 or L4 is in crystalline form. In the crystalline form the distance between the nitrogen atoms of the pyridine ring is about 20.89 Å or 19.47 Å.

BRIEF DESCRIPTION OF DRAWINGS

(FIG. 1B) distribution of length and breadth of the microbricks. Each bar corresponds to the counts in the interval x to (x+0.2) μm. AFM measurements indicated a thickness of 200-300 nm.

FIGS. 2A-2B show TEM image of the brick-like microstructures (NiClL1) (FIG. 2A); and TEM image showing the diffraction grating (inset-electron diffraction, scale bar=1 nm$^{-1}$) (FIG. 2B).

FIGS. 3A-3D show AFM topography of NiClL1 (scale bar=1 μm) (FIG. 3A); height profile corresponding to the vertical line in 3A of an individual crystallite (FIG. 3B); AFM topography of NiBrL2 (FIG. 3C); and height profile corresponding to the horizontal line in 3C of an individual crystallite (FIG. 3D).

FIG. 10 shows SEM image of NiClL1 taken using an In Lens Detector. Inset-optical microscope image of NiClL1 confirming the microstructure.

FIGS. 11A-11C shows SEM images showing the brick-like microstructures of NiClL1 suspended for 2 months in DMF (FIG. 11, panel A); water (FIG. 11, panel B); or a 1:1 v/v mixture of DMF/water (FIG. 11, panel C) at RT in air with exclusion of light.

FIGS. 12A-12B shows SEM image of the microstructures obtained by heating in a sealed pressure tube at 105° C. for 5 days a DMF solution (3.0 ml) of NiCl$_2$.6H$_2$O (1.6 mg, 6.9 μmol) and a CHCl$_3$ solution (1.0 ml) of L1 (5.0 mg, 6.9 μmol) without stirring and with exclusion of light (FIG. 12, panel A); and a magnified image (FIG. 12, panel B).

FIGS. 13A-13D shows solvent effect on the microstructure of NiClL1. SEM images: DMF:CHCl$_3$ 3:1 (v/v) (FIG. 13, panel A); DMF (FIG. 13, panel B); DMF:CHCl$_3$ 2:1 (v/v) (FIG. 13, panel C); and DMF:CHCl$_3$ 3:1 (v/v)+0.5 ml H$_2$O (FIG. 13, panel D), (scale bar=10 μm). Each experiment was performed under solvothermal conditions at 105° C. for 5 days using a CHCl$_3$ solution of L1 (5.0 mg, 6.9 μmol) and a DMF solution (total volume 4 ml) of NiCl$_2$.6H$_2$O (3.2 mg, 13.8 μmol).

FIGS. 14A-14D shows SEM images after RTP at 300° C. (FIG. 14, panel A); 400° C. (FIG. 14, panel B); 500° C. (FIG. 14, panel C); and 600° C. (FIG. 14, panel D) of NiClL1 for 5 min. under a stream of 10% H$_2$/N$_2$. Inset: magnified image of the Ni nanoparticles, scale bar=100 nm.

FIGS. 15A-15D shows SEM images after RTP at 200° C. (FIG. 15, panel A); 300° C. (FIG. 15, panel B); 400° C. (FIG. 15, panel C); and 500° C. (FIG. 15, panel D) of NiClL1 on a silicon substrate for 5 min. under a stream of 10% H$_2$/N$_2$.

FIGS. 16A-16D shows RTP of NiClL1 for 5 min.—comparison of stability under a stream of 10% H$_2$/N$_2$ and in vacuum. SEM Images: (FIG. 16, panel A) 400° C., 10% H$_2$/N$_2$; (FIG. 16, panel B) 500° C., 10% H$_2$/N$_2$; (FIG. 16, panel C) 400° C., vacuum; (FIG. 16, panel D) 500° C., vacuum.

FIG. 17 shows TGA curve (continuous line) and temperature profile (dashed line) of NiClL1 from 30° C. to 1000° C.

FIGS. 22A-22B show SEM images of NiClL1 (dimensions: length: 2.6±0.9 µm, width: 1.4±0.5 µm, thickness: 250±50 nm); and FIG. 22C demonstrates histograms showing the size distribution of NiClL1. Reaction conditions: $NiCl_2$:L1=2:1, $DMF/CHCl_3$=3:1 v/v, 105° C., 5 days.

FIGS. 23A-23C shows topologies of nickel bromide containing microstructures obtained by solvothermal synthesis. FIG. 23, Panel A and FIG. 23, panel B show SEM images of NiBrL2. Dimensions: diagonal: 370±10 nm, side-to-side: 405±10 nm, thickness: 220±20 nm (FIG. 23, panel C). Reaction conditions: $NiBr_2$:L2=2:1, $DMF/CHCl_3$=3:1 v/v, 105° C., 5 days.

FIGS. 24A-24F shows the effect of variation in molar ratios of precursors (FIG. 24, panels A-B) and solvent (FIG. 24, panels C-F) on the structure of NiClL1. FIG. 24, Panel A and FIG. 24, panel B show SEM image of the microstructures obtained using 1:1 ratio of $NiCl_2$ to L1 and a magnified image thereof, respectively; reaction conditions: DMF solution (3.0 ml) of $NiCl_2.6H_2O$ (6.9 µmol), $CHCl_3$ solution (1.0 ml) of L1 (6.9 µmol), 105° C., 5 days, without stirring and with exclusion of light. FIG. 24, Panels C, D, E and F show SEM images of NiClL1 obtained using DMF: $CHCl_3$ 3:1 (v/v); DMF; DMF:$CHCl_3$ 2:1 (v/v); and DMF:$CHCl_3$ 3:1 (v/v)+0.5 ml $H_2O$, respectively; reaction conditions: DMF solution of $NiCl_2.6H_2O$ (13.8 µmol), $CHCl_3$ solution of L1 (6.9 µmol), 105° C., 5 days, without stirring and with exclusion of light.

FIGS. 25A-25D shows TEM images and SAED of the nickel containing microstructures. FIG. 25, Panel A—TEM image of NiClL1; FIG. 25, Panel B—high magnification TEM image showing lattice planes in a single crystal of NiClL1, inset: SAED pattern arising from NiClL1, scale bar=2 $nm^{-1}$, with d-spacing corresponding to 1:1.79 nm, 2:0.9 nm, 3:0.46 nm, 4:0.42 nm, 5:0.49 nm; FIG. 25, Panel C—TEM image of NiBrL2; and FIG. 25, Panel D—SAED pattern arising from NiBrL2, with d-spacing corresponding to 1′: 0.95 nm, 2′: 0.49 nm, 3′: 0.55 nm. For SAED, the crystal orientation (longest axis) is indicated by the yellow arrow in FIG. 25, panel A and FIG. 25, panel C.

FIG. 26 shows representative EDS of NiBrL2 using TEM (120 kV).

FIG. 27 shows representative $^1H$ NMR spectrum ($CDCl_3$) of the $CHCl_3$ extract after reacting CuBrL2 with conc. HCl and neutralizing with $Et_3N$. The spectrum corresponds to pure L2.

FIGS. 28A-28G shows RTP of NiClL1. FIG. 28, Panels A-E: RTP under 10% $H_2/N_2$ (inset scale bar=100 nm). FIG. 28, Panels F-G: RTP under vacuum. The experiments were done on NiClL1 drop-casted in silicon substrates, for 5 min.

FIGS. 29A-29F shows RTP of NiBrL2. FIG. 29, Panels A-C: RTP under 10% $H_2/N_2$ (inset scale bar=60 nm). FIG. 29, Panels D-F: RTP under vacuum. The experiments were done on NiBrL2 drop-casted in silicon substrates, for 5 min.

FIG. 30 shows SEM image of CuClL2. Reaction conditions: 1 eq. L2, 2 eq. $CuCl_2$, 3:1 (v/v) $DMF/CHCl_3$, 105° C., 5 days.

(FIG. 34A) Representative SEM image of $Cu(NO_3)L2$. (FIG. 34B) Histograms showing the size distribution of $Cu(NO_3)L2$. Length: 3.65±0.95 µm, breadth: 0.675±0.09 µm. Reaction conditions (using dry solvents, under nitrogen): $Cu(NO_3)_2$:L2=1:1, $DMF/CHCl_3$=3:1 v/v, 105° C., 5 days.

FIGS. 36A-36B shows effect of variations in solvent and temperature on the structure of $Cu(NO_3)L2$. SEM image of the structures obtained using $DMSO/CHCl_3$ (4 ml, 3:1 V/V) at 60° C. (FIG. 36, panel A); and $PhCN/CHCl_3$ (4 ml, 3:1 v/v) at 60° C. (FIG. 36, panel B). Reaction conditions: $Cu(NO_3)_2.3H_2O$ (3.3 mg, 13.6 µmol), $CHCl_3$ solution (1.0 ml) of L2 (5.0 mg, 6.8 µmol), 60° C., 5 days, without stirring and with exclusion of light. Similar structures were obtained at 105° C.

FIGS. 37A-37D shows effect of variations in solvent and temperature on the structure of CuBrL2. SEM image of the structures obtained using $PhCN/CHCl_3$ (4 ml, 3:1 v/v) at 60° C. (FIG. 37, panel A); $DMF/MeCN/CHCl_3$ (4 ml, 1.5:1.5:1 v/v/v) at 60° C. (FIG. 37, panel B); $MeCN/CHCl_3$ (4 ml, 3:1 v/v) at 60° C. (FIG. 37, panel C); and $DMSO/CHCl_3$ (4 ml, 3:1 v/v) at 60° C. (FIG. 37, panel D). Reaction conditions: CuBr (3 mg, 13.6 µmol), $CHCl_3$ solution (1.0 ml) of L2 (5.0 mg, 6.8 µmol), 60° C., 5 days, without stirring and with exclusion of light. Similar structures were obtained at 105° C.

FIGS. 38A-38F shows time dependent SEM analysis for the formation of Ni-based MOFs. NiClL1: Immediately upon mixing a DMF solution of $NiCl_2$ and a $CHCl_3$ solution of L1 at RT (FIG. 38, panel A); heating this mixture for 1 and 5 days at 105° C. (FIG. 38, panel B and FIG. 38, panel C, respectively). NiBrL2: Immediately upon mixing a DMF solution of $NiBr_2$ and a $CHCl_3$ solution of L2 at RT (FIG. 38, panel D); heating this mixture for 1 and 5 days at 105° C. (FIG. 38, panel E and FIG. 38, panel F, respectively). Scale bar: (panels A-C=2 µm; panels D-F=500 nm; inset panel D=200 nm).

FIGS. 39A-39E shows time dependent SEM analysis for the formation of CuBrL2. Topologies of CuBrL2 (FIG. 39, panels A-E; scale bar=5 μm) obtained after: (FIG. 39, panel A) immediately upon mixing a DMF solution of $CuBr_2$ and a $CHCl_3$ solution of L2 at RT. Inset scale bar=200 nm; (FIG. 39, panel B) heating this mixture for 1.5 days at 105° C. Inset scale bar=2 μm; (FIG. 39, panel C) heating the mixture for 2.5 days at 105° C. Inset scale bar=1 μm; (FIG. 39, panel D, and FIG. 39, panel D') heating the mixture for 3.5 days at 105° C. Inset scale bar=2 μm; and (FIG. 39, panel E) heating the mixture for 5 days at 105° C. Inset scale bar=2 μm.

FIGS. 40A-40D shows time dependent SEM analysis for the formation of $Cu(NO_3)L2$. Topologies of $Cu(NO_3)L2$ (FIG. 40, panels A-D; scale bar=5 μm) obtained after: (FIG. 40, panel A) heating a DMF solution of $Cu(NO_3)_2$ and a $CHCl_3$ solution of L2 for 1 day at 105° C. Inset: immediately after mixing $Cu(NO_3)_2$ and L2. Inset scale bar=200 nm; (FIG. 40. panel B) heating the mixture for 2.5 days at 105° C.; (FIG. 40, panel C) heating the mixture for 3.5 days at 105° C.; and (FIG. 40, panel D) heating the mixture for 5 days at 105° C.

FIGS. 43A-43B shows SEM and TEM images (FIG. 43, panel A and FIG. 43, panel B, respectively) of MOFs prepared from a $CHCl_3$ solution of L2 and a DMF solution of $NiCl_2.6H_2O$, under the conditions described in Study 3.

FIGS. 44A-44B shows MOFs prepared from a sonicated toluene solution of $Pd(COD)Cl_2$ and a toluene suspension of L2, under the conditions described in Study 3.

FIG. 47 shows MOFs prepared from a toluene solution of $Pd(PhCN)_2Cl_2$ and a heptane suspension of L2, under the conditions described in Study 3.

FIGS. 48A-48B show MOFs prepared from a $CHCl_3$ solution of L2 and a DMF solution of $Cu(OTf)_2$, under the conditions described in Study 3.

FIG. 49 shows MOFs prepared from a $CHCl_3$ solution of L2 and a DMF solution of $Cu(OTf)_2$, under the conditions described in Study 3.

FIGS. 50A-50B show MOFs prepared from a dry $CHCl_3$ solution of L2 and a dry DMF solution of $Cu(NO_3)_2.3H_2O$, under the conditions described in Study 3.

FIG. 51 shows MOFs prepared from a $CHCl_3$ solution of L2 and a DMF solution of $Zn(OAc)_2.2H_2O$, under the conditions described in Study 3.

FIGS. 52A-52B show MOFs prepared from a $CHCl_3$ solution of L2 and a DMF solution of $Zn(OAc)_2.2H_2O$, under the conditions described in Study 3.

FIGS. 57A-57D. FIG. 57, panel A illustrates SEM images of L4-NiBr. FIG. 57, panel B illustrates high-magnification TEM images of L4-NiBr with lattice planes having d-spacing of 1.79 nm (line markings) and an inset of FFT of the lattice planes. FIG. 57, panel C illustrates TEM image of L-NiBr. FIG. 57, panel D illustrates a histogram showing the size distribution of L-NiBr, having an average diagonal of 0.741 μm.

FIGS. 58A-58C. FIG. 58, panel A illustrates the SEM images of barrel-shaped morphologies of L4-NiBr. FIG. 58, panel B illustrates high-magnification TEM images of L4-NiBr with lattice planes and the top inset top diffraction pattern of L4-NiBr, and the bottom inset is a TEM image of L-NiBr. FIG. 58, panel C illustrates a histogram showing the size distribution of L4-NiBr, having a width 1.01 μm and a length of 2.49 μm.

FIGS. 59A-59C. FIG. 59, panel A illustrates STEM images of L-NiBr using High Angle Annular Dark Field (HAADF) of L4-NiBr topology. FIG. 59, panel B illustrates a single structure on which the elemental mapping was performed. FIG. 59, panel C illustrates the elemental mapping of L4-NiBr.

FIGS. 60A-60F. FIG. 60, panel A illustrates a time-dependent SEM analysis of the formation of an L-NiBr system immediately after mixing a DMF solution of $NiBr_2$ and a $CHCl_3$ solution of L4 at room temperature. FIG. 60, panel B, C, D, and E illustrate heating the mixture in FIG. 60, panel A for 2, 12, 24, and 42 h at 105° C., respectively. The scale bar in FIG. 60, panels A-E=2 μm. FIG. 60, panel F illustrates the Cl accumulation during the reaction, plotted as the Cl:Ni ratio vs. the reaction time.

FIGS. 61A-61B. FIG. 61, panel A illustrates SEM data of L4-$NiNO_3$ upon mixing of a DMF solution of $Ni(NO_3)_2$ and a $CHCl_3$ solution of L4 and is the image of the residue. FIG. 61, panel B illustrates an EDS done on the residue of FIG. 61, panel A. The Si peak belongs to the substrate on which the measurement is done.

FIGS. 62A-62C. FIG. 62, panel A illustrates an SEM image of the ellipsoid morphologies of L4-$NiNO_3$. FIG. 62, panel B illustrates a TEM image of the ellipsoid morphologies of L4-$NiNO_3$ and the inset is the SAED pattern arising from L4-$NiNO_3$ with d-spacing of 13 Å, indicated by the line. FIG. 62, panel C illustrates a histogram showing the size distribution of L4-$NiNO_3$ having a width: 1.13 μm and a length: 1.97 μm.

FIGS. 63A-63C. FIG. 63, panel A illustrates a SEM image of the hexagonal prism morphologies of L4-$CuNO_3$. FIG. 63, panel B illustrates a high-magnification TEM image showing lattice planes (using reduced FFT d distances were calculated to be 13.9 Å) and within the inset is a TEM image of L4-$CuNO_3$. FIG. 63, panel C illustrates a histogram showing the size distribution of L4-$CuNO_3$ having a hexagonal edge length of 1.68 μm, and a prism length of 4.83 μm.

FIGS. 64A-64F. FIG. 64, panel A illustrates a crystal structure of L4-$CuNO_3$ where the hydrogen atoms and solvent molecules were removed for clarity in ball and stick display. FIG. 64, panel B illustrates pores observed from the c-axis of FIG. 64, panel A. FIG. 64, panel C illustrates the pores from C axis origin, dark blue-inside the voids, and light blue outside the voids. FIG. 64, panel D illustrates the unit cell of L4-$CuNO_3$ with a space group of P622. FIG. 64, panel E illustrates the unit cell in space fills along the c-axis; the two sizes of pores are marked; A which takes 31%, 1228.6 Å³ and B 8%, 300 Å³. FIG. 64, panel F illustrates a SEM image of measured crystal.

FIGS. 65A-65F. FIG. 65, panel A illustrates drop-casting of the reaction mixture immediately upon mixing L4 and NiBr$_2$ and Ni(NO$_3$)$_2$ containing different amounts of anion where panel A has 100% NO$_3^-$. FIG. 65, panel B illustrates a reaction of 85% NO$_3^-$ and 15% Br$^-$. FIG. 65, panel C illustrates a reaction of 50% NO$_3^-$ and 50% Br$^-$. FIG. 65, panel D illustrates a reaction of 25% NO$_3^-$ and 75% Br$^-$. FIG. 65, panel E illustrates a reaction of 15% NO$_3^-$ and 85% Br$^-$. FIG. 65, panel F illustrates a reaction of 100% Br$^-$.

FIGS. 66A-66G. FIG. 66, panel A illustrates a SEM image of Ni containing MOFs with different anions derived from NiBr$_2$ and Ni(NO$_3$)$_2$, wherein 0% Br$^-$ and 100% NO$_3^-$. FIG. 66, panel B illustrates a SEM image of Ni containing MOFs with 85% NO$_3^-$, and 15% Br$^-$. FIG. 66, panel C illustrates a SEM image of Ni containing MOFs with 50% NO$_3^-$, and 50% Br$^-$. FIG. 66, panel D illustrates a SEM image of Ni containing MOFs with 25% NO$_3^-$, and 75% Br$^-$. FIG. 66, panel E illustrates a SEM image of Ni containing MOFs with 15% NO$_3^-$ and 85% Br$^-$. FIG. 66, panel F illustrates a SEM image of Ni containing MOFs with 0% NO$_3^-$ and 100% Br$^-$. The sale bar in panels A-F=10 µm. FIG. 66, panel G illustrates the structures' average size [length (first column) and width (second column)] vs. anion content.

FIGS. 67A-67G. FIG. 67, panel A illustrates the MOFs of drop-casting of the reaction mixture immediately upon mixing L4 and Cu(NO$_3$)$_2$ and Ni(NO$_3$)$_2$, wherein the mixture of metals was 100% Cu$^{2+}$. FIG. 67, panel B illustrates the MOFs of a metal mixture of 85% Cu$^{2+}$ and 15% Ni$^{2+}$. FIG. 67, panel C illustrates the MOFs of a metal mixture of 75% Cu$^{2+}$ and 25% Ni$^{2+}$. FIG. 67, panel D illustrates the MOFs of a metal mixture of 50% Cu$^{2+}$ and 50% Ni$^{2+}$. FIG. 67, panel E illustrates the MOFs of a metal mixture of 25% Cu$^{2+}$ and 75% Ni$^{2+}$. FIG. 67, panel F illustrates the MOFs of a metal mixture of 15% Cu$^{2+}$ and 85% Ni$^{2+}$. FIG. 67, panel G illustrates the MOFs of a metal mixture of 100% Ni$^{2+}$. The scale bar in panels A-G=1 µm.

FIGS. 68A-68I. FIG. 68, panel A illustrates a SEM image of L4 and Cu(NO$_3$)$_2$ and Ni(NO$_3$)$_2$ of 100% Cu$^{2+}$. FIG. 68, panel B illustrates a SEM image of a metal mixture of 85% Cu$^{2+}$ and 15% Ni$^{2+}$. FIG. 68, panel C illustrates a SEM image of a metal mixture of 75% Cu$^{2+}$ and 25% Ni$^{2+}$. FIG. 68, panel D illustrates a SEM image of a metal mixture of 50% Cu$^{2+}$ and 50% Ni$^{2+}$. FIG. 68, panel E illustrates a SEM image of a metal mixture of 25% Cu$^{2+}$ and 75% Ni$^{2+}$. FIG. 68, panel F illustrates a SEM image of a metal mixture of 15% Cu$^{2+}$ and 85% Ni$^{2+}$. FIG. 68, panel G illustrates a SEM image of a metal mixture of 100% Ni$^{2+}$. The scale bar in panels A-G=10 µm. FIG. 68, panel H illustrates the structures' size [length (first column) and edge length (second column)] vs. the Ni content. FIG. 68, panel I illustrates the amount of copper in each mixed metal MOF as measured by EDS (second column) compared to the amount used in the reaction (first column).

FIGS. 69A-69D. FIG. 69, panel A illustrates SEM images of L4-NiBr with no modification. FIG. 69, panel B illustrates SEM images of L4-NiBr with TOAB-capped AuNP. FIG. 69, panel C illustrates SEM images of L4-NiBr with TOAB-capped AuNP after heating to 150° C. for 6 h. FIG. 69, panel D illustrates SEM images of L4-NiBr with TOAB-capped AuNP after heating to 150° C. for 20 h. The scale bar in panels A-D=1 µm.

FIGS. 70A-70D. FIG. 70, panel A illustrates a SEM image of L4-NiNO$_3$. FIG. 70, panel B illustrates a SEM image of L4-NiNO$_3$ with TOAB-capped AuNP. FIG. 70, panel C illustrates a SEM image of L4-NiNO$_3$ with TOAB-capped AuNP after heating to 150° C. for 6 h. FIG. 70, panel C illustrates a SEM image of L4-NiNO$_3$ with TOAB-capped AuNP after heating to 150° C. for 20 h. The scale bar in FIG. 70, panels A-D=1 µm.

FIGS. 71A-71C. FIG. 71, panel A illustrates the distances between pyridine groups in Å for L4. FIG. 71, panel B illustrates the adamantane core size in Å. FIG. 71, panel C illustrates the angles of the carbon bonds comprising the adamantane core.

FIGS. 72A-72D. FIG. 72 in four panels illustrates the SEM images of the L3-Cu(NO$_3$) at the end of the cooling process (FIG. 72, panel A), after 1 hour (FIG. 72, panel B), after 2 hours (FIG. 72, panel C), and after four days (FIG. 72, panel D).

FIGS. 73A-73G. FIG. 73, panel A illustrates the SEM images of the L3-Cu(NO$_3$) at the end of the cooling process. FIG. 73, panel B illustrates the merged elongrated structures forming aggregates. FIG. 73, panel C illustrates a line of aggregates of elongated structures. FIG. 73, panel D illustrates cuboidal rods of L3-Cu(NO$_3$). FIG. 73, panel E illustrates shorten cuboidal rods of L3-Cu(NO$_3$). FIG. 73, panels F and G illustrate shorten cuboidal rods of L3-Cu(NO$_3$) after cooling.

FIGS. 74A-74E. FIG. 74, panel A illustrates the shape structure of L3-Cu(NO$_3$) that approximated perfect cylindrical geometry, deviating by slightly narrowing at the center of the cylinder body. FIG. 74, panel B illustrates the L3-Cu(NO$_3$) structure that possessed irregular protrusions on a cylinder base. (FIG. 74, panel B). FIG. 74, panel C illustrates the body cylinder defined by two external faces a small ring close to the base center formed and lines extended radially from the center, similar to petals from a pistil. FIG. 74, panel D illustrates "petal-like" regions in the initial cylindrical shape. FIG. 74, panel E illustrates the cylindrical shape resembling a perfectly sculpted dual daisies with twelve petals that were symmetrically attached from the back side FIGS. 75A-75F. FIG. 75, panel A illustrates the initial morphological transformation into a cylindrical shape and the red arrow indicates the contact point. FIG. 75, panel B illustrates the morphological transformation into a cylindrical shape and the red arrow indicates the contact point. FIG. 75, panel C illustrates the morphological transformation into a daisy-like shape and the red arrow indicates the contact point. FIG. 75, panel D illustrates the morphological transformation into a daisy-like shape and the red arrow indicates the contact point. FIG. 75, panel E illustrates the morphological transformation into a daisy-like shape and the red arrow indicates the contact point. FIG. 75, panel F illustrates the morphological transformation into a daisy-like shape with additional structures and the red arrow indicates the contact point.

FIGS. 76A-76E. FIG. 76, panel A illustrates an SEM image of elongated structures with a wide polydispersity. FIG. 76, panel B illustrates an SEM image of measurements showed elongated structures with a wide polydispersity in lengths. FIG. 76, panel C illustrates an SEM image of an elongated structure demonstrating that the circular cross sections are hollow. FIG. 76, panel D illustrates an SEM image of an elongated structure with a hollow circular cross section. FIG. 76, panel E illustrates an SEM image of an elongated structure with both hollow and solid morphologies in the rectangular cross action typology.

FIGS. 77A-77I. FIG. 77, panel A illustrates an SEM image of a CS obtained after solvotherm reaction. FIG. 77, panel B illustrates a SEM image of a CS with an undefined edge. FIG. 77, panel C illustrates an SEM image with an undefined edge. FIG. 77, panel D illustrates an SEM image of CS with an undefined edge. FIG. 77, panel E illustrates SEM and high-angle annular dark-field imaging S-TEM (HAADF) measurements of CSs that were hollow. FIG. 77, panel F illustrates an SEM image indicating the presence of spikes at the ends of the elongated structure and a longitudinal growth front following the plane direction that progresses separately for each plane within a layer. FIG. 77, panel G illustrates a TEM diffraction pattern indicating CS crystallinity. FIG. 77, panel H illustrates the TEM image highlighting the lattice plane orientation that constitute the faces of the CSs. FIG. 77, panel I illustrates the EDS measurements indicating the presence of copper in the cuboidal structures along with the elements constituting the ligand (carbon, nitrogen) and solvents (carbon, nitrogen, oxygen, chlorine).

FIGS. 78A-78H. FIG. 78, panel A illustrates an SEM image of the CS left to age for 3 hours. FIG. 78, panel B illustrates an SEM image of the CS left to age for 5 hours. FIG. 78, panel C illustrates an SEM image of the CS left to age for 10 hours. FIG. 78, panel D illustrates an SEM image of the CS left to age for 12 hours. FIG. 78, panel E illustrates an SEM image of the CS left to age for 15 hours. FIG. 78, panel F illustrates an SEM image of the CS left to age for 20 hours. FIG. 78, panel G illustrates the graphical representation of the numerical decrease of the CS MOF as a function of aging time. FIG. 78, panel H illustrates the graphical representation of the statistical decrease of the CS MOF as a function of aging time.

FIGS. 79A-79M. FIG. 79, panel A illustrates an SEM image of hierarchical aggregates (HAs) that are elongated cuboidal units arranged in different directions as 3D objects. FIG. 79, panel B illustrates an SEM image of a hierarchical aggregate after the sample was aged for 5 days. FIG. 79, panel C illustrates an SEM image of a hierarchical aggregate after the sample was aged for 10 days. FIG. 79, panel D illustrates an SEM image of a hierarchical aggregate after the sample was aged for 12 days. FIG. 79, panel E illustrates an SEM image of a hierarchical aggregate after the sample was aged for 15 days. FIG. 79, panel F illustrates an SEM image of a hierarchical aggregate after the sample was aged for 20 days. FIG. 79, panel G illustrates an SEM image of elongated unit where the hollow units are open at one extremity characterized by an uneven length at the end "spike-type." FIG. 79, panel H illustrates an SEM image where the external cross-section of the elongated units of the HA remained unchanged during the aging process. FIG. 79, panel I illustrates an SEM image of the end of the CS were evenly matched. FIG. 79, panel L illustrates an SEM image of a CS with the end sealed closed. FIG. 79, panel M illustrates an SEM image of a sealed end where non-symmetrical growth occurred on the sealed end as the elongation of the cuboid face formed spikes.

FIGS. 80A-80M. FIG. 80, panel A illustrates an SEM image illustrating the ongoing process where elongated units merged by coupling two CS units at the midpoint. FIG. 80, panel B illustrates an SEM image of an elongated unit where the CS coupling was partial. FIG. 80, panel C illustrates an SEM image of an elongated unit coupled with several CS units. FIG. 80, panel D illustrates an SEM image of an elongated unit coupled with several CS units. FIG. 80, panel E illustrates an SEM image of one HA junction. FIG. 80, panel F illustrates an SEM image of one HA junction at the end of the elongated unit. FIG. 80, panel G illustrates an SEM image of one HA junction at the end of an elongated unit. FIG. 80, panel H illustrates an SEM image of one HA junction with a multi-faceted junction. FIG. 80, panel I illustrates an TEM image of forming and formed HA junction showing the presence of superficial layers that extend continuously at the connection region of the units (red arrows). FIG. 80, panel L illustrates an SEM backscattered electron image presenting a brighter contrast to the junction area attributable to copper species. FIG. 80, panel M illustrates an SEM backscattered electron image presenting a brighter contrast at the junction area attributable to copper species.

FIGS. 81A-81B. FIG. 81, panel A illustrates an SEM image of the L3-Cu(NO$_3$) "rose-like" MOF. FIG. 81, panel B illustrates an SEM image of the L3-Cu(NO$_3$) "rose-like" MOF after solvothermal reaction.

DETAILED DESCRIPTION OF THE INVENTION

Figure 1A:
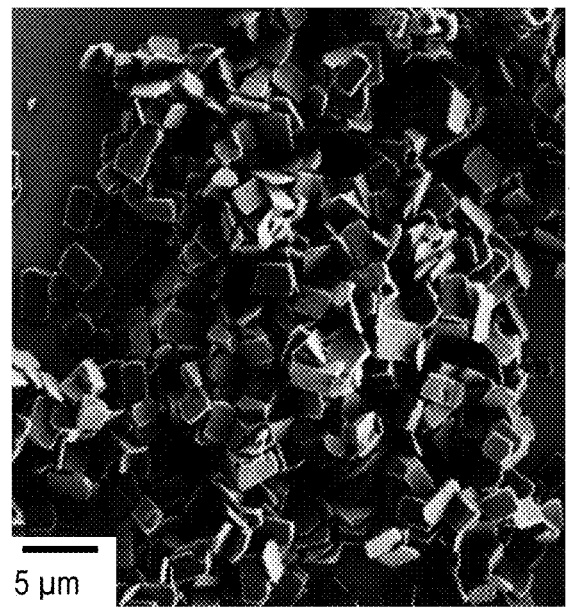
FIGS. 1A-1B show (FIG. 1A) SEM image of the brick-like microstructures (NiClL1)

In one aspect, the present invention provides a metal-organic material as defined above, i.e., a metal-organic material comprising at least two ligands each of the general formula I as defined above, at least two metal ions structurally coordinated with said ligands, and counter anions.

It has been found, in accordance with the present invention, that metal-organic materials, in particular such materials comprising tetrahedral polypyridyl ligands and transition metal ions coordinated therewith, having diverse three-dimensional (sub)-microstructures with a high degree of uniformity, can be prepared by a particular solvothermal synthesis, while controlling the uniformity and topology of said microstructures without the addition of any surfactants or modulators.

In one aspect, the present invention thus provides a metal-organic material comprising at least two ligands, at least two metal ions structurally coordinated with said ligands, and counter anions, wherein each one of the ligands is of the general formula I:

$$R_1(R_2\text{-}R_3\text{-}R_4)_4, \qquad I$$

wherein
$R_1$ is C, i.e.,

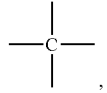

or adamantane-1,3,5,7-tetrayl, i.e.,

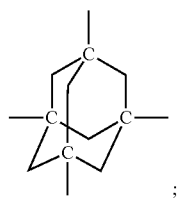

$R_2$ and $R_3$ each independently is absent, or selected from $(C_1\text{-}C_8)$alkylene, $(C_2\text{-}C_8)$alkenylene, $(C_2\text{-}C_8)$alkynylene, cycloalkylene, heterocycloalkylene, arylene-diyl, heteroarylene-diyl, or —N=N—, wherein said alkylene, alkenylene, alkynylene, cycloalkylene, heterocycloalkylene, arylene-diyl and heteroarylene-diyl may optionally be substituted with one or more groups each independently selected from halogen, —OR$_6$, —CN, —COR$_6$, —COOR$_6$, —CON(R$_6$)$_2$, —OCOOR$_6$, —OCON(R$_6$)$_2$, —(C$_1$-C$_4$)alkyl, —O—(C$_1$-C$_4$)alkyl, —(C$_1$-C$_4$)alkylene-COOR$_6$, —N(R$_6$)$_2$, —NO$_2$, —SR$_6$, —SO$_2$R$_6$, or —S(═O)R$_6$, or said alkylene, alkenylene and alkynylene may optionally be interrupted by one or more identical or different heteroatoms selected from S, O or N, and/or at least one group selected from —N═N—, —NH—CO—, —CO—NH—, —N(C$_1$-C$_4$alkyl)-, —N(C$_6$-C$_{10}$aryl)-, or —(C$_6$-C$_{10}$)arylene-diyl-, wherein R$_6$ each independently is H, (C$_1$-C$_4$)alkyl, (C$_2$-C$_4$)alkenyl or (C$_2$-C$_4$)alkynyl;

R$_4$ each independently is a pyridyl of the formula II, 2,2'-bipyridyl of the formula III, or 2,2':6',2''-terpyridyl of the formula IV, linked through a carbon atom thereof; and

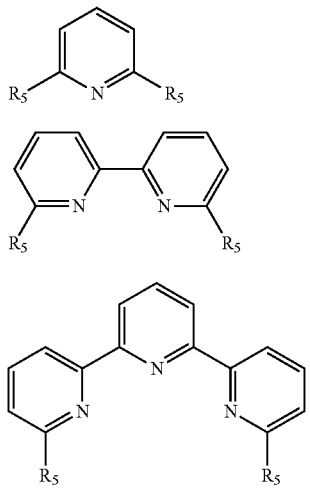

R$_5$ each independently is H, —COOH, —CN, —OH, or —NH$_2$.

In another aspect, the present invention relates to a method for the preparation of a metal-organic material as defined above, comprising the steps of:
(i) providing (a) an organic solution or suspension of a metal salt consisting of anions and said metal ions; and (b) an organic solution or suspension of said ligands, in a pressure vessel, e.g., a glass pressure vessel;
(ii) sealing and keeping said pressure vessel for a period of time with exclusion of light and without stirring, optionally while heating to a temperature ranging from 60° C. to 120° C. for the whole said period of time or a part thereof and then gradually cooling, thereby reacting said metal ions with said ligands to obtain said metal-organic material as a precipitate; and
(iii) collecting said precipitate.

In yet another aspect, the present invention relates to use of a metal-organic material as defined above as an adsorbent in a process for gas adsorption or gas separation.

In still another aspect, the present invention relates to a process for gas adsorption or gas separation by adsorbing said gas to an adsorbent, the improvement wherein said adsorbent is a metal-organic material as defined above.

The term "metal-organic material" or "metal-organic framework (MOF)" as used herein refers to a particular type of a coordination polymer, more specifically an metal-organic polymer, containing metal cations, preferably transition metal cations, coordinated to organic ligands each of the general formula I to form one-, two-, or three-dimensional structures that can be porous, wherein the choice of metal cation and organic ligand dictates the structure and hence the properties of the MOF. More particularly, the MOF is a coordination network with organic ligands containing potential voids, wherein the term "coordination network" refers to a coordination oligomer extending, through repeating coordination entities, either in one dimension but with cross-links between two or more individual chains, loops, or spiro-links, or in two or three dimensions (see also Biradha et al., 2009).

The term "halogen", as used herein, includes fluoro, chloro, bromo, and iodo.

The term "alkane", as used herein, refers to a straight or branched, or cyclic (including polycyclic), saturated hydrocarbon having preferably 5-14, carbon atoms, and includes, e.g., pentane, hexane, cyclohexane, heptane, cycloheptane, octane, cyclooctane, nonane, decane, decalin, and the like.

The term "alkanol", as used herein, refers to an alkane having preferably 1-10 carbon atoms and containing a hydroxy/alcohol functional group (—OH) in place of a hydrogen atom, and includes, e.g., methanol, ethanol, isopropanol, n-butanol, sec-butanol, isobutanol, pentanol, hexanol, and the like.

The term "alkyl", as used herein, typically means a straight or branched hydrocarbon radical having preferably 1-8, more preferably 1-4, carbon atoms, and includes, e.g., methyl, ethyl, n-propyl, isopropyl, n-butyl, isobutyl, sec-butyl, tert-butyl, n-pentyl, isopentyl, 2,2-dimethylpropyl, n-hexyl, n-heptyl, n-octyl, and the like.

The term "alkylene", as used herein, refers to a linear divalent hydrocarbon chain having preferably 1-8 carbon atoms and includes, e.g., methylene, ethylene, propylene, butylene, pentylene, hexylene, heptylene, octylene, and the like. The terms "alkenylene" and "alkynylene" typically mean linear divalent hydrocarbon radicals having preferably 2-8 carbon atoms and at least one double or triple bond, respectively. Non-limiting examples of such alkenylenes include ethenylene, 1,3-propenylene, 1,4-but-1-enylene, 1,4-but-2-enylene, 1,4-but-3-enylene, 1,5-pent-1-enylene, 1,5-pent-2-enylene, 1,5-pent-3-enylene, 1,5-pent-4-enylene, 1,6-hex-1-enylene, 1,6-hex-2-enylene, 1,6-hex-3-enylene, 1,6-hex-4-enylene, 1,6-hex-5-enylene, 1,7-hept-1-enylene, 1,7-hept-2-enylene, 1, 7-hept-3-enylene, 1,7-hept-4-enylene, 1,7-hept-5-enylene, 1,7-hept-6-enylene, 1,8-oct-1-enylene, 1,8-oct-2-enylene, 1,8-oct-2-enylene, 1,8-oct-3-enylene, 1,8-oct-4-enylene, 1,8-oct-5-enylene, 1,8-oct-6-enylene, 1,8-oct-7-enylene, and the like; and examples of such alkynylenes include, without limiting, ethynylene, 1,3-propynylene, 1,4-but-1-ynylene, 1,4-but-2-ynylene, 1,4-but-3-ynylene, 1,5-pent-1-ynylene, 1,5-pent-2-ynylene, 1,5-pent-3-ynylene, 1,5-pent-4-ynylene, 1,6-hex-1-ynylene, 1,6-hex-2-ynylene, 1,6-hex-3-ynylene, 1,6-hex-4-ynylene, 1,6-hex-5-ynylene, 1,7-hept-1-ynylene, 1,7-hept-2-ynylene, 1,7-hept-3-ynylene, 1,7-hept-4-ynylene, 1,7-hept-5-ynylene, 1,7-hept-6-ynylene, 1,8-oct-1-ynylene, 1,8-oct-2-ynylene, 1,8-oct-2-ynylene, 1,8-oct-3-ynylene, 1,8-oct-4-ynylene, 1,8-oct-5-ynylene, 1,8-oct-6-ynylene, 1,8-oct-7-ynylene, and the like.

The term "cycloalkylene", as used herein, typically means a mono- or bicyclic saturated divalent hydrocarbon radical having preferably 3-10 carbon atoms such as cyclopropylene, cyclobutylene, cyclopentylene, cyclohexylene, cycloheptylene, cyclooctylene, cyclodecylene, bicyclo[3.2.1]octane-diyl, bicyclo[2.2.1]heptane-diyl, and the like. The term "heterocycloalkylene" refers to a cycloalkylene, in which at least one of the ring carbon atoms is replaced by a heteroatom selected from N, O or S.

The term "aryl", as used herein, denotes an aromatic carbocyclic group, preferably having 6-14 carbon atoms, consisting of a single ring or multiple rings either condensed or linked by a covalent bond such as, but not limited to, phenyl, naphthyl, phenanthryl, and biphenyl. The term "arylene-diyl" refers to a divalent group derived from an arene by removal of a hydrogen atom from two ring carbon atoms. Non-limiting examples of arylene-diyls include benzene-1,3-diyl, benzene-1,4-diyl, naphthalene-diyl, phenanthrene-2,7-diyl, biphenyl-4,4'-diyl, and the like.

The term "heteroarylene-diyl" refers to a divalent group derived from a mono- or polycyclic heteroaromatic ring containing one to three, preferably 1-2, heteroatoms selected from the group consisting of N, O and S, by removal of a hydrogen atom from two ring atoms. When the heteroarylene-diyl is a monocyclic heteroaromatic ring, it is preferably a divalent group of a 5-6-membered ring such as, but not limited to, pyrrole-2,5-diyl, pyrrole-3,5-diyl, furane-2,5-diyl, furane-3,5-diyl, thiophene-2,5-diyl, thiophene-3,5-diyl, thiazine-2,5-diyl, thiazine-3,6-diyl, pyrazole-1,3-diyl, pyrazole-1,4-diyl, pyrazole-3,5-diyl, pyrazine-2,5-diyl, pyrazine-2,6-diyl, imidazole-1,4-diyl, imidazole-2,4-diyl, imidazole-2,5-diyl, oxazole-2,4-diyl, oxazole-2,5-diyl, isoxazole-3,5-diyl, thiazole-2,4-diyl, thiazole-2,5-diyl, isothiazole-3,5-diyl, pyridine-2,4-diyl, pyridine-3,6-diyl, pyrimidine-2,4-diyl, pyrimidine-2,5-diyl, 1,2,3-triazine-4,6-diyl, 1,3,4-triazine-2,5-diyl, 1,3,4-triazine-2,6-diyl, 1,3,5-triazine-2,4-diyl, and the like. Examples of polycyclic heteroarylene-diyls composed of two rings include, without being limited to, benzofurane-2,5-diyl, benzofurane-2,6-diyl, isobenzofurane-2,4-diyl, isobenzofurane-2,5-diyl, benzothiene-2,5-diyl, benzothiene-2,6-diyl, indole-2,5-diyl, indole-2,6-diyl, quinoline-2,6-diyl, quinoline-2,7-diyl, quinoline-3,6-diyl, quinoline-3,7-diyl, isoquinoline-3,6-diyl, isoquinoline-3,7-diyl, imidazo[1,2-a]pyridine-2,6-diyl, imidazo[1,2-a]pyridine-2,7-diyl, benzimidazole-2,5-diyl, benzimidazole-2,6-diyl, benzthiazole-2,5-diyl, benzthiazole-2,6-diyl, benzoxazole-2,5-diyl, benzoxazole-2,6-diyl, pyrido[1,2-a]pyrimidine-2,7-diyl, pyrido[1,2-a]pyrimidine-2,8-diyl, pyrido[1,2-a]pyrimidine-3,7-diyl, pyrido[1,2-a]pyrimidine-3,7-diyl, 1,3-benzodioxin-2,6-diyl, 1,3-benzodioxin-2,7-diyl, and the like.

The alkylene, alkenylene, alkynylene, cycloalkylene, heterocycloalkylene, arylene-diyl and heteroarylene-diyl may optionally be substituted with one or more groups each independently selected from halogen, —$OR_6$, —CN, —$COR_6$, —$COOR_6$, —$CON(R_6)_2$, —$OCOOR_6$, —$OCON(R_6)_2$, —$(C_1$-$C_4)$alkyl, —O—$(C_1$-$C_4)$alkyl, —$(C_1$-$C_4)$alkylene-$COOR_6$, —$N(R_6)_2$, —$NO_2$, —$SR_6$, —$SO_2R_6$, or —S(=O)$R_6$, or said alkylene, alkenylene and alkynylene may optionally be interrupted by one or more, e.g., one or two, identical or different heteroatoms selected from S, O or N, and/or at least one group, e.g., one, two or three groups, each independently selected from —N=N—, —NH—CO—, —CO—NH—, —$N(C_1$-$C_4$alkyl)-, —$N(C_6$-$C_{10}$aryl)-, or —$(C_6$-$C_{10})$arylene-diyl-, wherein $R_6$ each independently is H, $(C_1$-$C_4)$alkyl, $(C_2$-$C_4)$alkenyl or $(C_2$-$C_4)$alkynyl.

In certain embodiments, the metal-organic material of the present invention is a material of the general formula I as defined above, wherein $R_2$ and $R_3$ each independently is absent, or selected from $(C_1$-$C_8)$alkylene, $(C_2$-$C_8)$alkenylene, $(C_2$-$C_8)$alkynylene, cycloalkylene, heterocycloalkylene, arylene-diyl, heteroarylene-diyl, or —N=N—, wherein said alkylene, alkenylene, alkynylene, cycloalkylene, heterocycloalkylene, arylene-diyl and heteroarylene-diyl may optionally be substituted with one or more groups each independently selected from halogen, —$OR_6$, —CN, —$COR_6$, —$COOR_6$, —$CON(R_6)_2$, —$OCOOR_6$, —$OCON(R_6)_2$, —$(C_1$-$C_4)$alkyl, —O—$(C_1$-$C_4)$alkyl, —$(C_1$-$C_4)$alkylene-$COOR_6$, —$N(R_6)_2$, —$NO_2$, —$SR_6$, —$SO_2R_6$, or —S(=O)$R_6$, wherein $R_6$ is H, or said alkylene, alkenylene and alkynylene may optionally be interrupted by one or more identical or different heteroatoms selected from S, O or N, and/or at least one group selected from —N=N—, —NH—CO—, —CO—NH—, —$N(C_1$-$C_4$alkyl)-, —$N(C_6$-$C_{10}$aryl)-, or —$(C_6$-$C_{10})$arylene-diyl-.

In certain particular such embodiments, $R_2$ and $R_3$ each independently is absent, or selected from $(C_1$-$C_4)$alkylene, $(C_2$-$C_4)$alkenylene, $(C_2$-$C_4)$alkynylene, cycloalkylene, heterocycloalkylene, arylene-diyl, heteroarylene-diyl, or —N=N—, wherein said alkylene, alkenylene, alkynylene, cycloalkylene, heterocycloalkylene, arylene-diyl and heteroarylene-diyl may optionally be substituted with halogen, —OH, —CN, —COH, —COOH, —$CONH_2$, —OCOOH, —$OCONH_2$, —$(C_1$-$C_2)$alkyl, —O—$(C_1$-$C_2)$alkyl, —$(C_1$-$C_2)$alkylene-COOH, —$NH_2$, —$NO_2$, —SH, —$SO_2$H, or —S(=O)H, or said alkylene, alkenylene and alkynylene may optionally be interrupted by one or more identical or different heteroatoms selected from S, O or N, and/or at least one group selected from —N=N—, —NH—CO—, —CO—NH—, —$N(C_1$-$C_2$alkyl)-, —$N(C_6$aryl)-, or —$(C_6)$arylene-diyl-.

In more particular such embodiments, the metal-organic material of the present invention is a material of the general formula I, wherein $R_2$ and $R_3$ each independently is absent, or selected from $(C_1$-$C_4)$alkylene, $(C_2$-$C_4)$alkenylene, $(C_2$-$C_4)$alkynylene, arylene-diyl, or heteroarylene-diyl, e.g., wherein (i) one of $R_2$ and $R_3$ is absent and another of $R_2$ and $R_3$ is $(C_2$-$C_4)$alkylene, $(C_2$-$C_4)$alkenylene, $(C_2$-$C_4)$alkynylene, arylene-diyl, or heteroarylene-diyl; (ii) one of $R_2$ and $R_3$ is $(C_2$-$C_4)$alkylene, $(C_2$-$C_4)$alkenylene or $(C_2$-$C_4)$alkynylene, and another of $R_2$ and $R_3$ is arylene-diyl, or heteroarylene-diyl; or (iii) both $R_2$ and $R_3$ are absent. Certain specific such embodiments are those wherein $R_2$ is $(C_2$-$C_4)$alkenylene or $(C_2$-$C_4)$alkynylene, and $R_3$ is $(C_6)$arylene-diyl; or $R_2$ is $(C_6)$arylene-diyl, and $R_3$ is $(C_2$-$C_4)$alkenylene or $(C_2$-$C_4)$alkynylene.

In certain embodiments, the metal-organic material of the present invention is a material of the general formula I as defined above, wherein $R_4$ each independently is a pyridyl of the formula II, wherein $R_5$ each independently is H, —COOH, —CN, —OH, or —$NH_2$, preferably H or —COOH.

In certain embodiments, the metal-organic material of the present invention is a material of the general formula I as defined above, wherein $R_1$ is C or adamantane-1,3,5,7-tetrayl; $R_2$ and $R_3$ each independently is absent, or selected from $(C_1$-$C_4)$alkylene, $(C_2$-$C_4)$alkenylene, $(C_2$-$C_4)$alkynylene, cycloalkylene, heterocycloalkylene, arylene-diyl, heteroarylene-diyl, or —N=N—, wherein said alkylene, alkenylene, alkynylene, cycloalkylene, heterocycloalkylene, arylene-diyl and heteroarylene-diyl may optionally be substituted with one or more groups each independently selected from halogen, —$OR_6$, —CN, —$COR_6$, —$COOR_6$, —$CON(R_6)_2$, —$OCOOR_6$, —$OCON(R_6)_2$, —$(C_1$-$C_4)$alkyl, —O—$(C_1$-$C_4)$alkyl, —$(C_1$-$C_4)$alkylene-$COOR_6$, —$N(R_6)_2$, —$NO_2$, —$SR_6$, —$SO_2R_6$, or —S(=O)$R_6$, wherein $R_6$ is H, or said alkylene, alkenylene and alkynylene may optionally be interrupted by one or more identical or different heteroatoms selected from S, O or N, and/or at least one group selected from —N=N—, —NH—CO—, —CO—NH—, —$N(C_1$-$C_2$alkyl)-, —$N(C_6$aryl)-, or —$(C_6)$arylene-diyl-; $R_4$ each independently is pyridyl of the formula II; and $R_5$ each independently is H, —COOH, —CN, —OH, or —NH$_2$, preferably H or —COOH.

In certain particular such embodiments, $R_2$ and $R_3$ each independently is absent, or selected from $(C_1-C_4)$alkylene, $(C_2-C_4)$alkenylene, $(C_2-C_4)$alkynylene, arylene-diyl, or heteroarylene-diyl; $R_4$ is a pyridyl of the formula II linked through the carbon atom para to the nitrogen atom; and $R_5$ is H or —COOH. In more particular such embodiments, the metal-organic material of the present invention is a material of the general formula I, wherein (i) one of $R_2$ and $R_3$ is absent and another of $R_2$ and $R_3$ is $(C_2-C_4)$alkylene, $(C_2-C_4)$alkenylene, $(C_2-C_4)$alkynylene, arylene-diyl, or heteroarylene-diyl; (ii) one of $R_2$ and $R_3$ is $(C_2-C_4)$alkylene, $(C_2-C_4)$alkenylene or $(C_2-C_4)$alkynylene, and another of $R_2$ and $R_3$ is arylene-diyl, or heteroarylene-diyl; or (iii) both $R_2$ and $R_3$ are absent, e.g., wherein $R_2$ is $(C_2-C_4)$alkenylene or $(C_2-C_4)$alkynylene, and $R_3$ is $(C_6)$arylene-diyl; or $R_2$ is $(C_6)$arylene-diyl, and $R_3$ is $(C_2-C_4)$alkenylene or $(C_2-C_4)$alkynylene. Certain specific such embodiments are those wherein $R_2$ is $(C_6)$arylene-diyl; and $R_3$ is $(C_2)$alkenylene or $(C_2)$alkynylene, i.e., metal-organic materials comprising at least two metal ions structurally coordinated with at least two polypyridyl ligands each of the general formula I, consisting of C or adamantane-1,3,5,7-tetrayl linked to four identical "arms" each being (4-(2-(pyridin-4-yl)vinyl)phenyl) or (4-(pyridin-4-ylethynyl) phenyl), respectively.

In specific embodiments, the metal-organic material of the present invention is a material of the general formula I, wherein (i) $R_1$ is C, and each one of said ligands is tetrakis (4-(pyridin-4-ylethynyl)phenyl)methane or tetrakis(4-(2-(pyridin-4-yl)vinyl) phenyl)methane, herein identified ligands L1 and L2, respectively; or (ii) $R_1$ is adamantane-1,3,5,7-tetrayl, and each one of said ligands is 1,3,5,7-tetrakis(4-(pyridin-4-ylethynyl)phenyl)adamantane or 1,3,5,7-tetrakis(4-(2-(pyridin-4-yl)vinyl)phenyl) adamantane, herein identified ligands L3 and L4, respectively (see Appendix).

In certain embodiments, the metal ions comprised within the metal-organic material of the present invention are ions of a transition metal such as Os, Ru, Fe, Pt, Pd, Ni, Ir, Rh, Zn, Co, Cu, Re, Tc, Mn, V, Nb, Ta, Hf, Zr, Cr, Mo, W, Ti, Sc, Ag, Au, Y, or a combination thereof. In particular such embodiments, the metal ions are ions of one or more, i.e., a combination, of Ni, Cu, Pd or Zn.

In certain embodiments, the counter anions comprised within the metal-organic material of the present invention are selected from inorganic anions, organic anions, or a combination thereof. Examples of inorganic anions include, without being limited to, F$^-$, Cl$^-$, Br$^-$, I$^-$, NO$_3^-$, PF$_6^-$, BF$_4^-$, OH$^-$, ClO$_4^-$, SO$_3^-$, and CN$^-$; and non-limiting examples of organic anions include alkylCOO$^-$, preferably acetoxy (OAc), CF$_3$COO$^-$, arylCOO$^-$, trifluoromethanesulfonate (triflate, OTf).

As defined above, the metal-organic material of the present invention is a particular type of a coordination polymer containing metal ions, preferably transition metal ions, coordinated to organic ligands each of the general formula I to form one-, two-, or three-dimensional structures. In certain embodiments, the metal-organic material of the present invention comprises at least one of metal ion structurally coordinated between at least two ligands. The material may have a metal ion to ligand ratio of 1:10, preferably 1:2 to 1:6, and more preferably a metal ion to ligand ratio of 1:2 to 1:4, as determined by stoichiometric equivalents.

In certain embodiments, the metal-organic material of the present invention comprises metal ions coordinated to organic ligands each of the general formula I to form a three-dimensional (3D) structure. In particular such embodiments, the metal-organic material of the invention has a 3D crystalline micro or sub-micro structure, more particularly wherein said crystalline micro or sub-micro structure has a geometrical shape, e.g., a brick-like microstructure. Examples of 3D crystalline geometric shape include, without being limited to, hexagonal, spherical, stella-octangula, and flower-like shape.

MOFs having 3D structures in general and such MOFs according to the present invention in particular, are porous and may thus further comprise solvent molecules, also referred to as "guest molecules", left from the preparation process and confined within the pores of the 3D structure. As the pores of the MOFs are stable during elimination of those solvent molecules, such MOFs can be used as adsorbents in processes for gas adsorption, e.g., H$_2$, CO, CO$_2$ or methane adsorption, or gas separation and/or purification, e.g., separation of CO$_2$ from methane.

In one specific embodiment, the metal-organic material of the invention comprises ligands each being ligand L1, Ni(II) ions structurally coordinated with nitrogen atoms of said ligands, and Cl$^-$ as counter anions, wherein said metal-organic material has the chemical formula $(NiCl_2N_2C_{26.5}H_{16})_n$, wherein n is an integer of at least 4, and a 3D crystalline micro or sub-micro structure optionally further comprising solvent molecules. This material is herein identified NiClL1 and may be formed, e.g., by adding a chloroform solution of L1 to a dimethylformamide (DMF) suspension of NiCl$_2$.6H$_2$O in an oven-dried glass pressure tube, which is then sealed; heated for 5 days at 105° C. without stirring and with exclusion of light; and then gradually cooled to RT over 9-10 h. to thereby obtain NiClL1 as a light green precipitate having the geometrical shape of an elongated hexagons (brick-like). The NiClL1 crystalline structures obtained may further comprise chloroform and/or DMF molecules confined within the structural pores.

In another specific embodiment, the metal-organic material of the invention comprises ligands each being ligand L1, Ni(II) ions structurally coordinated with nitrogen atoms of said ligands, and Br$^-$ as counter anions, wherein said metal-organic material has the chemical formula $(NiBr_2N_2C_{26.5}H_{16})_n$, wherein n is an integer of at least 4, and a 3D crystalline micro or sub-micro structure optionally further comprising solvent molecules. This material is herein identified NiBrL1 and may be formed, e.g., by adding a chloroform solution of L1 to a DMF suspension of NiBr$_2$ in an oven-dried glass pressure tube, which is then sealed; heated for 5 days at 105° C. without stirring and with exclusion of light; and then gradually cooled to RT over 9-10 h. to thereby obtain NiBrL1 as a light green precipitate. The NiBrL1 crystalline structures obtained may further comprise chloroform and/or DMF molecules confined within the structural pores.

In still another specific embodiment, the metal-organic material of the invention comprises ligands each being ligand L2, Ni(II) ions structurally coordinated with nitrogen atoms of said ligands, and Cl$^-$ as counter anions, wherein said metal-organic material has the chemical formula $(NiCl_2N_2C_{26.5}H_{20})_n$, wherein n is an integer of at least 4, and a 3D crystalline micro or sub-micro structure optionally further comprising solvent molecules. This material is herein identified NiClL2 and may be formed, e.g., by carefully layering a chloroform solution of L2 below a DMF solution of NiCl$_2$.6H$_2$O in an oven-dried glass tube, which is then sealed and kept in the dark for 5 days, to thereby obtain NiClL2 as a light green precipitate. The NiClL2 crystalline structures obtained may further comprise chloroform and/or DMF molecules confined within the structural pores.

In yet another specific embodiment, the metal-organic material of the invention comprises ligands each being ligand L2, Ni(II) ions structurally coordinated with nitrogen atoms of said ligands, and Br$^-$ as counter anions, wherein said metal-organic material has the chemical formula $(NiBr_2N_2C_{26.5}H_{20})_n$ wherein n is an integer of at least 4, and a 3D crystalline micro or sub-micro structure optionally further comprising solvent molecules. This material is herein identified NiBrL2 and may be formed, e.g., by adding a chloroform solution of L2 to a DMF solution of $NiBr_2$ in a glass pressure tube, which is then sealed; heated for 5 days at 105° C. without stirring and with exclusion of light; and then gradually cooled to RT over 9-10 h. to thereby obtain NiBrL2 as a light green precipitate having the geometrical shape of near-regular hexagons. The NiBrL2 crystalline structures obtained may further comprise chloroform and/or DMF molecules confined within the structural pores.

In another specific embodiment, the metal-organic material of the invention comprises ligands each being ligand L2, Cu(II) ions structurally coordinated with nitrogen atoms of said ligands, and Cl$^-$ as counter anions, wherein said metal-organic material has the chemical formula $(CuCl_2N_2C_{26.5}H_{20})_n$, wherein n is an integer of at least 4, and a 3D crystalline micro or sub-micro structure optionally further comprising solvent molecules. This material is herein identified CuClL2 and may be formed, e.g., by adding a chloroform solution of L2 to a DMF solution of $CuCl_2$ in a glass pressure tube, which is then sealed; heated for 5 days at 105° C. without stirring and with exclusion of light; and then gradually cooled to RT over 9-10 h. to thereby obtain CuClL2 as a dark green precipitate. The CuClL2 crystalline structures obtained may further comprise chloroform and/or DMF molecules confined within the structural pores.

In still another specific embodiment, the metal-organic material of the invention comprises ligands each being ligand L2, Cu(II) ions structurally coordinated with nitrogen atoms of said ligands, and Br$^-$ as counter anions, wherein said metal-organic material has the chemical formula $(CuBr_2N_2C_{26.5}H_{20})_n$, wherein n is an integer of at least 4, and a 3D crystalline micro or sub-micro structure optionally further comprising solvent molecules. This material is herein identified CuBrL2 and may be formed, e.g., by adding a chloroform solution of L2 to a DMF solution of $CuBr_2$ in a glass pressure tube, which is then sealed; heated for 5 days at 105° C. without stirring and with exclusion of light; and then gradually cooled to RT over 9-10 h. to thereby obtain CuBrL2 as a dark green precipitate having the geometrical shape of stella-octangula. The CuBrL2 crystalline structures obtained may further comprise chloroform and/or DMF molecules confined within the structural pores.

In yet another specific embodiment, the metal-organic material of the invention comprises ligands each being ligand L2, Cu(II) ions structurally coordinated with nitrogen atoms of said ligands, and $NO_3^-$ as counter anions, wherein said metal-organic material has the chemical formula $(Cu(NO_3)_2N_2C_{26.5}H_{20})_n$ wherein n is an integer of at least 4, and a 3D crystalline micro or sub-micro structure optionally further comprising solvent molecules. This material is herein identified $Cu(NO_3)_2$L2 and may be formed, e.g., by adding a chloroform solution of L2 to a DMF solution of $Cu(NO_3)_2$ in a glass pressure tube, which is then sealed; heated for 5 days at 105° C. without stirring and with exclusion of light; and then gradually cooled to RT over 9-10 h. to thereby obtain $Cu(NO_3)_2$L2 as a dark green precipitate. Alternatively, $Cu(NO_3)_2$L2 may be formed by adding a dry chloroform solution of L2 to a dry DMF solution of $Cu(NO_3)_2 \cdot 3H_2O$ under $N_2$ atmosphere in an oven-dried glass pressure tube, which is then sealed; heated for 6 days at 105° C. without stirring and with exclusion of light; and then gradually cooled to RT over 9-10 h. to thereby obtain $Cu(NO_3)_2$L2 as a light green precipitate having the geometrical shape of rectangular prisms. The $Cu(NO_3)_2$L2 crystalline structures obtained may further comprise chloroform and/or DMF molecules confined within the structural pores.

In another specific embodiment, the metal-organic material of the invention comprises ligands each being ligand L2, Cu(II) ions structurally coordinated with nitrogen atoms of said ligands, and OTf as counter anions, wherein said metal-organic material has the chemical formula $(Cu(OTf)_2N_2C_{26.5}H_{20})_n$, wherein n is an integer of at least 4, and a 3D crystalline micro or sub-micro structure optionally further comprising solvent molecules. This material is herein identified $Cu(OTf)_2$L2 and may be formed, e.g., by carefully layering a chloroform solution of L2 below a DMF solution of $Cu(OTf)_2$ in an oven-dried glass tube, which is then sealed and kept in the dark for 5 days, to thereby obtain $Cu(OTf)_2$L2 as a light blue precipitate. Alternatively, $Cu(OTf)_2$L2 may be formed by carefully layering a chloroform solution of L2 below a DMF solution of $Cu(OTf)_2$ in an oven-dried glass tube, which is then sealed and kept in the dark for 10 days; heated for another 2 days at 60° C. without stirring and with exclusion of light; and then gradually cooled to RT to thereby obtain $Cu(OTf)_2$L2 as a light blue precipitate. The $Cu(OTf)_2$L2 crystalline structures obtained may further comprise chloroform and/or DMF molecules confined within the structural pores.

In still another specific embodiment, the metal-organic material of the invention comprises ligands each being ligand L2, Pd(II) ions structurally coordinated with nitrogen atoms of said ligands, and Cl$^-$ as counter anions, wherein said metal-organic material has the chemical formula $(PdCl_2N_2C_{26.5}H_{20})_n$, wherein n is an integer of at least 4, and a 3D crystalline micro or sub-micro structure optionally further comprising solvent molecules. This material is herein identified PdClL2 and may be formed, e.g., by adding a sonicated toluene solution of $Pd(COD)Cl_2$ to a toluene suspension of L2 in an oven-dried glass pressure tube, which is then sealed; heated for 3 days at 105° C. without stirring and with exclusion of light; and then gradually cooled to RT over 9-10 h. to thereby obtain PdClL2 as a yellowish precipitate. In one alternative process, PdClL2 may be formed by adding a sonicated toluene suspension of $PdCl_2$ to a toluene suspension of L2 in an oven-dried glass pressure tube, which is then sealed; heated for 3 days at 105° C. without stirring and with exclusion of light; and then gradually cooled to RT over 9-10 h. to thereby obtain PdClL2 as a yellowish precipitate. In another alternative process, PdClL2 may be formed by adding an ethylbenzene solution of $Pd(PhCN)_2Cl_2$ to an ethylbenzene suspension of L2 in an oven-dried glass pressure tube, which is then sealed; heated for 3 days at 105° C. without stirring and with exclusion of light; and then gradually cooled to RT over 9-10 h. to thereby obtain PdClL2 as a yellowish precipitate. In a further alternative process, PdClL2 may be formed by adding a toluene solution of $Pd(PhCN)_2Cl_2$ to a heptane suspension of L2 in an oven-dried glass pressure tube, which is then sealed; heated for 3 days at 105° C. without stirring and with exclusion of light; and then gradually cooled to RT over 9-10 h. to thereby obtain PdClL2 as a yellowish precipitate. The PdClL2 crystalline structures obtained may further comprise toluene, ethylbenzene and/or heptane molecules confined within the structural pores.

In yet another specific embodiment, the metal-organic material of the invention comprises ligands each being ligand L2, Zn(II) ions structurally coordinated with nitrogen atoms of said ligands, and OAc⁻ as counter anions, wherein said metal-organic material has the chemical formula $(Zn(OAc)_2N_2C_{26.5}H_{20})_n$, wherein n is an integer of at least 4, and a 3D crystalline micro or sub-micro structure optionally further comprising solvent molecules. This material is herein identified ZnOAcL2 and may be formed, e.g., by adding a chloroform solution of L2 to a DMF solution of $Zn(OAc)_2.2H_2O$ in an oven-dried glass pressure tube, which is then sealed; heated for 2 days at 105° C. without stirring and with exclusion of light; and then gradually cooled to RT over 9-10 h. to thereby obtain ZnOAcL2 as a light white precipitate having the geometrical shape of spheres. Alternatively, ZnOAcL2 may be formed by adding a chloroform solution of L2 to a DMF solution of $Zn(OAc)_2.2H_2O$ in an oven-dried glass pressure tube, which is then sealed; heated for 3 days at 105° C. without stirring and with exclusion of light; and then gradually cooled to RT over 9-10 h. to thereby obtain ZnOAcL2 as a light white precipitate having the geometrical shape of spheres. The ZnOAcL2 crystalline structures obtained may further comprise chloroform and/or DMF molecules confined within the structural pores.

In another specific embodiment, the metal-organic material of the invention comprises ligands each being ligand L2, Zn(II) ions structurally coordinated with nitrogen atoms of said ligands, and Cl⁻ as counter anions, wherein said metal-organic material has the chemical formula $(ZnCl_2N_2C_{26.5}H_{20})_n$, wherein n is an integer of at least 4, and a 3D crystalline micro or sub-micro structure optionally further comprising solvent molecules. This material is herein identified ZnClL2 and may be formed, e.g., by adding a chloroform solution of L2 to a DMF solution of $ZnCl_2.2H_2O$ in an oven-dried glass pressure tube, which is then sealed; heated for 3 days at 105° C. without stirring and with exclusion of light; and then gradually cooled to RT over 9-10 h. to thereby obtain ZnClL2 as a light white precipitate having the geometrical shape of spheres. In one alternative process, ZnClL2 may be formed by adding a chloroform solution of L2 to a DMF solution of $ZnCl_2.2H_2O$ in an oven-dried glass pressure tube, which is then sealed; heated for 2 days at 105° C. without stirring and with exclusion of light; and then gradually cooled to RT over 9-10 h. to thereby obtain ZnClL2 as a light white precipitate having the geometrical shape of spheres. In another alternative process, ZnClL2 may be formed by adding a chloroform solution of L2 to a DMF solution of $ZnCl_2.2H_2O$ in an oven-dried glass pressure tube, which is then sealed; heated for 3 days at 105° C. without stirring and with exclusion of light; and then gradually cooled to RT over 9-10 h. to thereby obtain ZnClL2 as a light white precipitate having the geometrical shape of spheres. The ZnClL2 crystalline structures obtained may further comprise chloroform and/or DMF molecules confined within the structural pores.

In still another specific embodiment, the metal-organic material of the invention comprises ligands each being ligand L2, Zn(II) ions structurally coordinated with nitrogen atoms of said ligands, and Br⁻ as counter anions, wherein said metal-organic material has the chemical formula $(ZnBr_2N_2C_{26.5}H_{20})_n$, wherein n is an integer of at least 4, and a 3D crystalline micro or sub-micro structure optionally further comprising solvent molecules. This material is herein identified ZnBrL2 and may be formed, e.g., by adding a chloroform solution of L2 to a DMF solution of $ZnBr_2$ in an oven-dried glass pressure tube, which is then sealed; heated for 2 days at 105° C. without stirring and with exclusion of light; and then gradually cooled to RT over 9-10 h. to thereby obtain ZnBrL2 as a white precipitate having the geometrical shape of spheres. The ZnBrL2 crystalline structures obtained may further comprise chloroform and/or DMF molecules confined within the structural pores.

In another embodiment, the metal-organic material comprises ligands L4, Ni(II) ions structurally coordinated with nitrogen atoms of the ligands, and Br⁻ as counter anions, wherein the metal-organic material has the chemical formula $(NiBr_2N_2C_{31}H_{26})_n$, wherein n is an integer of at least 4, and a 3D crystalline micro or sub-micro structure optionally comprising solvent molecules. This material has a barrel-like shape. This material is herein identified NiBrL4 and may be formed, e.g., by adding a chloroform solution of L4 to a DMF solution of $NiBr_2$ in an oven-dried glass pressure tube (the stoichiometric ratio of L4 to Ni is 1:2), which is then sealed; heated for 12 to 42 hours at 105° C. without stirring and with exclusion of light; and then gradually cooled to RT over 8-10 h. to thereby obtain NiBrL4 as a pale green precipitate. In one alternative process, NiBrL4 may be formed by adding a chloroform solution of L4 to a DMF solution of $NiBr_2$ in an oven-dried glass pressure tube (the stoichiometric ratio of L4 to Ni is 1:2), which is then sealed; heated for 2 days at 105° C. without stirring and with exclusion of light; and then gradually cooled to RT over 8-10 h. to thereby obtain NiBrL4 as a pale green precipitate. In another alternative process, NiBrL4 may be formed by adding a chloroform solution of L4 to a DMF solution of $NiBr_2$ in an oven-dried glass pressure tube, which is then sealed; heated for 3 days at 105° C. without stirring and with exclusion of light; and then gradually cooled to RT over 8-10 h. to thereby obtain NiBrL4 as a pale green precipitate. The NiBrL4 crystalline structures obtained may further comprise chloroform and/or DMF molecules confined within the structural pores.

In another embodiment, the metal-organic material of the invention comprises ligands each being ligand L4, Ni(II) ions structurally coordinated with nitrogen atoms of said ligands, and $NO_3^-$ as counter anions, wherein said metal-organic material has the chemical formula $(NiNO_3N_2C_{31}H_{26})_n$, wherein n is an integer of at least 4, and a 3D crystalline micro or sub-micro structure optionally comprising solvent molecules. The material is egg shaped. This material is herein identified NiNO$_3$L4 and may be formed, e.g., by adding a chloroform solution of L4 to a DMF solution of $Ni(NO_3)_2$ in an oven-dried glass pressure tube (the stoichiometric ratio of L4 to Ni is 1:2), which is then sealed; heated for 2 days at 105° C. without stirring and with exclusion of light; and then gradually cooled to RT over 8-10 h. to thereby obtain NiNO$_3$L4 as a light yellow-green precipitate. The NiNO$_3$L4 crystalline structures obtained may further comprise chloroform and/or DMF molecules confined within the structural pores.

In still another embodiment, the metal-organic material of the invention comprises ligands L4, Cu(II) ions structurally coordinated with nitrogen atoms of the ligands, and $NO_3^-$ as counter anions, wherein the metal-organic material has the chemical formula $(CuNO_3N_2C_{31}H_{26})_n$, wherein n is an integer of at least 4, and a 3D crystalline micro or sub-micro structure optionally comprising solvent molecules. This material is shaped as hexagonal prisms. This material is herein identified CuNO$_3$L4 and may be formed, e.g., by adding a chloroform solution of L4 to a DMF solution of $Cu(NO_3)_2$ in a glass pressure tube (the stoichiometric ratio of L4 to Cu is 1:2), which is then sealed; heated for 5 days at 105° C. without stirring and with exclusion of light; and then gradually cooled to RT over 8-10 h. to thereby obtain $CuNO_3L4$ as a green precipitate. The $CuNO_3L4$ crystalline structures obtained may further comprise chloroform and/or DMF molecules confined within the structural pores.

In one embodiment, the crystalline structures are modified with nanoparticles of a second metal. Once the crystalline structures are made, a solution of a second metal is casted on the MOF containing substrate and allowed to react with the MOF and optionally subsequently heated. For example, a silicon substrate is drop-casted with a reaction mixture of NiBrL4 and the solvents are allowed to evaporate in air. A drop of TOAB-capped AuNPs (gold nanoparticles) in toluene is casted on the MOF containing substrate and allowed to react in air. After 30 min, the remaining AuNP-solution is removed and the residue is washed twice with toluene. Optionally, the AuNP-coated MOF may be heated to about 150° C. for 6 to 20 hours.

In another embodiment of the invention, the MOF may include at least two metals. The MOF is made using at least two metal solutions and a ligand, wherein the stoichiometric ratio of ligand to metal is 1:2). The two metal solutions may be solutions of the same metal with different anions, or a solution of a first metal and a solution of a second metal. In the first instance, one example includes, but is not limited to, a solution of $NiBr_2$ and $Ni(NO_3)_2$. In the second instance, one example includes, but is not limited to, a solution of $Ni(NO_3)_2$ and $Cu(NO_3)_2$. The two solutions may be mixed in different proportions such as a percentage of total metal solution, while maintaining the ratio of metal to ligand to 2:1. The metal solutions can be present as a percentage of the total metal solution as determined by the stoichiometric amount necessary to maintain the metal to ligand ratio. For example, a first metal solution is present in 85% and the second metal solution is present in 15%. Other examples of percentages include, but are not limited to, 85%, 50%, 25%, and 15%. The process for making the mixed-metal MOF follows that described for single metals, such as Ni or Cu.

In another aspect, the present invention relates to a method for the preparation of a metal-organic material as defined above, comprising the steps of: (i) providing (a) an organic solution or suspension of a metal salt, herein referred to as the "metal component", consisting of anions and said metal ions; and (b) an organic solution or suspension of said ligands, herein referred to as the "organic component", in a pressure vessel; (ii) sealing and keeping said pressure vessel for a period of time, e.g., for about 1, 2, 3, 4, 5, 6, 7, 8, 9 or 10 days, or more, with exclusion of light and without stirring, thereby reacting said metal ions with said ligands to obtain said metal-organic material as a precipitate; and (iii) collecting said precipitate. It should be noted that where particular values are described in the description and claims, unless otherwise stated, the term "about" means that an acceptable error range, e.g., up to 5% or 10%, for the particular value should be assumed.

The term "pressure vessel" as used herein refers to a closed container designed to hold liquids or gases at a pressure substantially different from the ambient pressure. Pressure vessels can theoretically be almost any shape, e.g., cylinders with end caps, i.e., heads, either hemispherical or dished (torispherical), and can be made of any suitable composite material. In one embodiment, the pressure vessel utilized in the method of the present invention is a glass pressure vessel, more particularly, a glass pressure tube as used in the studies described herein.

In certain embodiments, step (ii) of the method of the invention is carried out while heating the pressure vessel containing the metal salt solution/suspension and the ligand solution/suspension to a temperature ranging from 60° C. to 120° C., e.g., from 60° C. to 70° C., 70° C. to 80° C., 80° C. to 90° C., 90° C. to 100° C., 100° C. to 105° C., 105° C. to 110° C., 110° C. to 115° C., or 115° C. to 120° C., for the whole said period of time or a part thereof, and then gradually cooling said pressure vessel. As shown herein, in some cases, step (ii) comprises sealing and keeping said pressure vessel for a period of time with exclusion of light and without stirring, while heating to a temperature as defined above for the whole period of time and then gradually cooling, e.g., to room temperature, prior to step (iii). Alternatively, step (ii) may comprise sealing and keeping said pressure vessel for a period of time with exclusion of light and without stirring, while heating as defined above for a part of said period of time, i.e., at the beginning of said period of time, during said period of time, or at the end of said period of time, and then gradually cooling, e.g., to room temperature.

In certain embodiments, steps (i) and (ii) of the method of the invention are carried out under inert conditions, e.g., under argon or $N_2$.

The organic solvents in which said ligands and metal salt are dissolved may independently be either polar or nonpolar, wherein the solubility of the ligands in the organic solvent in which they are dissolved determines whether the organic component would be in the form of a solution or suspension, and the solubility of the metal salt in the organic solvent in which it is dissolved determines whether the metal component would be in the form of a solution of suspension. Non-limiting examples of organic solvents include chloroform, dimethylformamide (DMF), alkanols such as methanol, ethanol, isopropanol, n-butanol, sec-butanol, isobutanol, pentanol and hexanol, DMSO, acetonitrile, ethylene glycol, toluene, benzene, ethylbenzene, ether (diethyl ether), and alkanes such as pentane, hexane, cyclohexane, heptane, cycloheptane, octane, cyclooctane, nonane, decane and decalin.

As shown herein, in cases the solubility of the metal salt in the organic solvent utilized is poor, however an organic solution rather than suspension of the metal salt is desired, a compound capable of forming a coordination complex, i.e., metal complex, with the metal atom thus increasing the solubility of said metal salt in said organic solvent may be added. In particular such cases exemplified herein, $PdCl_2$ in which the Pd atoms are coordinated with 1,5-cyclooctadiene (COD) or benzonitrile (PhCN), i.e., $Pd(COD)Cl_2$ or $Pd(PhCN)_2Cl_2$, respectively, were dissolved in toluene or ethylbenzene so as to obtain a toluene or ethylbenzene solution rather than suspension of $PdCl_2$.

According to the method of the invention, the metal-organic material is obtained as a result of a reaction taking place in the pressure vessel during step (ii). As clearly shown herein, metal-organic materials comprising the same ligands and metal ions, but having different 3D crystalline structures, thus potentially different physical and chemical properties, are obtained depending on the reaction components, e.g., anions and organic solvents in which said ligands and metal salt are dissolved, as well as the reaction conditions, e.g., the period of time during which the organic component and metal component are reacted in step (ii), the temperature in which the reaction is conducted or the thermal profile of the reaction (in cases the reaction includes heating for a part of said period of time), and cooling rate (in cases the reaction comprises heating for the whole said period of time or a part thereof).

The metal-organic material obtained by the method of the present invention comprises metal ions, preferably transition metal ions, coordinated to organic ligands each of the general formula I to form one-, two-, or three-dimensional structures, wherein the particular metal ion and organic ligand selected dictates the structure and hence physical and chemical properties of the material. In certain embodiments, the metal-organic material has a 3D crystalline micro or sub-micro structure that may have a particular geometric shape as defined above. It should be understood that while crystalline micro and sub-micro structures obtained using different reaction components and/or under different reaction conditions may have different geometrical shapes, a preparation process as defined above, utilizing particular reaction components and carried out under particular reaction conditions, results in a population of 3D crystal structures having uniform geometrical shape.

In certain embodiments, the geometrical shape of the 3D micro and sub-micro structures obtained by the method of the invention is thus affected by reaction components and/or the reaction conditions or parameters in steps (ii), wherein said reaction components are, e.g., one or more of said metal ions, anions, and organic solvents, and said reaction conditions or parameters are, e.g., one or more of said temperature, period of time, and cooling rate.

The MOFs of the present application are useful as adsorbents in processes for gas adsorption, e.g., $H_2$, CO, $CO_2$ or methane adsorption, or gas separation and/or purification, e.g., separation of $CO_2$ from methane.

In yet another aspect, the present invention thus relates to use of a metal-organic material as defined above as an adsorbent in a process for gas adsorption or gas separation.

In still another aspect, the present invention relates to a process for gas adsorption or gas separation by adsorbing said gas to an adsorbent, the improvement wherein said adsorbent is a metal-organic material as defined above.

The invention will now be illustrated by the following non-limiting Examples.

EXAMPLES

Materials and Methods

General Methods.

Glass pressure tubes were cleaned by immersion in a piranha solution (7:3 v/v, $H_2SO_4$/30% $H_2O_2$) for 10 min and deionized (DI) water and then dried for 12 h at 130° C. Caution: piranha is an extremely dangerous oxidizing agent and should be handled with care using appropriate personal protection.

Transmission Electron Microscopy (TEM).

TEM imaging was performed with a Philips CM-120 instrument operating at 120 kV, equipped with a charge-coupled device camera (2 k×2 k Gatan Ultrascan 1000). TEM samples were prepared by placing a 5 µl drop of the reaction mixture on a formvar/carbon, 400 mesh Cu grid and blotting after 10 s. Due to beam sensitivity of the specimens, TEM imaging and SAED measurements were performed under low-dose conditions. An EDAX EDS system was used to perform the elemental analysis.

Scanning Electron Microscopy (SEM).

SEM measurements were performed using HRSEM ULTRA-55 ZEISS and HRSEM SUPRA-55 VP ZEISS instruments at an EHT voltage of 3 kV. SEM samples were prepared by placing a drop of the reaction mixture or a DMF suspension of isolated MOFs on a silicon substrate, which was dried under air.

FTIR and NMR Spectroscopy.

The infra-red spectra were obtained using a Nicolet 460 single beam FT-IR. $^1H$ and $^{13}C\{^1H\}$ NMR measurements were run on a 300 MHz Bruker NMR spectrometer.

Atomic Force Microscope (AFM).

AFM topographical imaging was performed on a P47 Solver AFM (NT-MDT, Zelenograd, Russia) using AC240 probes (Olympus) in intermittent contact mode, as well as with Multimode 8 AFM (Bruker, Santa Barbara, Calif.). The latter system was operated with the "Peak force Quantitative Mechanical Mapping (PF-QNM)" mode which enables acquisition of elastic modulus simultaneously with the topographic image. For this measurement, Bruker RTESPA probes were used. The spring constant, determined by the Sader method (Sader, et al., *Rev. Sci. Instrum.*, 1999, 70, 3967) was 80 N/m. The elastic modulus is derived from force curves acquired at each pixel, and rely on several calibrations (cantilever deflection sensitivity, spring constant, tip radius) which are input into the DMT analysis (Tabor, D., *J. Coll. Int. Sci.* 1977, 58, 2-13). The deformation was in the order of 5-10 nm, thus very sensitive to the tip and sample surface condition, which can change the effective tip radius during course of scan. Estimated uncertainty in modulus measurement is 30%. Samples were prepared on silicon substrates as in the case of SEM.

Rapid Thermal Processing (RTP) and Thermogravimetric Analysis (TGA).

RTP was carried out on a Rapid Thermal Annealer for 5 min. under a stream of 10% $H_2/N_2$ or under vacuum at different temperatures (200-600° C.). The samples were prepared as in the case of SEM. TGA was performed on a SDT Q600 V8.3 Build 101 instrument using alumina sample pans under a stream of $N_2$.

Magnetic Measurements.

Figure 20A:
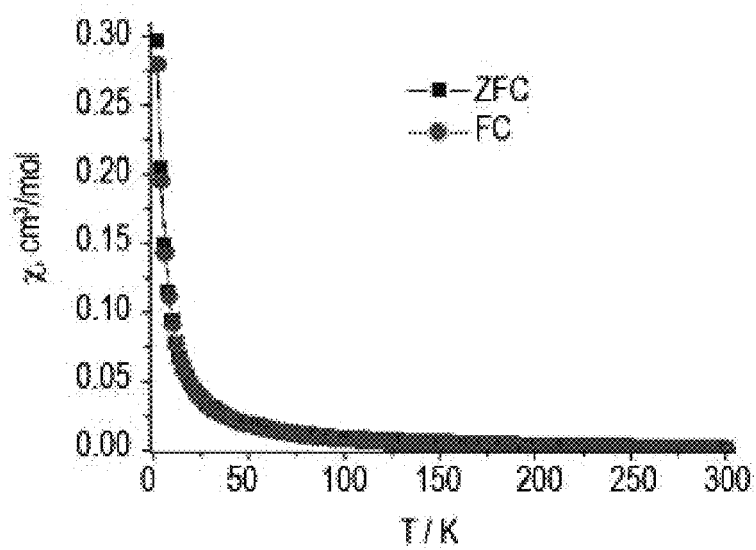
FIGS. 20A-20C show ZFC and FC temperature dependence of molar magnetic susceptibility of NiClL1 (FIG. 20A); magnetic field dependencies of magnetic moment at T=6K (FIG. 20B); and calculated effective magnetic moment of $Ni^{2+}$ vs. temperature (FIG. 20C).
Figure 20B:
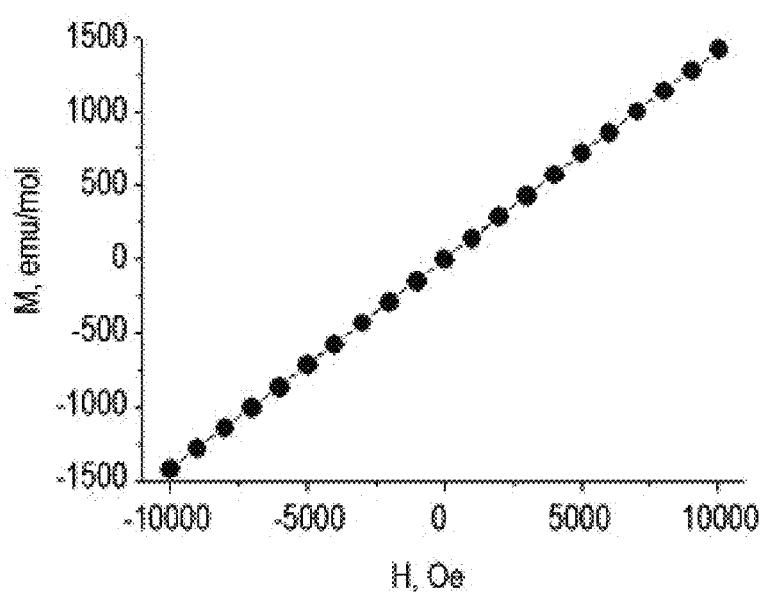
Figure 20C:
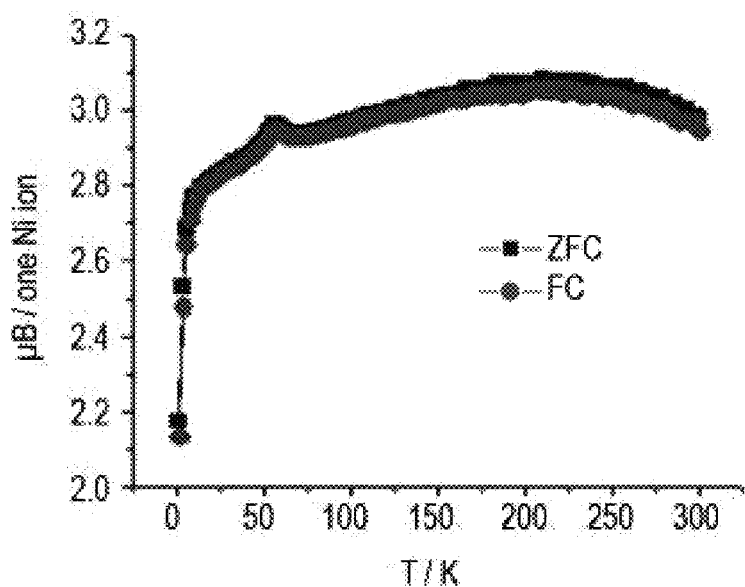
Figure 21:
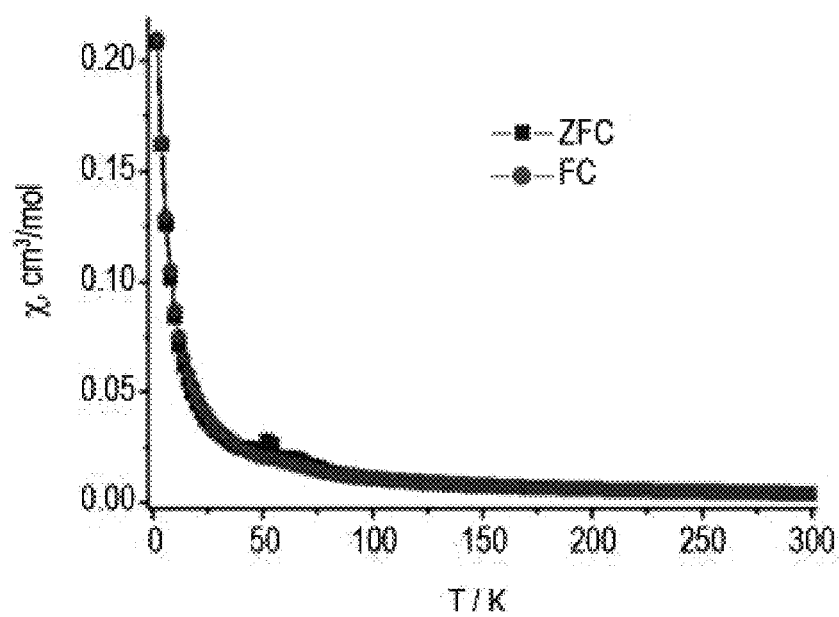
FIG. 21 shows magnetic profiles (ZFC and FC measurement) of NiBrL2.

The magnetic properties of isolated samples were measured using a SQUID magnetometer MPMS XL. The samples were weighed and placed in gelatine capsules and cooled from RT down to 2K without applying any external magnetic field (ZFC) and an internal magnetic field of strength 1000 Oe (FC). Temperature dependences of the magnetic moment were measured during heating from 2K to 300K under an applied external magnetic field (H=1000 Oe). The dependence of magnetic susceptibility on the temperature was normalized using the estimated chemical formula of NiClL1 $(NiCl_2N_2C_{26.5}H_{16})_n$ and NiBrL2 $(NiBr_2N_2C_{26.5}H_{20})_n$. This dependence is similar for the inclusion of DMF (0.5-4 molecules/Ni). The ZFC and FC dependences were found to be superimposed (FIGS. 20A, 21). The Weiss equation defines the temperature dependency of magnetic susceptibility and can be expressed as $\chi = \chi_0 + C/(T-\theta)$, where C is Curie constant, $\chi_0$ is the temperature independent parameter and $\theta$ corresponds to the Weiss parameter.

Gas Uptake Studies.

The gas adsorption studies were carried out on a Pressure Composition Isotherm (PCI) instrument (Advanced Materials Corporation, USA). About 50 mg of the compound, e.g., NiClL1, was loaded into a sample chamber inside a glove box under argon. The sample chamber was then connected to a vacuum line. The sample was activated by heating slowly to 120° C. (for $CH_4$ adsorption) and to 70° C., 100° C. and 120° C. (for $H_2$ adsorption) and held for 4 hours at these temperatures followed by cooling to RT. The temperature of the sample chamber was held constant during the measurements. The gas uptake was determined using Sieverts principle. The density of the sample was measured by gas pycnometry using helium (10 bar).

General Procedure for the Synthesis of the MOFs.

A $CHCl_3$ solution (1.0 ml) of the polypyridyl ligand L1 (Schilling, et al., *Eur. J. Org. Chem.*, 2011, 1743-1754) or L2 (Thompson, et al., *Inorg. Chim. Acta.*, 1997, 256, 331-334) (6.8 µmol) was added to a DMF solution (3.0 ml) of the corresponding metal salt: $NiCl_2$, $NiBr_2$, $CuCl_2$, $CuBr_2$ and $Cu(NO_3)_2$ (6.8 µmol for 1 eq. and 13.6 µmol for 2 eq.), in a glass pressure tube. Then, the tube was sealed and heated for 5 days at 105° C. without stirring and with exclusion of light, followed by controlled cooling to RT over 9-10 h in steps of 10° C./h. This resulted in a precipitate (light green for the Ni-based MOFs and dark green for the Cu-based MOFs). The MOFs were collected in near quantitative yield (>95%) by centrifugation of the reaction mixture for ~10 min. at 5000 rpm and decanting the mother liquor.

Example 1

Homogeneously Microstructured Crystalline Nickel-Organic Coordination Polymers

Micro-sized brick-like structures of the coordination polymer were obtained by differential solvothermal synthesis as described. A DMF solution of 1 equivalent of $NiCl_2.6H_2O$ was heated with a chloroform solution of 0.5 equivalents of the ligand L1 in a sealed pressure tube at 105° C. for 5 days in the dark, and then subjected to slow cooling over 9-10 hours. A white precipitate was formed immediately on mixing the two solutions and was allowed to stand and sediment without disturbance under the mentioned conditions. After cooling to RT, the light green precipitate was collected by centrifugation.

Figure 1B:
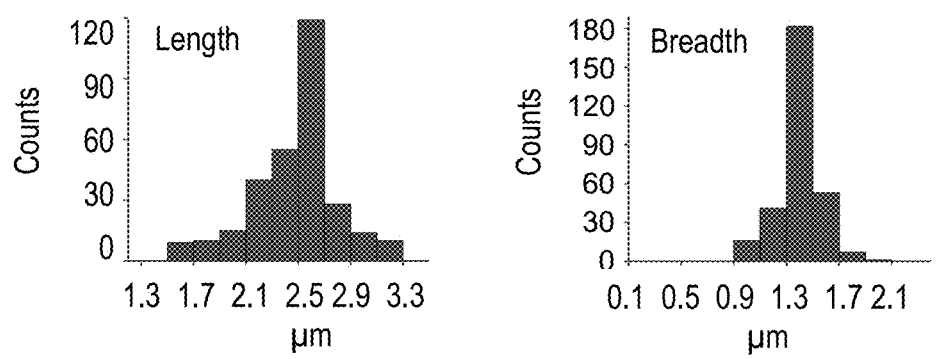

SEM image of NiClL1 revealed the brick-like structures and a statistical analysis on three hundred randomly chosen brick-like structures from a representative sample of NiClL1 established a reasonable uniformity in size distribution (FIGS. 1A-1B) with most of the structures fitting in lengths of 2.5-2.7 µm, breadths of 1.2-1.4 µm and thickness of 200-300 nm. TEM images showed the crystalline nature of the material; the existence of lattice planes could be recognized via TEM imaging and SAED (FIGS. 2A-2B); and the longest axis of symmetry was found to be along the length of the crystal.

AFM studies revealed the same shapes as seen in electron micrographs as well as the apparent surface roughness of the material. The debris observed also in the TEM micrographs appears to be disordered material, ranging from tens to over one hundred nm height. The upper surface of the crystallites was generally flat, although scattered depressions could be observed, as well as new layers appearing over parts of the surface (FIGS. 3A-3D).

Figure 4:
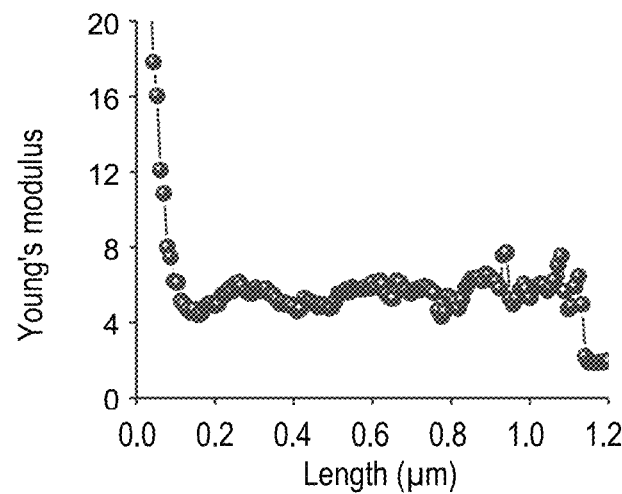
FIG. 4 shows Young's Modulus across one of the randomly chosen brick-like mucrostructures, as measured by an AFM.

Measurements of elastic modulus on these nanostructures gave values between 2-12 gigapascals (GPa). These values are within the range of those observed for organic crystals (Roberts, et al., *Powder Technology*, 1991, 65 139-146). The elastic modulus was measured simultaneously with the topographic image, so values are correlated at the pixel level with topographic features. FIGS. 2A-2B show images of modulus and corresponding topography. The modulus signal over the Si substrate saturates at high values for this probe. For these stepped features, the modulus of the higher regions was about half that of the lower regions. This observation is consistent with the premise that crystallites undergo a polishing process during the growth, with the higher, less ordered regions being removed with time. Such less ordered regions are expected to be more deformable and hence show lower modulus values (FIG. 4).

Figure 5:
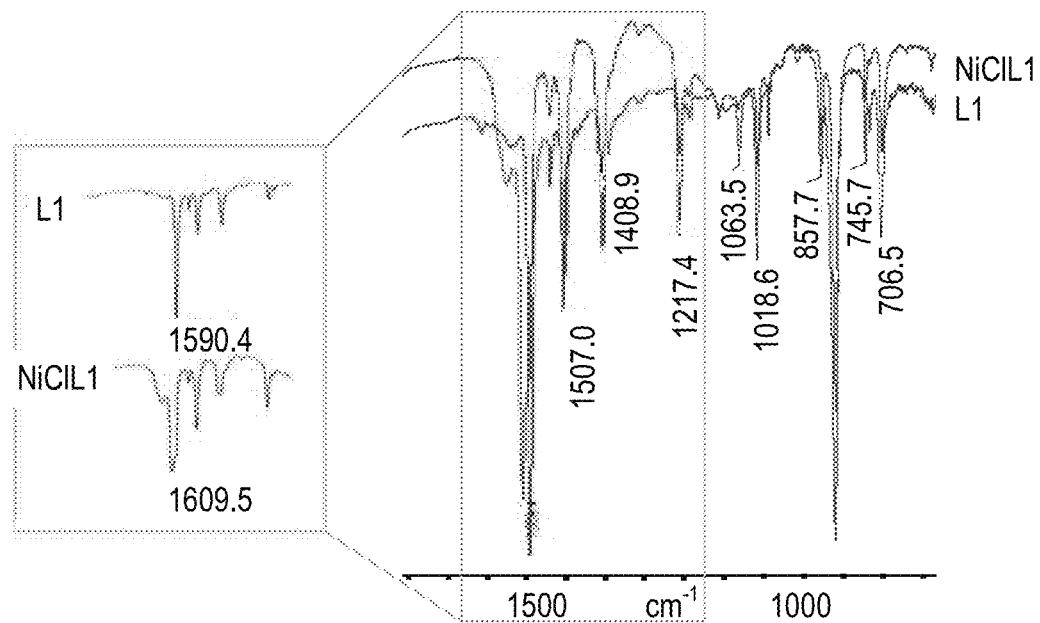
FIG. 5 shows FT-IR spectra (KBR pellet) of L1 and NiClL1.
Figure 6:
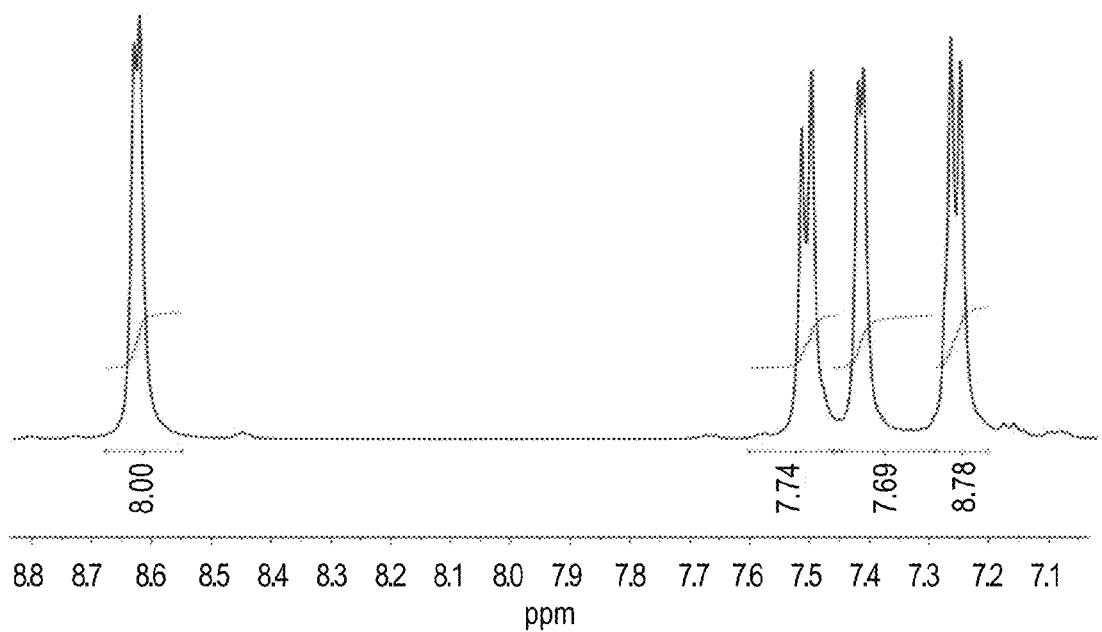
FIG. 6 shows representative $^1$H NMR spectrum (CDCl$_3$) of the CHCl$_3$ extract after reacting NiClL1 with conc. HCl and neutralizing with Et$_3$N. The spectrum corresponds to pure ligand L1.

FT-IR spectrum (KBr pellets) of NiClL1 showed a shift of 20 $cm^{-1}$ compared to free ligand L1 (FIG. 5). Unsurprisingly, concentrated acid digested the whole system and $^1H$ NMR of resulting mixture extracted with chloroform after neutralizing with $Et_3N$, matched exactly the ligand L1 (FIG. 6) and the mass spectrometric analysis of the crude mixture revealed the presence of the ligand L1 and $NiCl_2$. MALDI-TOF analysis also confirmed that the ligand was intact in the complex NiClL1. The elemental composition of the micro bricks were confirmed by nanoprobe X-ray EDS, revealing the presence of Ni, Cl and N atoms and the Ni/N ratio was found to be 0.44 (FIG. 7) and the value is in close agreement with the formation of a completely formed coordination saturated network comprising of two pyridines per Ni centre (Kaminker, et al., *J. Am. Chem. Soc.* 2010, 132, 14554; Choudhury, et al., *J. Am. Chem. Soc.* 2010, 132, 9295), but other modes of coordination may not be completely excluded.

Figure 8:
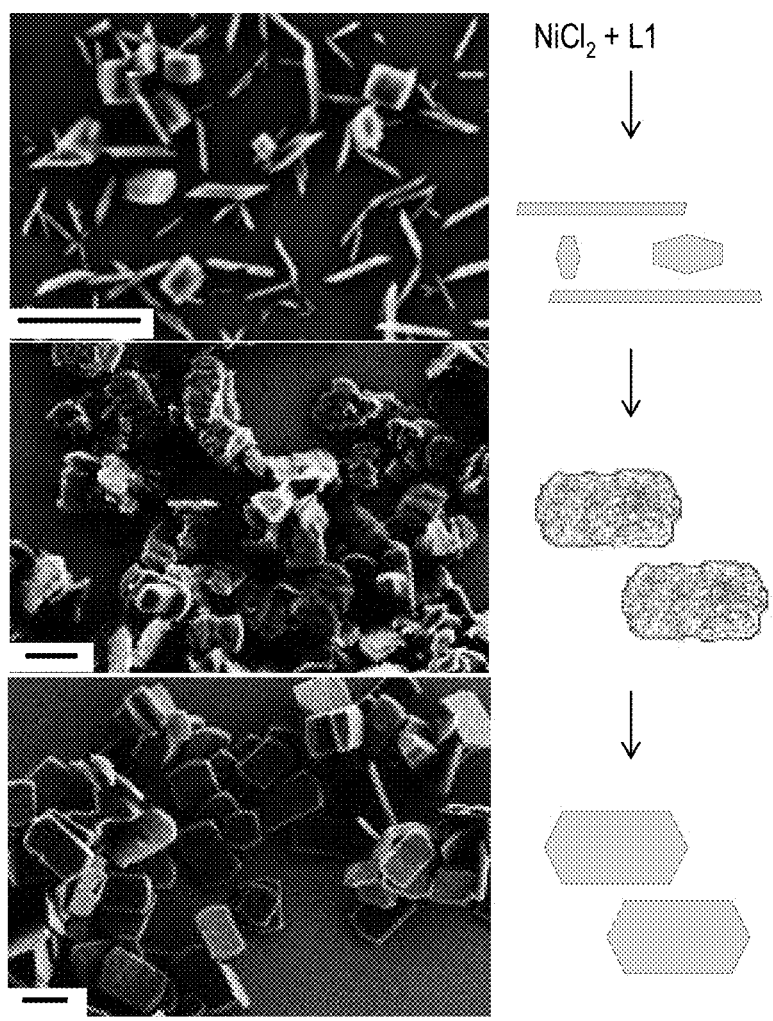
FIG. 8 shows time-dependent SEM analysis on the formation of brick-like structures NiClL1 (left panels) and a cartoon depicting the NiClL1 formation (right panels) immediately on mixing the CHCl$_3$/DMF solutions of NiCl$_2$.6H$_2$O and L1 (upper panels); after heating the reaction mixture at 105° C. for 48 h in a sealed pressure tube (middle panels); and after heating the reaction mixture for 5 days and controlled cooling down to RT (scale bar=2 μm) (lower panels).

The formation of these well-defined rectangular structures may be viewed as an impact of face or axial confined growth mechanism, but the mechanistic understanding behind the formation of such uniform structures is still preliminary and can be expected to follow a regular coordination process followed by a thermally initiated close packing by the fusion of individual building blocks. Time dependent SEM analysis alongside the course of reaction revealed a speculative but justifiable mechanism for the formation of the finally observed structures. As expected, the ligand L1 on mixing with the Ni salt solution immediately formed the corresponding coordination polymer with non-uniform rod- and very small block-like structures (FIG. 8, upper panels), which in turn on heating under pressure fused to form the brick-like micro structures (FIG. 8, middle panels). The effect of the solvent mixture at any point time may not be completely excluded as the coordination polymer precipitates instantaneously and hence may account for the reduction in surface tension through agglomeration. Over time and under the influence of high temperature, the surface of these structures got smoothened to a large extent giving rise to flat faces with some apparent degree of surface roughness (FIG. 8, lower panels). Thus, the proposed working mechanism involves coordination/nucleation followed by aggregation/oligomerisation, fusion/growth and annealing. Mirkin and co-workers have proposed a similar mechanism for the formation of perfect micro spheres during the polymerization of Troger's base precursors and Zn(II) (Spokoyny, et al., *Chem. Soc. Rev.*, 2009, 38, 1218-1227; Oh and Mirkin, 2005; Jeon, et al., *Small*, 2009, 5, 46-50).

The micro moieties thus obtained was found to be insoluble in all common solvents including water and was found to be stable in most of the commonly used solvents in air at RT. This stability of the structure may be established by the SEM images of the solid material suspended in water, DMF and a mixture of both in dark, taken after 2 months (FIGS. 11A-11C).

The final structure of the coordination polymer was found to depend on several parameters including the technique employed, molar ratios of the reagents, solvent system, time of the reaction and temperature. It has already been mentioned that mixing a $CHCl_3$ solution of the ligand L1 with a DMF solution of $NiCl_2.6H_2O$ at RT gave non-uniform rod- and very small block-like structures. Layering carefully a $CHCl_3$ solution of the ligand L1 under a DMF solution of the Ni salt in a molar ratio of 1:1 or 1:2 afforded a light green precipitate when allowed to stand overnight in the dark, and SEM images of a representative sample showed a mixture of rods—longer and more uniform and some amounts of junk material with no well-defined structure. Heating this mixture (after complete diffusion in about 4 days) in a pressure tube to 80-105° C. for 3-5 days brought about drastic changes in the structures observed under SEM suggesting that the longer rods thus obtained were unstable and underwent random melting and fusion under thermal treatment as the junk material along with the rods seemed to have aggregated to form some sort of lumps.

Although changing the molar ratio of the ligand and the metal did not affect much the outcome of the layering technique, it was found to have substantial effect on the structural features under thermal protocol. Heating the ligand and the metal in the same solvent system under the same conditions, but in a ratio of 1:1, resulted in smaller and different brick-like structures with a wider size distribution (FIGS. 12A-12B).

The solvents used for the reaction were also found to have pronounced effect on the final structures observed under the electron microscopes. Using DMF alone as the solvent even though the ligand L1 was insoluble (FIG. 13, panel B) resulted in complete loss of the brick-like structure, where as a 1:2 mixture of DMF/$CHCl_3$ in place of a 1:3 mixture led to the formation of a comparatively more defined structures but no real brick-like moieties were observed (FIG. 13, panel C). This may be explained by the acidic nature of the proton in $CHCl_3$ that is capable of exerting H-bonded interactions with pyridines, thereby interfering with the coordination power of the lone pair. Addition of 0.25-0.5 ml of water to the 1:3 DMF/$CHCl_3$ mixture completely ruined the system (FIG. 13, panel D) and these results may also underline the effect of solvent polarity on the formation of these well-defined rectangular structures. It may be noted that in all cases except where a small amount of water was added, the precipitation of the coordination polymer was instantaneous and had the physical appearance of white insoluble material obtained under standard conditions.

The thermal behavior of materials is yet another interesting aspect of coordination polymers. RTP under a stream of 10% $H_2$/$N_2$ of the brick-like Ni(II) coordination polymer established that the structure are stable up to a temperature around 300° C. (FIGS. 14A-14D and FIGS. 15A-15D). Moreover, the boron doped silicon surface is found to induce better stability to these structures and it may be noted that the micro-bricks lying flat on the surface retained their shape at even higher temperatures. When subjected to processing above 400° C., the melted structures were found to be adorned with nanoparticles of metallic nickel (approx. 20-25 nm).

Another significant observation was that the structures appear to be much more stable if thermally treated under vacuum (FIGS. 16A-16D), even though metallic nanoparticle adornment was still found to occur during the event.

The TGA on the brick-like structures allowed us to confirm the presence of DMF as a coordinating solvent inside the crystal lattice, since a weight loss was observed around 150° C. (FIG. 17). As found after Rapid Thermal Annealing, the structures were quite stable at this temperature and it could only be the solvent that vaporizes at this characteristic boiling point of DMF and hence justifies the observed weight loss.

Metal organic frameworks and coordination polymers find interesting application as gas storage materials (Manson, et al., *Chem. Sci.* 2014, 5, 32-51; Adisa, et al., *Nanoscale* 2012, 4, 3295-3307). The gas adsorption properties NiClL1 was studied as a function of pressure and the experiments done on pre-activated samples showed reasonable amount of methane (about 7.5 wt % at ambient temperature or 0° C. and 11.7 wt % at −78.5° C. and ~35 atm pressure) and hydrogen (about 1.75 wt % at ~35 atm pressure) adsorption (FIGS. 18, 19 for $H_2$ adsorption-desorption isotherms). Moreover, the samples, during measurements, exhibited very little hysteresis between adsorption and desorption runs. The same technique was also used to determine the density of the substance and was found to be ~0.687 g/cc.

SQUID measurements revealed paramagnetic behavior for both NiClL1 and NiBrL2. The ZFC and FC dependences were found to be superimposed (FIG. 20A, 21). These magnetic properties are in agreement with a near tetrahedral or an octahedral coordination geometry of the metal center (Bridgeman, A. J. *Dalton Trans.* 2008, 1989-1992).

It has been tried via various techniques including electron diffraction, powder XRD and synchrotron diffraction, to solve the crystal structure of NiClL1, but has remained unsuccessful till date, partially due to the size of the crystallite (that made it difficult to isolate a single crystal and to have a compatible beam line in the range of the size of the crystallite) and partially due to the low intensity of diffraction patterns observed (especially in electron diffraction). Nevertheless, the magnetic properties throw some light into the possible geometry—the paramagnetic behavior neglects to a large extent the possibility of a square planar Ni(II) complex, thereby leaving the options for a tetrahedral or an octahedral one. It has already been known that in a square planar complex, the ligand exerts a very strong σ interaction with the metal at the expense of complete electron pairing, leaving the σ* orbitals unoccupied, resulting in a diamagnetic behavior (Bridgeman, 2008).

Example 2

Topological Control in Metal Organic Frameworks—from Rectangular Bricks to Stellated and Interpenetrating Polyhedra In this study, we demonstrate the control of structural uniformity and diversity for MOFs. More particularly, we introduce the assembly of a series of 3-dimensional (sub)-microstructured MOFs with a narrow size distribution as well as excellent control over their topologies. Diverse structures are demonstrated, ranging from elongated hexagons and rectangular prisms to stellated and interpenetrating polyhedral, by systematically varying the (i) metal center; (ii) anion; (iii) organic ligand; and (iv) reaction conditions, i.e., solvent, temperature, and aerobic vs. anaerobic. For instance, the use of Ni(II) salts result in distinct polyhedral topologies as opposed to Cu(II) precursors that form interpenetrating and/or stellated polyhedra. Such metal-organic structures are highly uncommon (Masoomi and Morsali, 2013). The uniformity in shape and size of our materials is attained via solvothermal synthesis without the use of surfactants or external modulators (e.g., pyridine, cetyl trimethyl ammonium bromide) (Sindoro et al., 2014; Gao, et al., *Inorg. Chem.* 2014, 53, 691-693; Ranft, et al., *Cryst Eng Comm* 2013, 15, 9296-9300; Guo, et al., *RSC Adv.* 2012, 2, 5424-5429; Cho et al., 2008). Follow-up electron microscopy studies of the formation of the MOFs revealed a complex sequence of reactions. For the Ni-based MOFs, two types of growth process were observed involving nucleation and polishing, whereas fusion processes play a dominant role in the formation of the Cu-based MOFs.

To achieve and rationalize the topological control over metal-organic microstructures, ligand-metal-anion combinations are needed that: (i) form robust and extended 3D networks by interconnected tetrahedral nodes allowing the generation of diamondoid networks (Batten, S. R., *Cryst Engg Comm* 2001, 18, 1-7); and (ii) give rise to exceptionally high permanent microporosities and/or channels with incorporation of solvent molecules to stabilize the microstructures. Therefore, we used the two organic ligands L1 and L2 and commercially available salts of Ni(II) and Cu(II). These tetrahedral ligands are rigid, possess a full $T_d$ symmetry, and four metal ion binding sites. This combination ensures the formation of robust, porous and extended 3D networks (Lu et al., *Chem. Soc. Rev.*, DOI: 10.1039/C4CS00003J). Ni(II) and Cu(II) salts have a high affinity for pyridyl ligands (Tomasik, et al., *In Chemistry of Heterocyclic Compounds: Pyridine Metal Complexes* (Part 6, Volume 14). (John Wiley & Sons, Inc., 2008); Hasenknopf, et al., *Proc. Natl. Acad. Sci. USA*. 1996, 93, 1397-1400), nevertheless the metal-N bond strength allows for the rearrangement of kinetic structures into thermodynamic products to occur at elevated temperatures (Kaminker, et al., *Angew. Chem, Int. Ed.* 2011, 50, 3224-3226). The scope of this study is demonstrated by the use of metals that have different coordination requirements. In addition, the dominant role of the anions in the formation of our microstructures has been demonstrated.

In a typical experiment, a DMF solution of the metal salt was mixed with a chloroform solution of 0.5 or 1 equivalent of L1 or L2 and heated in a glass pressure tube at 105° C. with the exclusion of light. After 4-5 days, the reaction mixture was gradually cooled over 9-10 hours and the microstructures were collected quantitatively by centrifugation. The crystalline microstructures have been characterized by electron microscope analysis, XRD and AFM. Information at the molecular level has been obtained by infra-red (IR) spectroscopy, magnetic measurements, and gas adsorption. The nickel structures have also been tested for their thermal stability.

SEM and TEM imaging revealed that the combinations of $NiCl_2$ and L1 or $NiBr_2$ and L2 in a 2:1 ratio, respectively, yield monodispersed structures (NiClL1 and NiBrL2; FIGS. 22A-22C and FIGS. 23A-23C). Although both MOFs have regular hexagonal topologies, NiClL1 forms a distinctly elongated hexagon that can also be observed by optical microscopy (FIG. 10). These observations demonstrate that minor structural differences in the organic ligand (i.e., L1: C≡C vs. L2: C=C) and the anion (Cl, Br) are key-factors that can be used to tune the topology of these MOFs at the microscopic level while a high level of uniformity is retained. Furthermore, the metal-to-ligand and solvent ratios can be used to control the MOF topologies. For instance, using $NiCl_2$ and L1 in a 1:1 ratio resulted in smaller hexagonal topologies, whereas changing the chloroform content resulted in elongated structures (FIGS. 24A-24F). Addition of water to the reaction resulted in structural deformation (FIG. 24, panel F).

Figure 7:
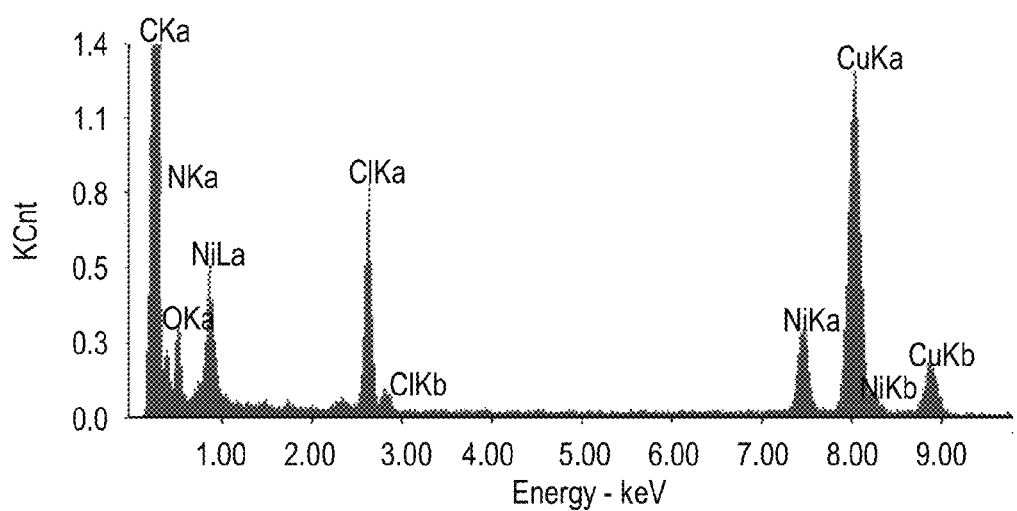
FIG. 7 shows a representative EDS measurement of a brick-like microstructure of NiClL1 using TEM (120 kV).
Figure 9:
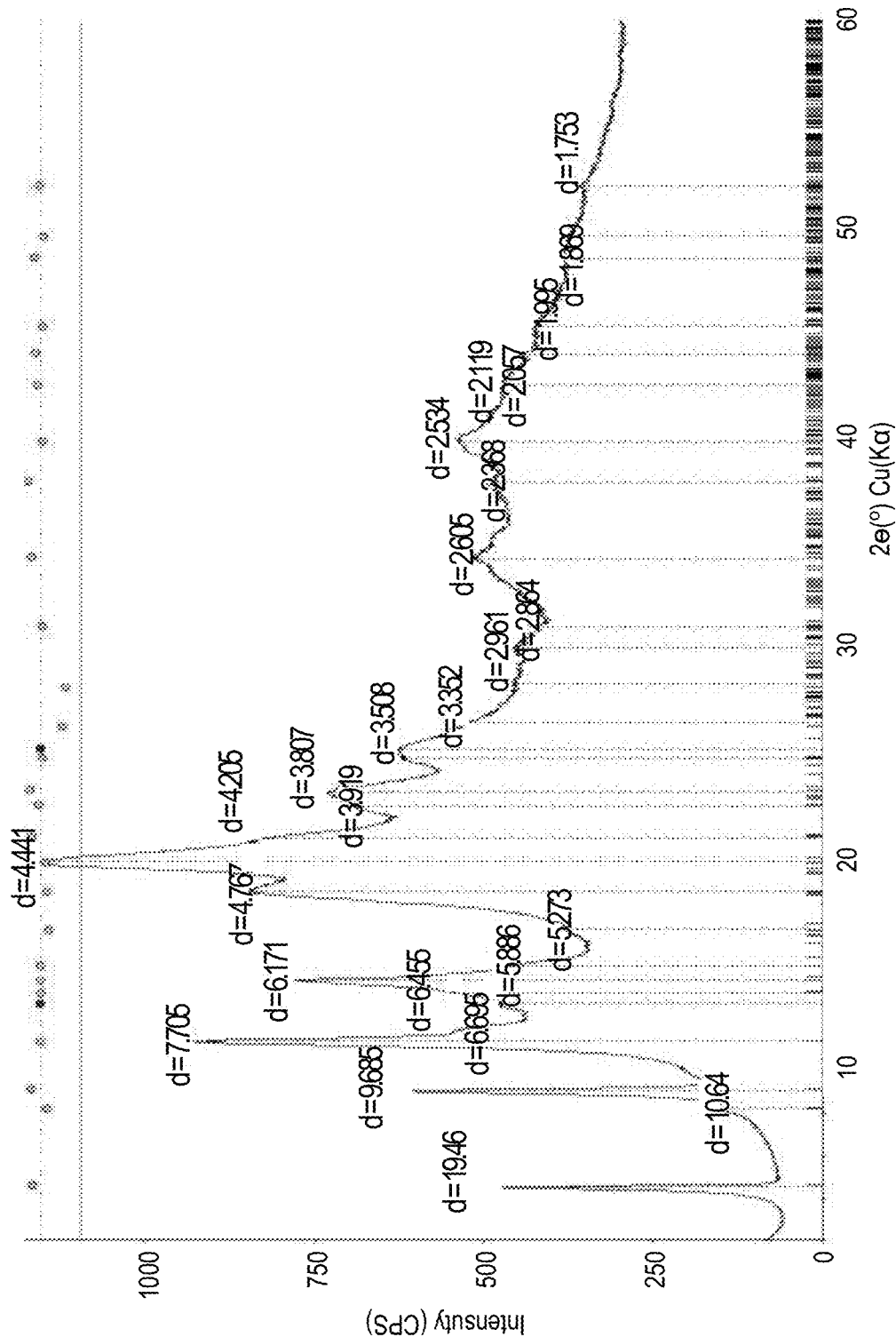
FIG. 9 shows representative XRD spectrum of NiClL1.

AFM measurements of NiClL1 and NiBrL2 confirmed the topologies and allowed precise measurement of the structure height (FIGS. 3A-3D), as well as determination of mechanical properties (materials and methods are available as supplementary materials on Science Online). The elastic modulus of NiClL1 measured by AFM nanoindentation is 5-6 GPa, which is similar to values reported for organic crystals (Roberts et al., 1991). The crystalline nature of these two MOFs was unambiguously demonstrated by SAED (FIGS. 25A-25D). XRD measurements of NiClL1 indicated also the formation of ordered structures (FIG. 9). The elemental composition of the MOFs was qualitatively confirmed by X-ray EDS, showing peaks corresponding to all characteristic atoms (nitrogen, metal and the anions) (FIGS. 7 and 26). The presence of the ligands is confirmed by FT-IR spectroscopy showing peaks corresponding to the ligand framework of NiClL1 and NiBrL2 that are shifted as compared to the free ligands (FIG. 5). The molecular structures of L1 and L2 are unlikely to be affected by the solvothermal conditions in the presence of these nickel salts. This assumption was verified by dissolving the MOFs under strong acidic conditions (pH<1), and subsequent isolation and characterization of the organic components. $^1H$ and $^{13}C\{^1H\}$ NMR spectroscopy (FIGS. 6 and 27), and mass-spectrometry (ESI-MS and MALDI-TOF) confirmed the ligand stability. SQUID measurements revealed paramagnetic behavior for both NiClL1 and NiBrL2. The ZFC and FC dependences were found to be superimposed (FIG. 20A, 21). These magnetic properties are in agreement with a near tetrahedral or an octahedral coordination geometry of the metal center (Bridgeman, 2008).

The isolated NiClL1 and NiBrL2 are air stable at RT in the dark for at least one year. Immersing these MOFs in DMF or water for several months does not induce any observable change in their microstructure. TGA of NiClL1 showed a relatively small weight decrease of 3.4% around 86° C. corresponding with the loss of $CHCl_3$ (FIG. 17). There was 30% weight loss at 1000° C. RTP of NiClL1 and NiBrL2 under a stream of 10% $H_2/N_2$ and subsequent SEM analysis indicated that the structures were retained at 200° C. Clear deformation for both NiClL1 and NiBrL2 was observed at higher temperatures (FIGS. 28A-28G and 29A-29F). The structures were found to be decorated with metallic nanoparticles ($\phi \approx 20$ nm) at ≥400° C. The topological stability of NiClL1 under vacuum is even higher, indicating that the thermal stability is affected by $H_2$.

Figure 18:
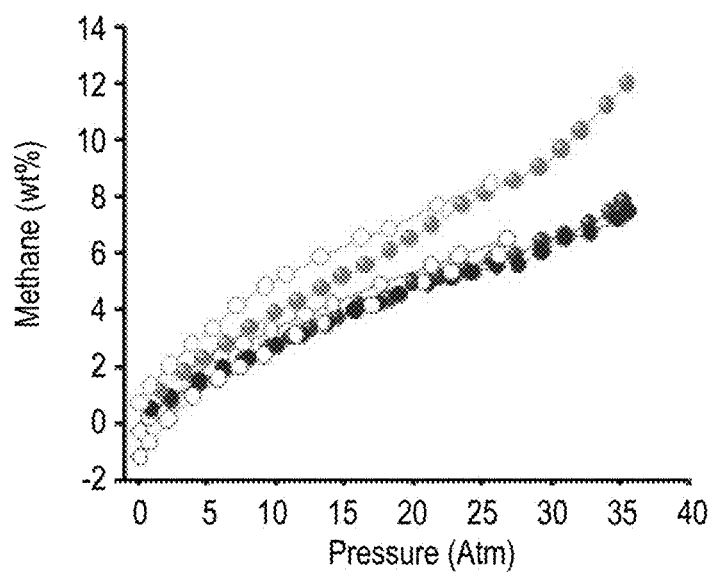
FIG. 18 shows methane adsorption-desorption isotherms for NiClL1. The sample was activated by vacuum treatment at 120° C. before exposing to methane at RT, 0° C. and −78.5° C. Adsorption (full red circle) and desorption (empty red circle) isotherms at RT. Adsorption (full blue circle) and desorption (empty blue circle) isotherms at 0° C. Adsorption (full green circle) and desorption (empty green circle) isotherm at −78.5° C.
Figure 19:
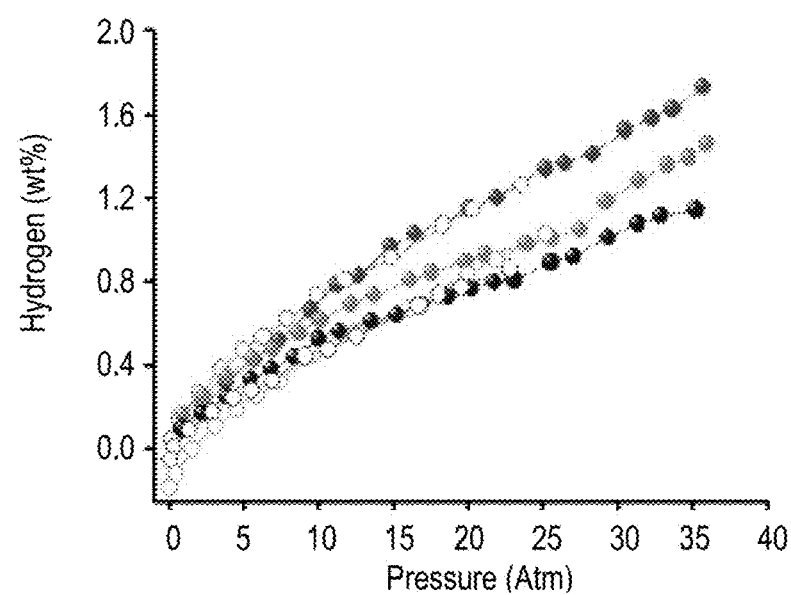
FIG. 19 shows adsorption isotherms (at 78.5K) for $H_2$ for NiClL1 activated at 70° C., 100° C. and 120° C. Adsorption (full red circle) and desorption (empty red circle) isotherms after activation at 70° C. Adsorption (full green circle) and desorption (empty green circle) isotherms after activation at 100° C. Adsorption (full blue circle) and desorption (empty blue circle) isotherms after activation at 120° C.

The porosity of NiClL1 was demonstrated by gas adsorption analysis. NiClL1 was activated at 120° C. under high vacuum for several hours to evaluate its adsorption/release efficiency for natural gas ($CH_4$). The $CH_4$ adsorption is 7.5 wt % at 0-20° C., and 11.7 wt % at −78.5° C. under a pressure of 35 atm. The hysteresis between adsorption and desorption runs is negligible, confirming the microporosity and the reversibility of the $CH_4$ uptake (FIG. 18). Gas pycnometry indicated a density of 0.687 g/cc. The $CH_4$ adsorption capacity of NiClL1 (75 $cm^3$ STP/$cm^3$) is in the range of that of COF-10, $Cd_2(AZPY)_3NO_3$, $Co_2(4,4'$-$BPY)_2(NO_3)_4$, $Cu_2(PIA)_2(NO_3)_4$ and the commerically available Basolite A520 (Manson et al., 2014; Adisa et al., 2012).

Figure 22A:
FIGS. 22A-22C show topologies of nickel chloride containing microstructures obtained by solvothermal synthesis.
Figure 22B:
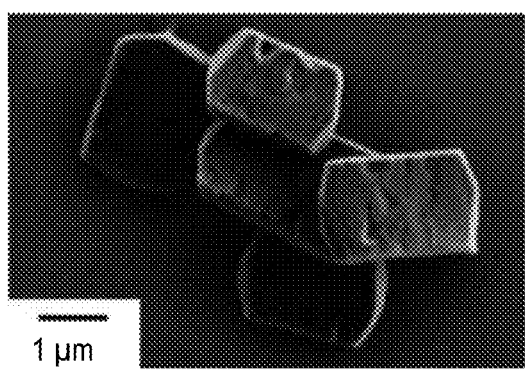
Figure 22C:
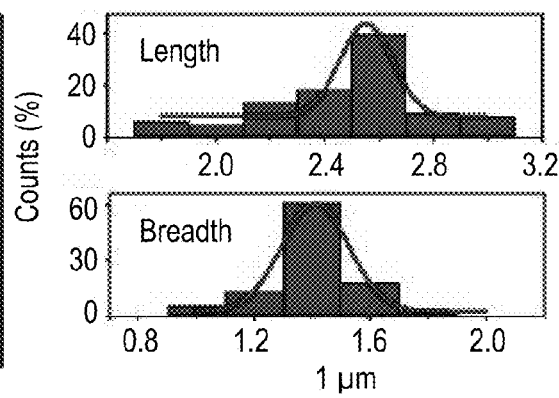
Figure 31:
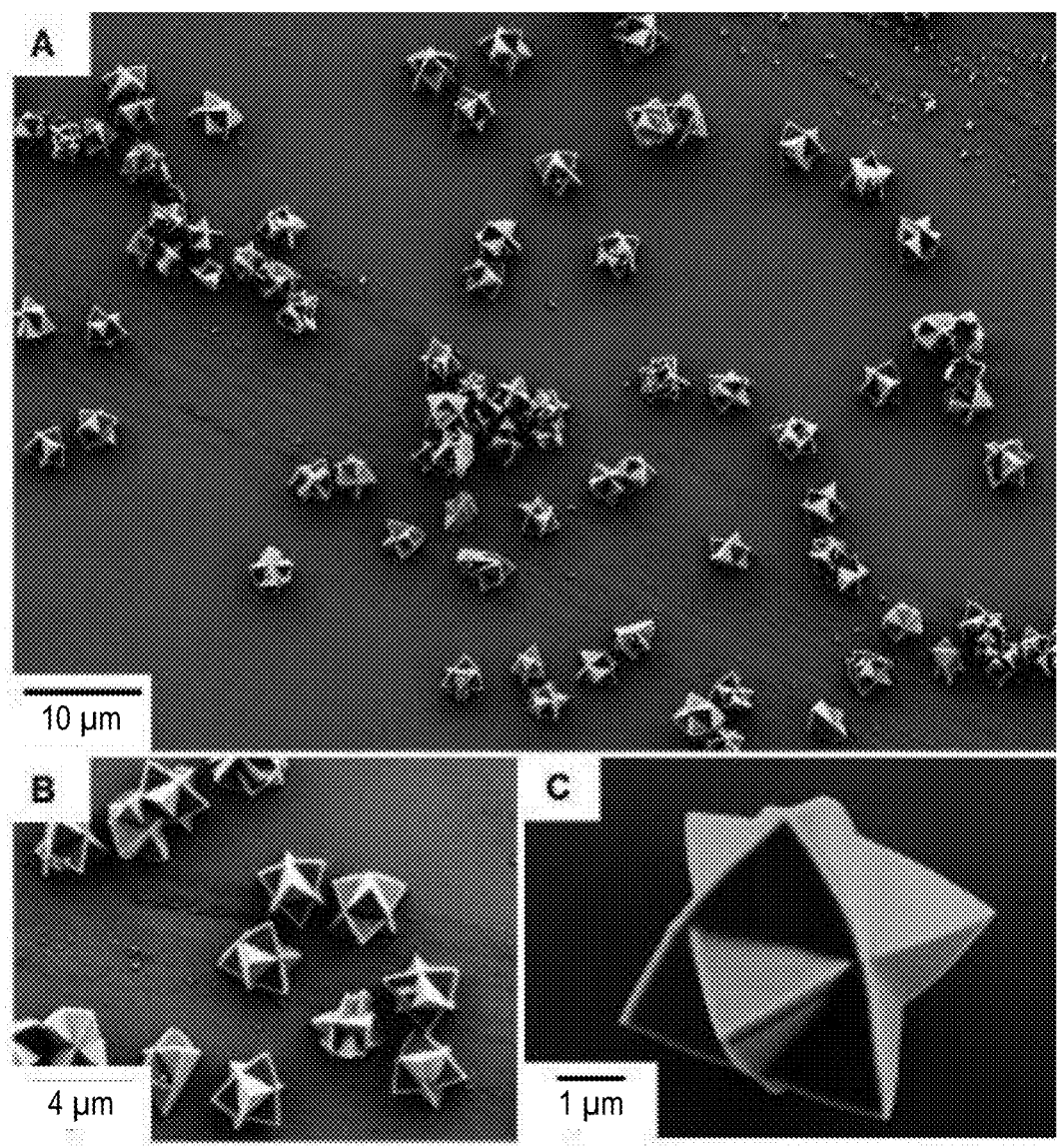
FIGS. 31A-31C shows interpenetrating topologies of Cu bromide containing MOFs obtained by solvothermal synthesis. SEM images (FIG. 31, panels A-C) of CuBrL2. Reaction conditions: $CuBr_2$:L2=2:1, $DMF/CHCl_3$=3:1 v/v, 105° C., 5 days.
Figure 32:
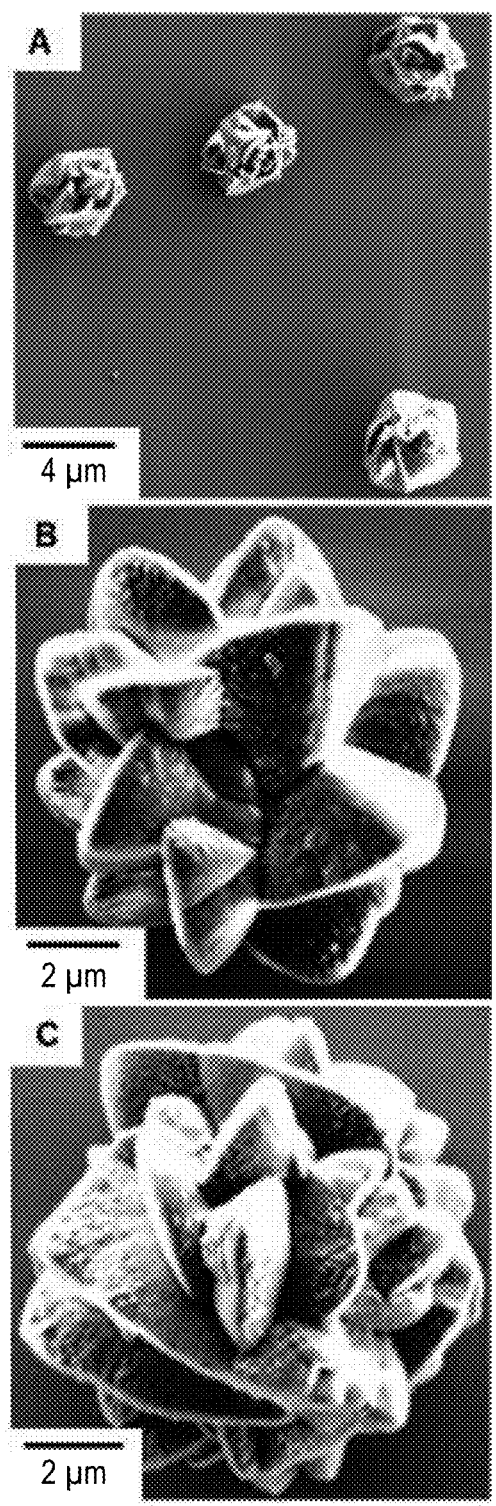
FIGS. 32A-32C shows interpenetrating topologies of Cu nitrate containing MOFs obtained by solvothermal synthesis. Representative SEM images (FIG. 32, panels A-C) of $Cu(NO_3)L2$. Reaction conditions: $Cu(NO_3)_2$:L2=1:1, $DMF/CHCl_3$=3:1 v/v, 105° C., 5 days.
Figure 33:
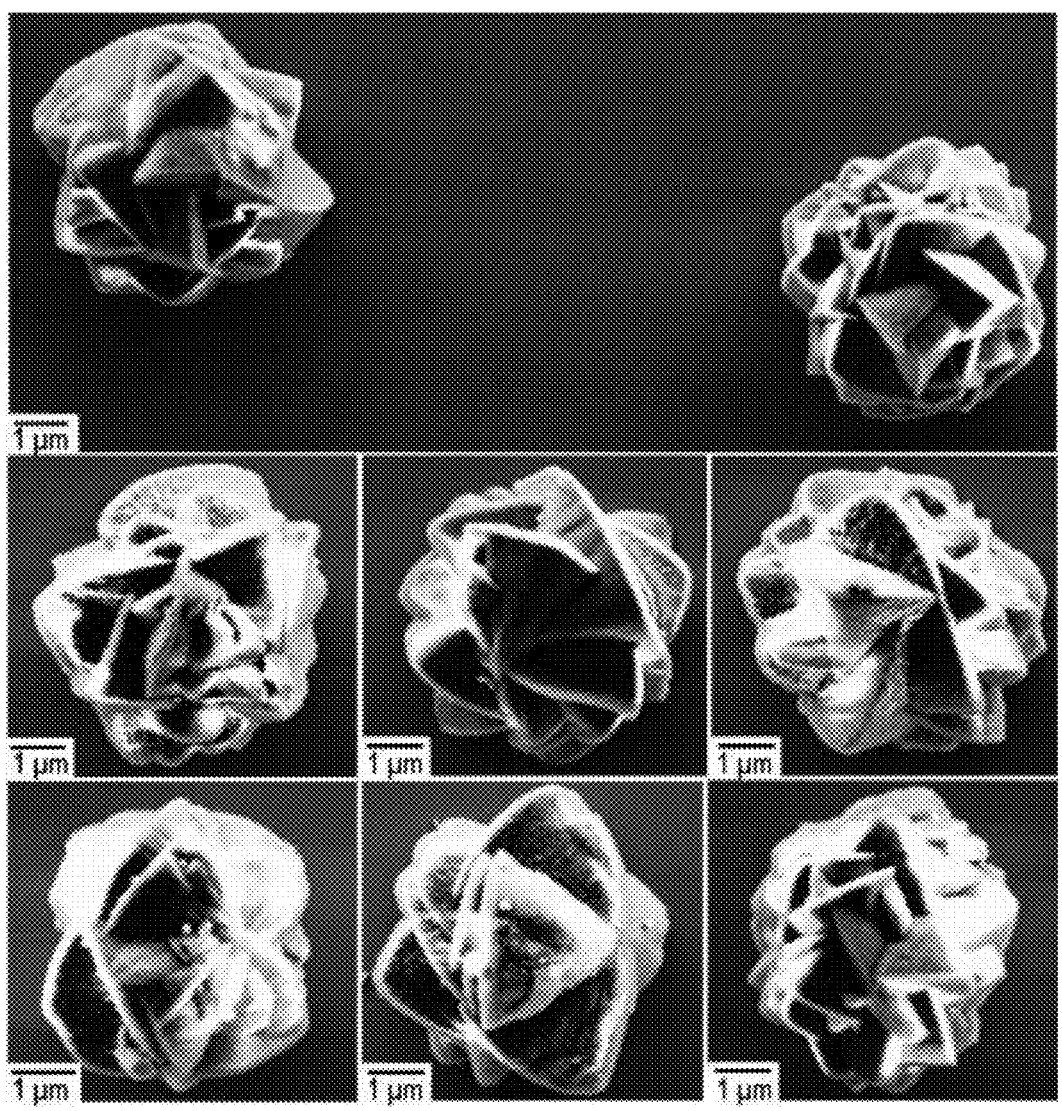
FIG. 33 shows examples of SEM images of $Cu(NO_3)L2$ (1 eq. L2, 1 eq. $Cu(NO_3)_2$, 3:1 (v/v) $DMF/CHCl_3$, 105° C., 5 days).

The use of Cu salts resulted in MOFs with strikingly differently structures. Non-uniform structured MOFs were obtained with $CuCl_2$ and L2 (FIG. 30). However, the reaction of $CuBr_2$ with L2 resulted in the formation of two interpenetrating tetrahedra (stella octangula) which can be described as a 3D extension of the Star of David (CuBrL2; FIGS. 31A-31C). The reaction conditions are identical to those used for the formation of NiClL1 and NiBrL2 (FIGS. 22A-22C). The crystalline nature of the Cu-based MOF was unequivocally confirmed by XRD; a powder XRD pattern similar to NiClL1 was obtained.

Figure 34A:
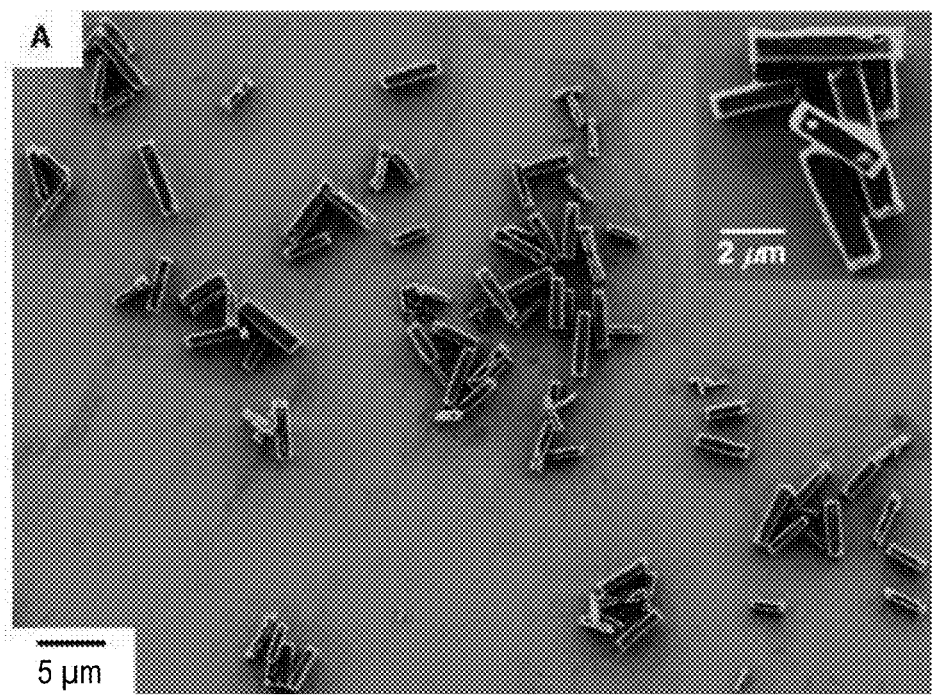
FIGS. 34A-34B show rectangular topologies of Cu nitrate containing MOFs obtained by solvothermal synthesis under inert atmosphere.
Figure 34B:
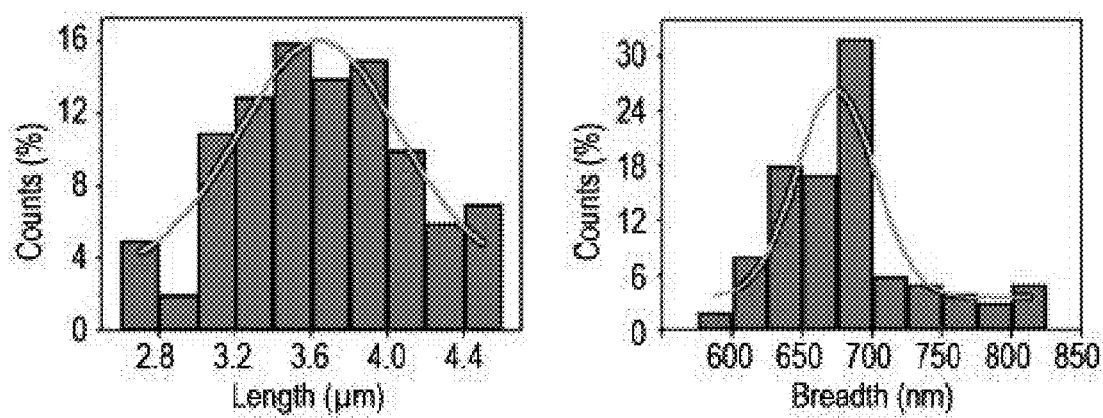
Figure 35:
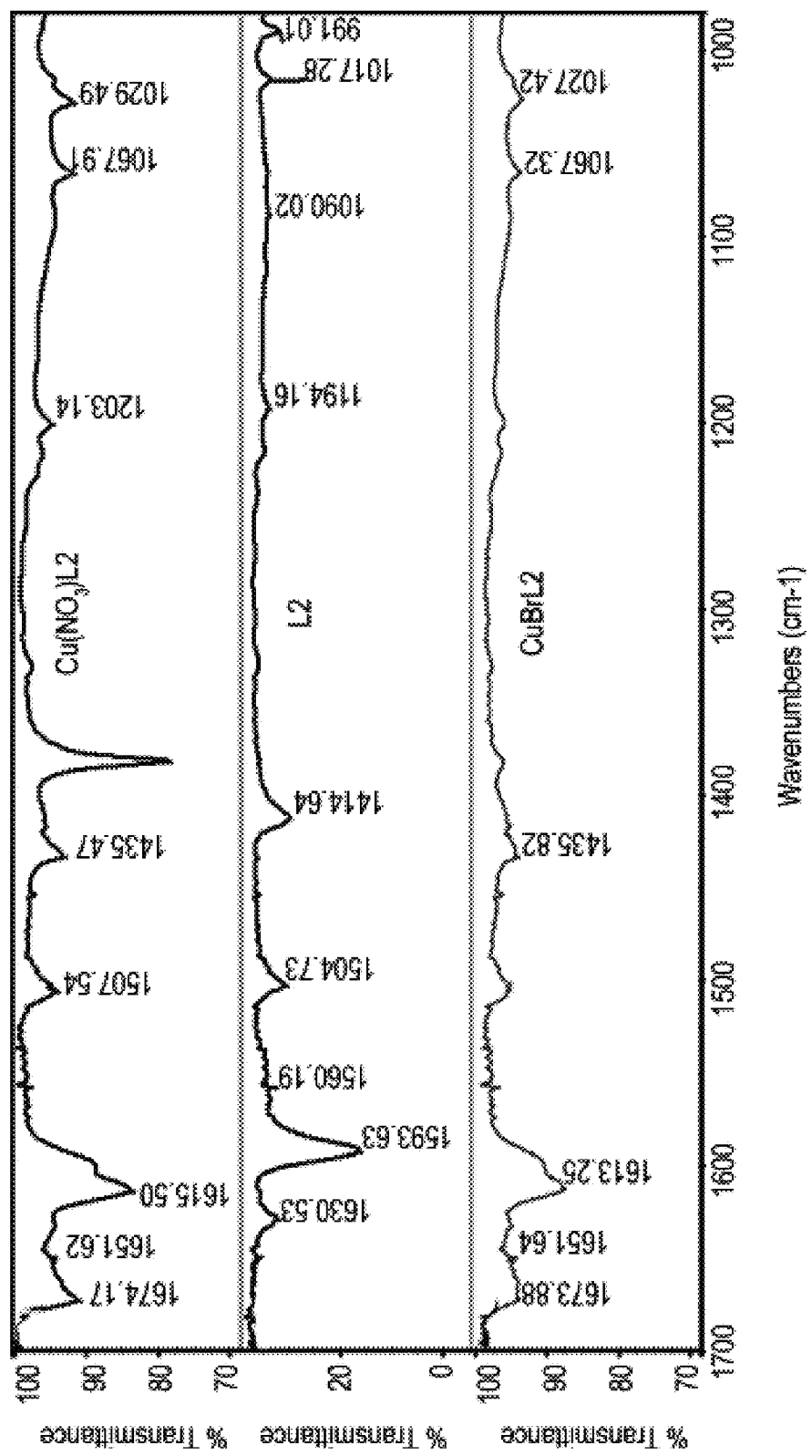
FIG. 35 shows FT-IR spectra of L2, $Cu(NO_3)L2$ and CuBrL2 (KBr pellet).

The nature of the anions and the metal-to-ligand ratio are also key parameters for the formation of well-defined Cu-based MOFs. The use of $Cu(NO_3)_2$ and a 1:2 (metal:L2) ratio resulted in ill-defined structures, contrasted with the higher degree of uniformity obtained for a 1:1 ratio. The latter resulted in flower-like topologies ($Cu(NO_3)L2$; FIGS. 32A-32C and FIG. 33). Interestingly, performing this reaction with rigorous exclusion of air and use of dry solvents resulted in the formation of rectangular prisms with an average length of 3.65±0.95 µm and breadth of 0.675±0.09 µm (Cu(NO$_3$)L2; FIGS. 34A-34b). In contrast to the other Cu-based MOFs, Cu(NO$_3$)L2 does not show any evidence of interpenetration. The presence and coordination of L2 is confirmed by FT-IR spectroscopy showing peaks corresponding to the ligand framework of CuBrL2 and Cu(NO$_3$)L2 (FIG. 35). Dissolving the Cu-based MOFs under acidic conditions, and subsequent isolation and characterization of L2 by NMR spectroscopy and mass-spectrometry confirmed its stability. The three Cu-based MOFs were found to be less uniform than NiClL1 and NiBrL2; however, they still have a common structural motif. The lesser degree of uniformity for the Cu-based MOFs might be related to their higher structural complexity and larger diversity of possible structures.

The formation of the MOFs is probably a result of a complex cascade of assembly processes (Spokoyny et al., 2009; Oh and Mirkin, 2005). For both Ni and Cu-based MOFs the solvent composition plays a crucial role as well for the generation of uniform structures (FIGS. 24A-24F, FIGS. 36A-36B and FIGS. 37A-37D). Varying the DMF/CHCl$_3$ ratios and/or addition of other solvents (PhCN, DMSO, water) leads to different assemblies.

Extending the electron microscope studies of the formation of the Ni- and Cu-based MOFs revealed interesting mechanistic information. A time-dependent analysis showed distinctly different pathways for the formation of the uniform structures obtained. Mixing the solutions of NiCl$_2$ and NiBr$_2$ salts with the corresponding ligand (L1 or L2) result in an immediate precipitation. Apparently, the process starts with the coordination of the ligand to the metal center as the first nucleation step as common in crystallizations and colloid synthesis. SEM analysis of NiClL1 aliquots taken immediately upon mixing showed the formation of a mixture of elongated (needles) and cubical structures (<1 µm; FIG. 38, panel A). Thermolysis of this mixture resulted in the formation of premature hexagonal structures, whose overall shape and size resembles the final product, but with coarse texture and edges (FIG. 38, panel B). Continuous heating for 5 days afforded the polished NiClL1 (FIGS. 23A-23C and FIG. 38, panel C). Amorphous infinite coordination polymers (ICP) reported by Mirkin undergo annealing similar to the structural polishing observed here (Spokoyny et al., 2009; Jeon et al., 2009). The rough surfaces are likely ideal nucleation sites for the addition of more material. A different growth process operates for the formation of NiBrL2. In the initial stages of mixing, small and uniform crystallites (≈55 nm×27 nm) are formed having the same topology as the final product (NiBRL2; FIGS. 23A-23C and FIG. 39, panel D). During the reaction, their size increases by almost fivefold (FIG. 38, panels D-E). For both the Ni-based MOFs, higher temperatures and pressure increases the average size of the nanostructures and decreases the number of smaller nanostructures. The higher surface energies of smaller structures can facilitate their dissolution generating new nuclei (Murray, et al., *Ibm. J. Res. & Dev.*, 2001, 45, 47-56). Unlike the observed polishing process with NiClL1, for NiBRL2 a different mechanism is operating that involves regular crystal growth by addition of material to the nuclei with retention of the same basic shape over the course of formation (akin to Ostwald ripening).

The time-dependent SEM analysis of the growth of the Cu-based MOFs revealed a rather complicated sequence involving several intermediate structures. Mixing a solution of CuBr$_2$ with L2 resulted at RT in non-uniform plate-like structures (FIG. 39, panel A) which transform into laterally fused spheres upon heating after 1.5 days (diameter=650±50 nm, FIG. 39, panel B). Upon continuous heating much larger diamond-like structures (FIG. 39, panel C) and fused structures thereof were observed. Some spherical structures remained, albeit smaller (FIG. 39, panel C, inset). Interestingly, after 3.5 days mostly pyramidal structures were present, most likely formed from a combination of fusion and nucleation (FIG. 39, panels D, D'). The inset of FIG. 39, panel D, clearly shows a penetrating twin-type structure. The initial pyramidal shapes are formed by fusion of the diamond-like structures (FIG. 39, panels C, D), and their facets subsequently act as nucleation sites to afford the kinetically complex products seen in FIG. 39, panel D'. Further heating results in the thermodynamically robust CuBrL2 (FIGS. 32A-32C and FIG. 39, panel E), that have the appearance of twinned crystals.

The formation of Cu(NO$_3$)L2 starts with the formation non-uniform plate-like structures similar to the ones observed for CuBrL2 (FIG. 40, panel A, inset). After heating for one day, irregular rectangular prisms were formed (FIG. 40, panel A), that transform after 2.5 days into interpenetrated structures (FIG. 40, panel B). Upon continued heating, these apparent threaded systems undergo another fusion process to provide the flower-like topologies (FIG. 40, panels C, D).

Our observations show that the formation of metal-organic microcrystals with a uniform size distribution can be readily achieved by solvothermal synthesis. Others have been using solvothermal approaches for attaining structural modifications mainly at the molecular level (Stock and Biswas, 2011). In addition, crystal packing variation through systematic chemical modifications is known for many organic and other materials (Stock and Biswas, 2011; Zhao, et al., *Acc. Chem. Res.* 2011, 44, 123-133; Smulders, et al., *Chem. Soc. Rev.* 2013, 42, 1728-1754; Wang, et al., *J. Am. Chem. Soc.* 2013, 135, 13222-13234; Shirman, et al., *Cryst. Growth Des.* 2008, 8, 3066-3072). However, such an approach to obtain uniform microcrystals is rare (Masoomi and Morsali, 2013; Ban, et al., *Microporous and Mesoporous Materials* 2013, 173, 29-36). It is remarkable that varying the intramolecular structure (i.e., C≡C vs. C=C, Cl vs. Br, Ni vs. Cu) has such a striking effect on the formation, uniformity and topology of the here reported MOFs. Our approach to obtain uniformity at the (sub)-micron level is sensitive to the position of the metal in the periodic table, as well as the reaction time. For example, we have shown previously that the reaction of Pd(II) salts with L2 resulted in the formation of coordination-polymer nanotubes (Kaminker et al., 2011). Structural features and dimensions of such nanotubes are assembly dependent as shown by Aida et al. (Zhang, et al., *Angew. Chem, Int. Ed.* 2009, 48, 4747-4750). In the present study, mixtures of (sub)-microstructures were observed initially which gradually transformed into the homogeneously structured crystals. Although this work has not attempted to characterize the factors, which predetermine the topology of such microstructures, the possibility of custom-designed topologies is enticing. Considering the range of parameters considered in this study, the possibility for shape-specificity and size uniformity in MOFs could be expected to be a wide and general phenomenon.

Example 3

Various Metal Organic Frameworks

In a series of experiments described herein below, various MOFs have been prepared using the general procedure described above, wherein different metal salts and reaction conditions are utilized.

Figure 41:
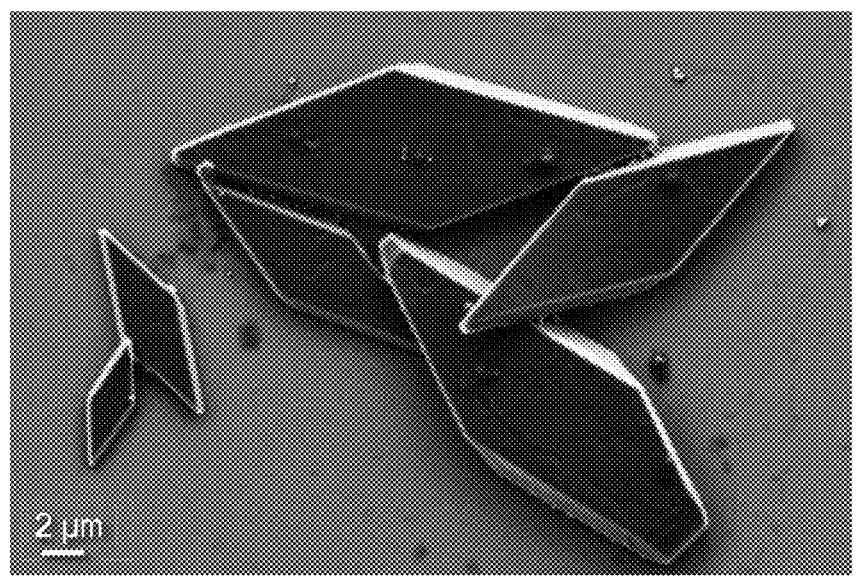
FIG. 41 shows MOFs prepared from a $CHCl_3$ solution of L1 and a DMF suspension of $NiBr_2$, under the conditions described in Study 3.

A CHCl$_3$ solution (1.0 ml) of L1 (5 mg, 6.9 µmol) was added to a DMF suspension (3.0 ml) of NiBr$_2$ (3 mg, 13.8 µmol) in an oven-dried glass pressure tube, which was sealed and heated for 5 days at 105° C. without stirring and with exclusion of light, followed by subsequent controlled cooling to RT over 9-10 h. at a rate of 10° C./h, resulting in a light green precipitate and was collected by centrifugation of the reaction mixture for ~10 min. at 5000 rpm and decanting the mother liquor (FIG. 41).

Figure 42:
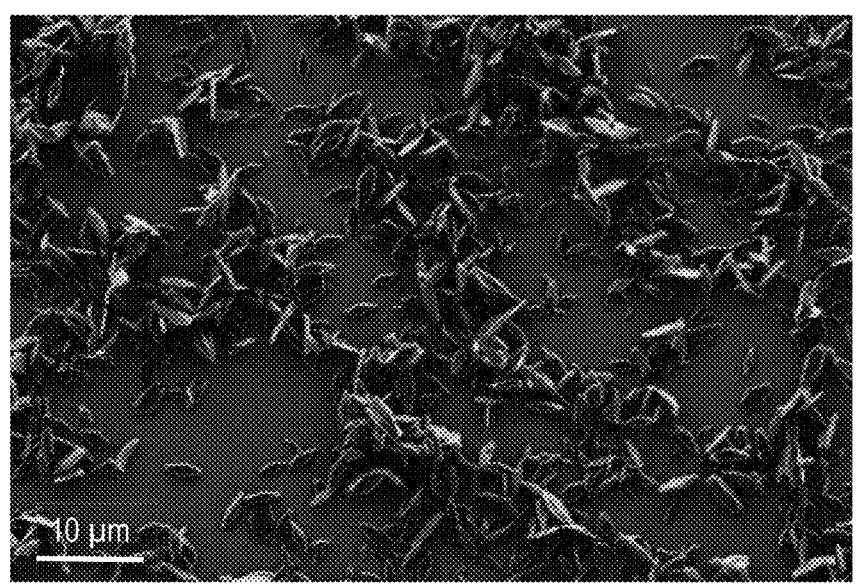
FIG. 42 shows MOFs prepared from a $CHCl_3$ solution of L1 and a DMF suspension of $NiCl_2.6H_2O$, under the conditions described in Study 3.

A CHCl$_3$ solution (2.0 ml) of L1 (5 mg, 6.9 µmol) was added to a DMF suspension (3.0 ml) of NiCl$_2$.6H$_2$O (3.3 mg, 13.8 µmol) in an oven-dried glass pressure tube, which was sealed and heated for 5 days at 105° C. without stirring and with exclusion of light, followed by subsequent controlled cooling to RT over 9-10 h. at a rate of 10° C./h, resulting in a light green precipitate and was collected by centrifugation of the reaction mixture for ~10 min. at 5000 rpm and decanting the mother liquor (FIG. 42).

A CHCl$_3$ solution (1.0 ml) of L2 (5.7 mg, 7.8 µmol) was carefully layered below a DMF solution (3.0 ml) of NiCl$_2$.6H$_2$O (1.9 mg, 7.8 µmol) in an oven-dried glass tube, which was sealed and kept in the dark for 5 d, resulting in a light green precipitate and was collected by centrifugation for ~10 min. at 5000 rpm and decanting the mother liquor (FIGS. 43A-43B).

A sonicated toluene solution (2.0 ml) of Pd(COD)Cl$_2$ (4.5 mg, 15.6 µmol) was added to a toluene suspension (4.0 ml) of L2 (5.7 mg, 7.8 µmol) in an oven-dried glass pressure tube, which was sealed and heated for 3 days at 105° C. without stirring and with exclusion of light, followed by subsequent controlled cooling to RT over 9-10 h. at a rate of 10° C./h, resulting in a yellowish precipitate and was collected by centrifugation of the reaction mixture for ~10 min. at 5000 rpm and decanting the mother liquor (FIGS. 44A-44B).

Figure 45:
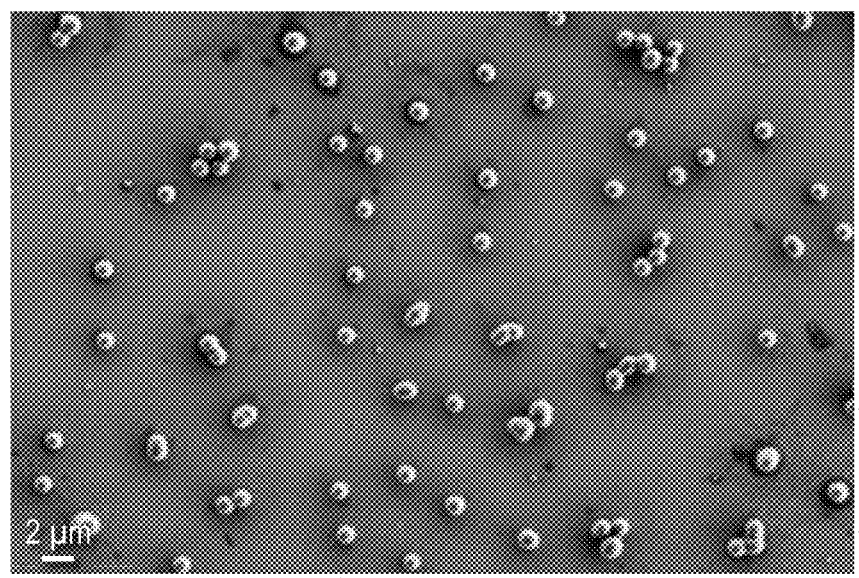
FIG. 45 shows MOFs prepared from a sonicated toluene suspension of $PdCl_2$ and a toluene suspension of L2, under the conditions described in Study 3.

A sonicated toluene suspension (2.0 ml) of PdCl$_2$ (2.8 mg, 15.6 µmol) was added to a toluene suspension (4.0 ml) of L2 (5.7 mg, 7.8 µmol) in an oven-dried glass pressure tube, which was sealed and heated for 3 days at 105° C. without stirring and with exclusion of light, followed by subsequent controlled cooling to RT over 9-10 h. at a rate of 10° C./h, resulting in a yellowish precipitate and was collected by centrifugation of the reaction mixture for ~10 min. at 5000 rpm and decanting the mother liquor (FIG. 45).

Figure 46:
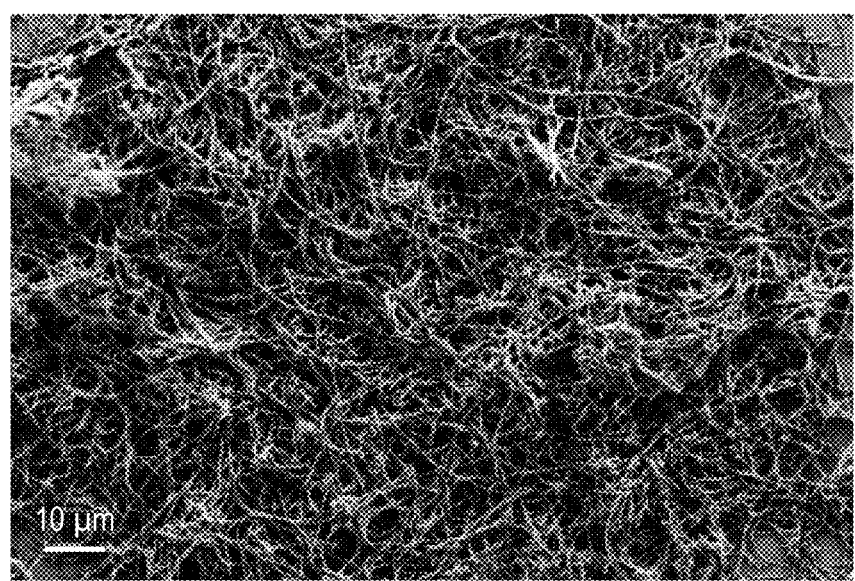
FIG. 46 shows MOFs prepared from an ethylbenzene solution of $Pd(PhCN)_2Cl_2$ and an ethylbenzene suspension of L2, under the conditions described in Study 3.

An ethylbenzene solution (2.0 ml) of Pd(PhCN)$_2$Cl$_2$ (5 mg, 15.6 µmol) was added to an ethylbenzene suspension (4.0 ml) of L2 (5.7 mg, 7.8 µmol) in an oven-dried glass pressure tube, which was sealed and heated for 3 days at 105° C. without stirring and with exclusion of light, followed by subsequent controlled cooling to RT over 9-10 h. at a rate of 10° C./h, resulting in a yellowish precipitate and was collected by centrifugation of the reaction mixture for ~10 min. at 5000 rpm and decanting the mother liquor (FIG. 46).

A toluene solution (3.0 ml) of Pd(PhCN)$_2$Cl$_2$ (5 mg, 15.6 µmol) was added to a heptane suspension (3.0 ml) of L2 (5.7 mg, 7.8 µmol) in an oven-dried glass pressure tube, which was sealed and heated for 3 days at 105° C. without stirring and with exclusion of light, followed by subsequent controlled cooling to RT over 9-10 h. at a rate of 10° C./h, resulting in a yellowish precipitate and was collected by centrifugation of the reaction mixture for ~10 min. at 5000 rpm and decanting the mother liquor (FIG. 47).

A CHCl$_3$ solution (1.0 ml) of L2 (5.7 mg, 7.8 µmol) was carefully layered below a DMF solution (3.0 ml) of Cu(OTf)$_2$ (2.8 mg, 7.8 µmol) in an oven-dried glass tube, which was sealed and kept in the dark for 5 d, resulting in a light blue precipitate and was collected by centrifugation of the reaction mixture for ~10 min. at 5000 rpm and decanting the mother liquor (FIGS. 48A-48B).

A CHCl$_3$ solution (1.0 ml) of L2 (5.7 mg, 7.8 µmol) was carefully layered below a DMF solution (3.0 ml) of Cu(OTf)$_2$ (2.8 mg, 7.8 µmol) in an oven-dried glass tube, which was sealed and kept in the dark for 10 days and then heated for another 2 days at 60° C. without stirring and with exclusion of light, followed by subsequent cooling to RT temperature, resulting in a light blue precipitate and was collected by centrifugation of the reaction mixture for ~10 min. at 5000 rpm and decanting the mother liquor (FIG. 49).

A dry CHCl$_3$ solution (1.0 ml) of L2 (5 mg, 6.8 µmol) was added to a dry DMF solution (3.0 ml) of Cu(NO$_3$)$_2$.3H$_2$O (1.65 mg, 6.8 µmol) in an oven-dried glass pressure tube under N$_2$ atmosphere, which was sealed and heated for 6 days at 105° C. without stirring and with exclusion of light, followed by subsequent controlled cooling to RT over 9-10 h. at a rate of 10° C./h, resulting in a light green precipitate and was collected by centrifugation of the reaction mixture for ~10 min. at 5000 rpm and decanting the mother liquor (FIGS. 50A-50B).

A CHCl$_3$ solution (1.0 ml) of L2 (5 mg, 6.8 µmol) was added to a DMF solution (3.0 ml) of Zn(OAc)$_2$.2H$_2$O (3 mg, 13.6 µmol) in an oven-dried glass pressure tube, which was sealed and heated for 2 days at 105° C. without stirring and with exclusion of light, followed by subsequent controlled cooling to RT over 9-10 h. at a rate of 10° C./h, resulting in a light white precipitate and was collected by centrifugation of the reaction mixture for ~10 min. at 5000 rpm and decanting the mother liquor (FIG. 51).

A CHCl$_3$ solution (1.0 ml) of L2 (5 mg, 6.8 µmol) was added to a DMF solution (3.0 ml) of Zn(OAc)$_2$.2H$_2$O (3 mg, 13.6 µmol) in an oven-dried glass pressure tube, which was sealed and heated for 3 days at 105° C. without stirring and with exclusion of light, followed by subsequent controlled cooling to RT over 9-10 h. at a rate of 10° C./h, resulting in a light white precipitate and was collected by centrifugation of the reaction mixture for ~10 min. at 5000 rpm and decanting the mother liquor (FIGS. 52A-52B).

Figure 53:
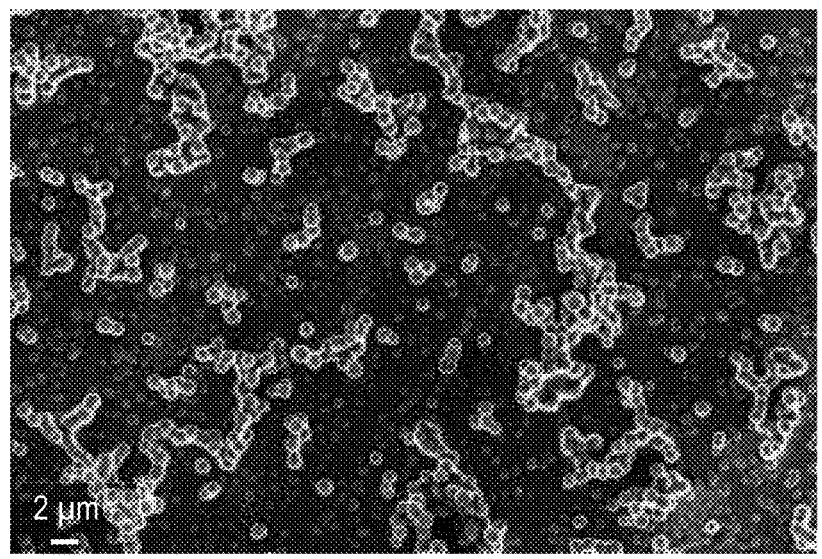
FIG. 53 shows MOFs prepared from a $CHCl_3$ solution of L2 and a DMF solution of $ZnCl_2.2H_2O$, under the conditions described in Study 3.

A CHCl$_3$ solution (1.0 ml) of L2 (5 mg, 6.8 µmol) was added to a DMF solution (3.0 ml) of ZnCl$_2$.2H$_2$O (0.92 mg, 6.8 µmol) in an oven-dried glass pressure tube, which was sealed and heated for 3 days at 105° C. without stirring and with exclusion of light, followed by subsequent controlled cooling to RT over 9-10 h. at a rate of 10° C./h, resulting in a light white precipitate and was collected by centrifugation of the reaction mixture for ~10 min. at 5000 rpm and decanting the mother liquor (FIG. 53).

Figure 54:
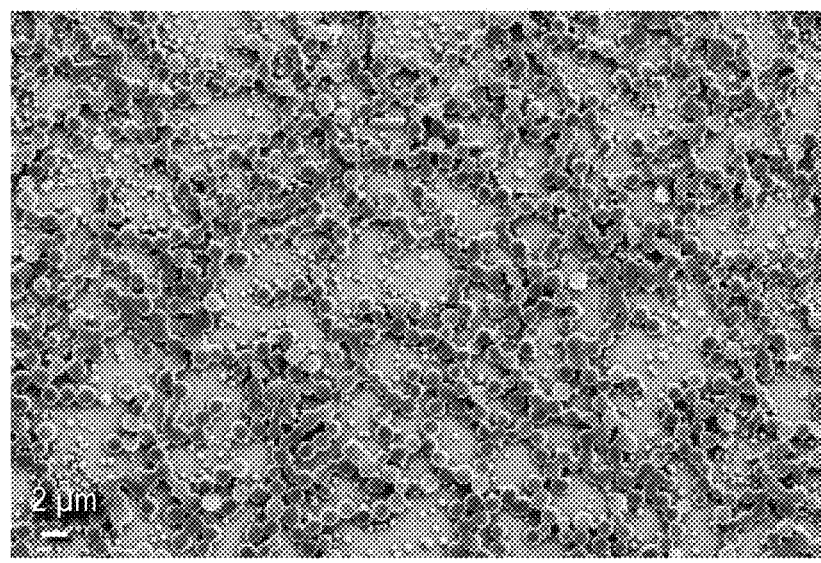
FIG. 54 shows MOFs prepared from a $CHCl_3$ solution of L2 and a DMF solution of $ZnCl_2.2H_2O$, under the conditions described in Study 3.

A CHCl$_3$ solution (1.0 ml) of L2 (5 mg, 6.8 µmol) was added to a DMF solution (3.0 ml) of ZnCl$_2$.2H$_2$O (1.86 mg, 13.6 µmol) in an oven-dried glass pressure tube, which was sealed and heated for 2 days at 105° C. without stirring and with exclusion of light, followed by subsequent controlled cooling to RT over 9-10 h. at a rate of 10° C./h, resulting in a light white precipitate and was collected by centrifugation of the reaction mixture for ~10 min. at 5000 rpm and decanting the mother liquor (FIG. 54).

Figure 55:
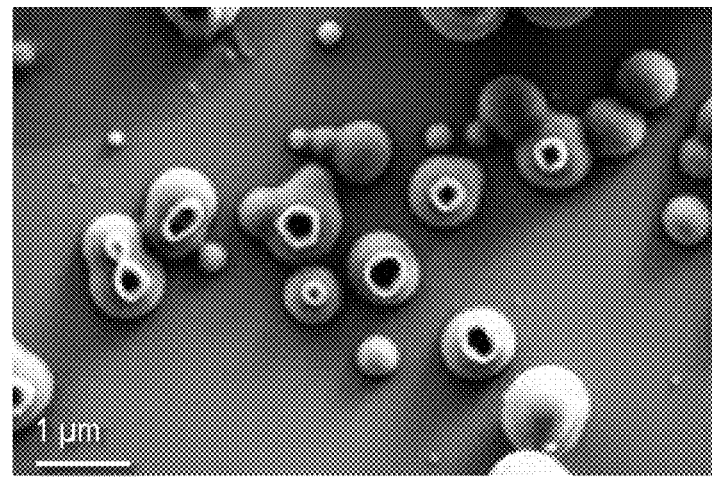
FIG. 55 shows MOFs prepared from a $CHCl_3$ solution of L2 and a DMF solution of $ZnCl_2.2H_2O$, under the conditions described in Study 3.

A CHCl$_3$ solution (1.0 ml) of L2 (5 mg, 6.8 µmol) was added to a DMF solution (3.0 ml) of ZnCl$_2$.2H$_2$O (1.86 mg, 13.6 µmol) in an oven-dried glass pressure tube, which was sealed and heated for 3 days at 105° C. without stirring and with exclusion of light, followed by subsequent controlled cooling to RT over 9-10 h. at a rate of 10° C./h, resulting in a light white precipitate and was collected by centrifugation of the reaction mixture for ~10 min. at 5000 rpm and decanting the mother liquor (FIG. 55).

Figure 56:
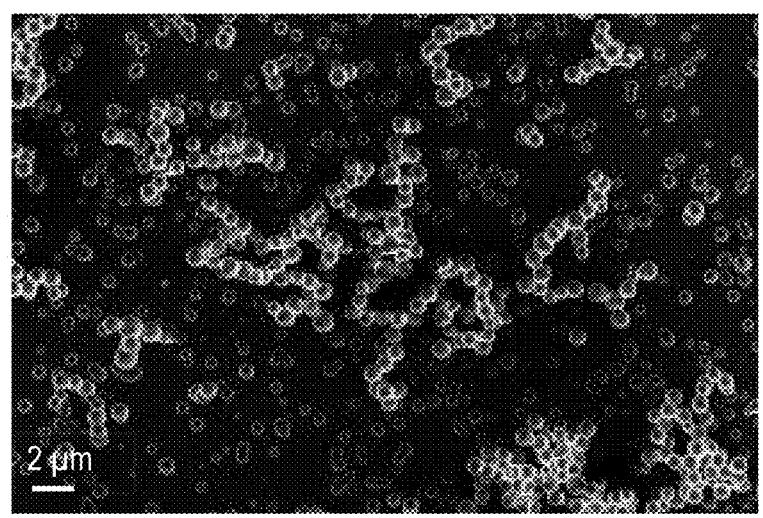
FIG. 56 shows MOFs prepared from a $CHCl_3$ solution of L2 and a DMF solution of $ZnBr_2$, under the conditions described in Study 3.

A CHCl$_3$ solution (1.0 ml) of L2 (5 mg, 6.8 µmol) was added to a DMF solution (3.0 ml) of ZnBr$_2$ (3.1 mg, 13.6 µmol) in an oven-dried glass pressure tube, which was sealed and heated for 2 days at 105° C. without stirring and with exclusion of light, followed by subsequent controlled cooling to RT over 9-10 h. at a rate of 10° C./h, resulting in a white precipitate and was collected by centrifugation of the reaction mixture for ~10 min. at 5000 rpm and decanting the mother liquor (FIG. 56).

Example 4

L4-NiBr

A CHCl$_3$ solution (1.0 ml) of L4 (5 mg, 5.9 µmol, 1 equiv.) was added to a DMF suspension (2.0 ml) of NiBr$_2$ (2.6 mg, 11.7 µmol, 2 equiv.) in an oven-dried glass pressure tube, which was sealed and heated for 42 hours at 105° C. without stirring and with exclusion of light, followed by subsequent controlled cooling to RT over 9-10 h. at a rate of 10° C./h, resulting in a light green-yellow precipitate and was collected by centrifugation of the reaction mixture for ~10 min. at 4000 rpm and decanting the mother liquor. The powder was washed twice with 1 mL of DMF. The reaction yielded 5.2 mg of L4-NiBr.

The crystal structures were relatively uniform in shape and size with a mean diagonal length of 0.741 µm. (FIG. 57, panel A). These structures are crystalline, since the lattice planes can be seen by high-resolution TEM (FIG. 57, panel B). Using reduced FFT and measuring the diffraction pattern distance, the lattice plane distance was 1.79 nm. with inset: FFT of the lattice planes. FIG. 57, panel C is a TEM image of L4-NiBr. FIG. 57, panel D is a histogram showing the size distribution of L4-NiBr with an average diagonal of 0.741 µm.

After 42 h of heating at 105° C., the structures change into a "barrel-shaped" L4-NiBr with a mean length of 2.49±0.81 µm (FIG. 58, panel A). High-magnification TEM images of the L4-NiBr showed lattice planes and using image analyses on the lattice plane image d-distance of the lattice planes was calculated to be 13.7 Å; inset: top-diffraction pattern of L4-NiBr, bottom-TEM image of L4-NiBr (FIG. 58, panel B). Selected area electron diffraction pattern (SAED pattern) supports that the particles are crystalline. A histogram showed the size distribution of L4-NiBr of width 1.01 µm, and length 2.49 µm (FIG. 58, panel C).

High-angle annular dark field (HAADF) STEM images show that the structure has an onion layered form, "shells" of crystals that are build one on top of the other all around (FIG. 59, panel A and 59, panel B, indicated by arrows). Elemental mapping, using STEM, showed the presence of the different elements that make up L4-NiBr including Ni, Br, N, C, O, and Cl (FIG. 59, panel C). Chlorine comes from using chloroform as part of the solvent reaction mixture.

Chloroform was probably trapped in the pores of the framework. An anion exchange on the metallic center is not likely since throughout the heating process the ratio between nickel and bromide remains 1:2. The growth of the L4-NiBr was faster than was initially estimated. The "barrel-like" structures were obtained after only 2 h of heating, yet they were larger than the final product and were not uniform in their size (FIG. 60, panel B and FIG. 60, panel E). After 12 h of heating, the final structure obtained remained the same size and shape until the end of the 42 h of heating (FIG. 60, panel A, FIG. 60, panel C, and FIG. 60, panel D). The crystallization process involved both classic and reverse Ostwald ripening and resulted in a wide particle size distribution (PSD) as observed from t=0 to t=2 h, where the structures become much larger than in t=0, but with poor size uniformity. After 12 h of heating, the structures reduced in size and the PSD narrowed as comparison to t=2 h. (FIG. 60, panel F).

Example 5

L4-NiNO$_3$

A CHCl$_3$ solution (1.0 ml) of L4 (5 mg, 5.9 µmol, 1 equiv.) was added to a DMF suspension (2.0 ml) of Ni(NO$_3$)$_2$ (3.4 mg, 11.7 µmol, 2 equiv.) in an oven-dried glass pressure tube, which was sealed and heated for 42 hours at 105° C. without stirring and with exclusion of light, followed by subsequent controlled cooling to RT over 9-10 h. at a rate of 10° C./h, resulting in a yellow-green precipitate and was collected by centrifugation of the reaction mixture for ~10 min. at 4000 rpm and decanting the mother liquor. The powder was washed twice with 1 mL of DMF. The reaction yielded 5.7 mg of L4-NiNO$_3$. (FIG. 61, panel A). The energy dispersive X-ray spectra is shown in FIG. 61, panel B.

After heating the L4-NiNO$_3$ material obtained above for 42 hours, the material became egg-shaped with a mean length of 1.97 µm and a width of 1.13 µm. (FIG. 62, panel A, and FIG. 62, panel B). The SEAD pattern showed diffractions with a d-distance of 13.0 Å (line, FIG. 62, panel B inset) that indicated the particles were crystalline.

Example 6

L4-CuNO$_3$

A CHCl$_3$ solution (1.0 ml) of L4 (5 mg, 5.86 µmol) was added to a DMF suspension (2.0 ml) of Cu(NO$_3$)$_2$ (2.8 mg, 11.7 µmol, 2 equiv.) in an oven-dried glass pressure tube, which was sealed and heated for 42 hours at 105° C. without stirring and with exclusion of light, followed by subsequent controlled cooling to RT over 9-10 h. at a rate of 10° C./h, resulting in a light blue (later green upon heating) precipitate and was collected by centrifugation of the reaction mixture for ~10 min. at 4000 rpm and decanting the mother liquor. The powder was washed twice with 1 mL of DMF. The reaction yielded 4.7 mg of L4-CuNO$_3$.

Once the material was heated for 42 h, the material changed color to green and the hexagonal prisms formed. The crystals formed were 4.83 µm long with edges of 1.68 µm as shown in SEM images. (FIG. 63, panel A). FIG. 63, panel B illustrates TEM images of the crystal lattice of L4-CuNO$_3$ and reduced FFT determined the d-distance at 13.9 Å.

Single crystal XRD of L4-CuNO$_3$ revealed that copper was coordinated to four pyridine groups in a square-planar geometry with a Cu-py distance of 2.0 Å and water oxygens 2.815 Å above and below the copper, in a total Jan-Teller distorted octahedral geometry. (FIG. 64, panel A). The voids (colored pale blue outside and dark blue in the inside, FIG. 64, panel B and panel C, and marked as A and B in FIG. 64, panel E) occupied two regions of approximately 8% and 31% of total volume, area of 300 Å and 1228.6 Å, respectively. The approximated Cu—Cu distances were either 8.3 Å (closest) or 18.5 Å (most distant). FIG. 64, panel D illustrates the unit cell of L4-CuNO$_3$. FIG. 64, panel F is a representative SEM image of the crystal measured.

Example 7

L4-NiBr/L4-NiNO$_3$

A CHCl$_3$ solution (1.0 ml) of L4 (5 mg, 5.86 µmol) was added to a DMF suspension (2.0 ml) of NiBr$_2$ and NiNO$_3$ (11.72 µmol) in an oven-dried glass pressure tube, which was sealed and heated for 42 hours at 105° C. without stirring and with exclusion of light, followed by subsequent controlled cooling to RT over 9-10 h. at a rate of 10° C./h, resulting in precipitate and collected by centrifugation of the reaction mixture for ~10 min. at 4000 rpm and decanting the mother liquor. The powder was washed twice with 1 mL of DMF. In all intermediate reactions, an initial precipitate appeared only after a few minutes of heating at 105° C., similar to L4-NiNO$_3$ (FIG. 65, panels A-F). Only with 100% NiBr (L4-NiBr) an immediate precipitate appeared at room temperature (FIG. 65, panel F). There excess NiBr$_2$ was necessary to obtain the cut barrel-like edges, characteristic of L4-NiBr. FIG. 65 illustrates drop-casting of the reaction mixture immediately upon mixing L4 and NiBr$_2$ and Ni(NO$_3$)$_2$. FIG. 65 panel A 100% NO$_3^-$; FIG. 65, panel B 85% NO$_3^-$ 15% Br$^-$, FIG. 65, panel C 50% NO$_3^-$ 50% Br$^-$, FIG. 65, panel D 25% NO$_3^-$ 75% Br$^-$, FIG. 65, panel E 15% NO$_3^-$ 85% Br$^-$, and FIG. 65, panel F 100% Br$^-$.

The different ratios of the anion had a larger effect on the final MOFs obtained (FIG. 66). By using 15% of nitrate and 85% of bromide, the egg-shaped L4-NiNO$_3$ structures were reduced in length, from 1.97 μm to 1.14 μm. FIG. 66, panel A and panel B. Conversion of 50% of nitrate to bromide resulted in elongated ellipsoid-shaped structures with non-uniform size (FIG. 66, panel C). Conversion of 75% of nitrate with bromide, so that the bromide was the dominant anion resulted in barrel-shaped MOFs (the same as with L4-NiBr, but larger in both length and width). FIG. 66, panel D. The size of the MOF continued to decrease as the percentage of nitrate decreased. FIG. 66, panel E and Panel F. FIG. 66, panel G graphically illustrates the average size (first column) and width (second column) vs. anion content.

Example 8

Mixed Metal Systems

Following the reaction conditions of examples 4-7, a metal gradient reaction sequence was carried out keeping the M/L ratio at 2:1, and the percentage of each metal (nickel or copper) was changed. In all reactions an immediate light blue precipitate appeared, similar to the L4-CuNO$_3$ system. The morphology of the initial precipitate became defined in its shape and size as the amount of nickel in the system increased. FIG. 67 illustrates the effect. Drop-casting of the reaction mixture immediately upon mixing L4 and nitrate salts of copper and nickel is illustrated in FIG. 67. FIG. 67, panel A 100% Cu$^{2+}$; FIG. 67, panel B 85% Cu$^{2+}$ 15% Ni$^{2+}$; FIG. 67, panel C 75% Cu$^{2+}$ 25% Ni$^{2+}$; FIG. 67, panel D 50% Cu$^{2+}$ 50% Ni$^{2+}$; FIG. 67, panel E 25% Cu$^{2+}$ 75% Ni$^{2+}$; FIG. 67, panel F 15% Cu$^{2+}$ 85% Ni$^{2+}$; and FIG. 67, panel G 100% Ni$^{2+}$. The scale bar in FIG. 67, panels A-G=1 μm.

Each reaction was heated for 42 h, and all reactions with the Ni—Cu mix had the hexagonal prism morphology as found in L-CuNO$_3$. The amounts of metal in the final structure were measured by EDS in the SEM and compared to the amounts used for the reaction. The correlation for the amount of metal is illustrated in FIG. 68. FIG. 68 panel A 100% Cu$^{2+}$; FIG. 68, panel B 85% Cu$^{2+}$ 15% Ni$^{2+}$; FIG. 68, panel C 75% Cu$^{2+}$ 25% Ni$^{2+}$; FIG. 68, panel D 50% Cu$^{2+}$ 50% Ni$^{2+}$; FIG. 68, panel E 25% Cu$^{2+}$ 75% Ni$^{2+}$; FIG. 68, panel F 15% Cu$^{2+}$ 85% Ni$^{2+}$; and FIG. 68, panel G 100% Ni$^{2+}$. The scale bar in FIG. 68, panels A-G=1 μm.

The less copper in the system, the shorter the structures became. The structures kept their uniformity until nickel was the major metal (75% Ni$^{2+}$); thereafter the uniformity was lost, although the majority of the crystals were smaller in size than they were in the 50-50 Ni—Cu, thus, the trend of size reduction in length was maintained.

Example 8

MOF with TOAB AuNP

A silicon 0.5×0.5 cm2 substrate (100 MM/CZ/1-0-0/BORON/P type/Resistance 10.0000-20.0000/thickness 500-550/Oxygen 0.00-0.00) was drop-casted with a L4-NiBr, L4-NiNO$_3$ or L4-CuNO$_3$ reaction mixture, without DMF washing, and the solvents were allowed to evaporated in air. A drop of TOAB-capped AuNPs (0.035 μM) in toluene, that were synthesized using the procedure described by Boterashvili et al., (*Angew. Chem. Int. Ed.* 2012, 51, 12268-12271) was casted on the MOF containing substrate and reacted under air. After 30 min. the remaining AuNP-solution was removed with a Kimwipe and the residue was washed twice with toluene, and measured by SEM after 24 h at room temperature in air. The AuNP-coated MOFs were heated to 150° C. for 6 and 20 h. on a hot plate in air and examined immediately by SEM.

Reacting L4-NiBr with TOAB gold nanoparticles (FIG. 69, panel A), the MOF was coated with a layer of AuNPs, whereas the silicon substrate was not as seen in SEM images taken (FIG. 69, panel A and panel B). The AuNPs originally 5 nm diameter fused into larger particles, and attached to the MOF surface. The AuNP covered MOFs were heated to 150° C. degrees in air for 6 h (FIG. 69, panel C) and 20 h (FIG. 69, panel D). The scale of the panels equals 1 μm. The surface particles fused to form larger particles; the binding of the AuNPs to the MOF was strong to prevent the NPs from merging to even larger (and fewer) aggregates.

Reacting L4-NiNO$_3$ (FIG. 70, panel A) with TOAB-capped AuNPs, the MOF was coated with a layer of AuNPs (FIG. 70, panel B). Once the material was heated to 150° C., the AuNP particles on the surface increased in size and decreased in number after 6 hours (FIG. 70, panel C) and after 20 hours (FIG. 70, panel D). The scale bar in the panels equals 1 μm.

Example 9

Synthesis of Ligand L3

Ligand L3 was prepared by the synthetic route shown in the following scheme.

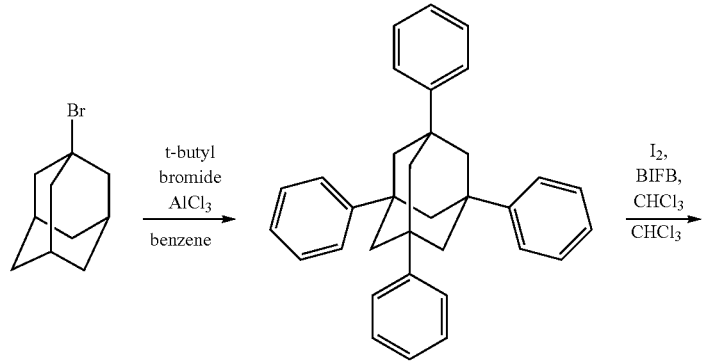

-continued
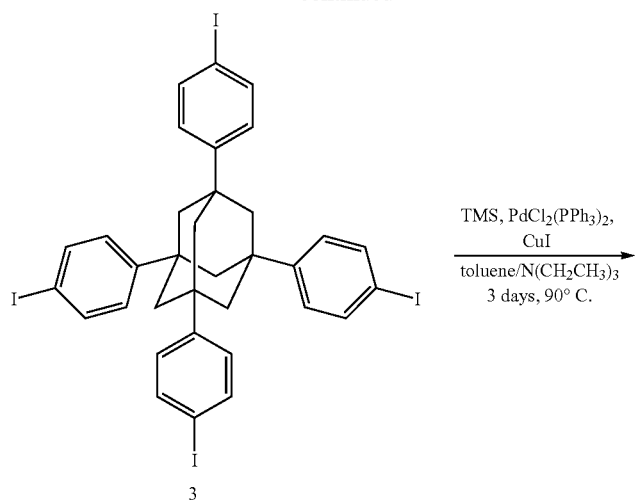
3
TMS, PdCl$_2$(PPh$_3$)$_2$, CuI
────────────────→
toluene/N(CH$_2$CH$_3$)$_3$
3 days, 90° C.
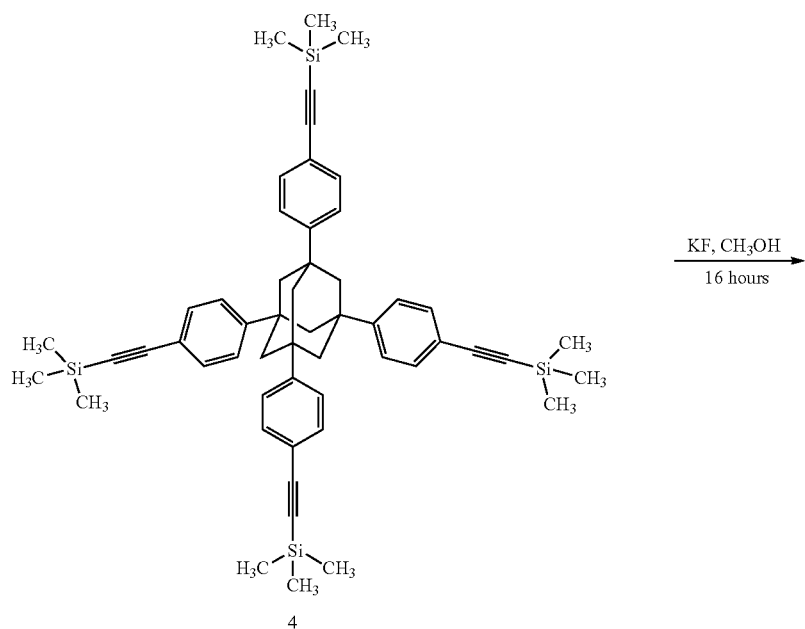
4
KF, CH$_3$OH
────────────→
16 hours

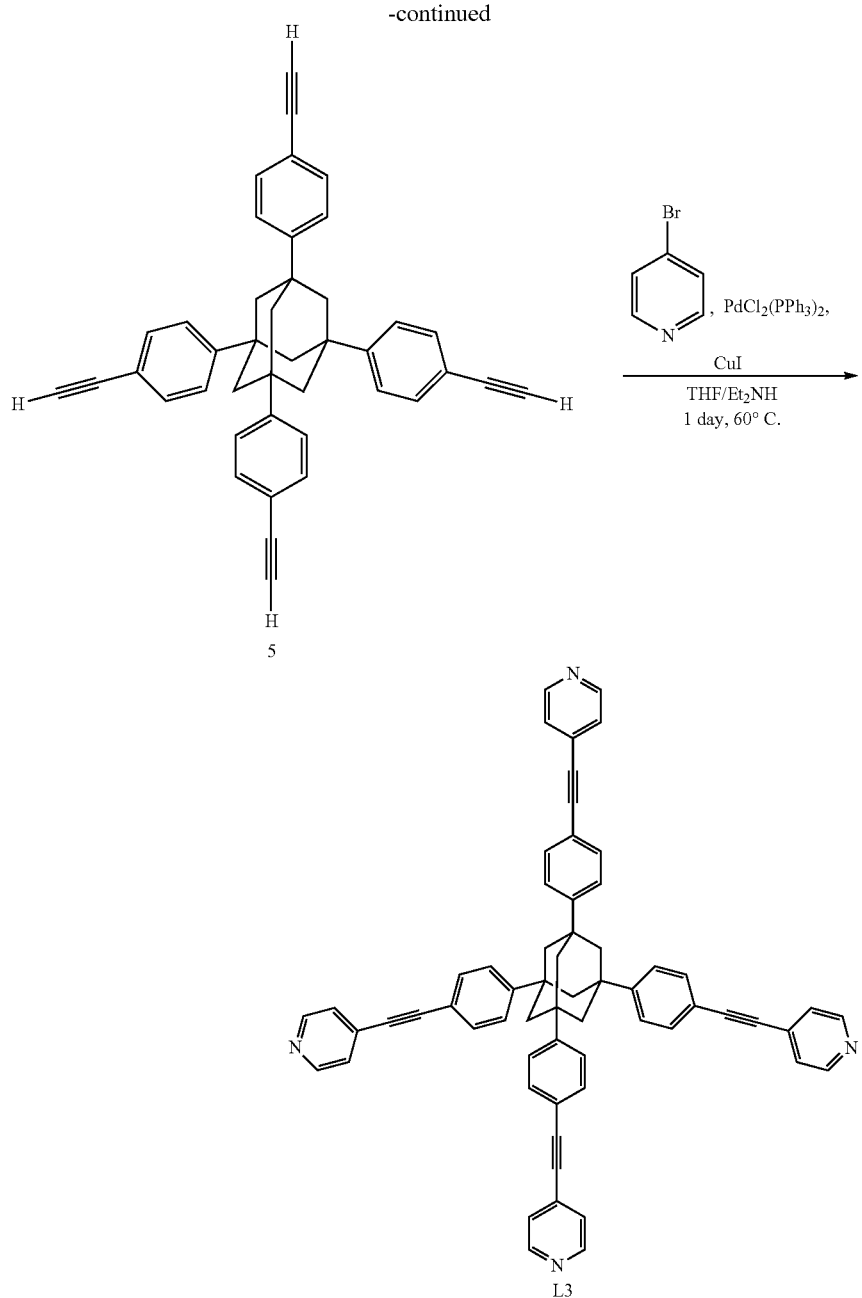

Each step of the synthesis is already reported in the literature and as shown in the scheme above. Thus, ligand L3 was made performing each step as described below.

Compound 2 was made by a Friedel-Crafts reaction of 1-bromoadamantane (Reichert et al., *Macromolecules* 1994, 27, 7015-7023) with tert-butyl bromide, $AlCl_3$, in benzene under reflux to yield compound 2. Compound 2 is allowed to react with $I_2$, [bis(trifluoroacetoxy)iodo]benzene (BIFB) in $CHCl_3$ at room temperature to yield compound 3 (*Org. Let.* 2002, 4, 3631-3634). Compound 3 is allowed to react with tetramethylsilane, $PdCl_2(PPh_3)_2$, CuI, toluene, triethylamine, for 3 days at 90° C. to obtain compound 4. (*Org. Biomol. Chem.* 2009, 7, 4734-4734). Compound 4 is allowed to react with KF in methanol for 16 hours to obtain compound 5. Compound 5 is allowed to react with 4-bromopyridine, $PdCl_2(PPh_3)_2$, CuI, in $THF/Et_2NH$, for 1 day at 60° C. to obtain ligand L3 (*Eur. J. Org. Chem.* 2011, 1743-1754).

Example 10

Synthesis of Ligand L4

Ligand L4 was prepared by the synthetic route shown in the scheme below. The synthesis started with 1-bromoadamantane undergoing a Friedel-Crafts reaction (Reichert et al., *Macromolecules* 1994, 27, 7015-7023) in a two step process. The first step reacted the 1-bromoadamantane with tert-butyl bromide, $AlCl_3$, in benzene under reflux. The second step reacted the product of step 1 with $I_2$, [bis(trifluoroacetoxy)iodo]benzene (BIFB) in $CHCl_3$ at room temperature. Step b reacted the tetraiodo intermediate with 4-vinylpyridine, triethylamine, PdCl$_2$(PPh$_3$)$_2$, NMP at 80° C. to obtain ligand L4. Crystals of L4 were obtained from chloroform and ether.

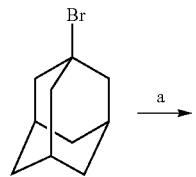

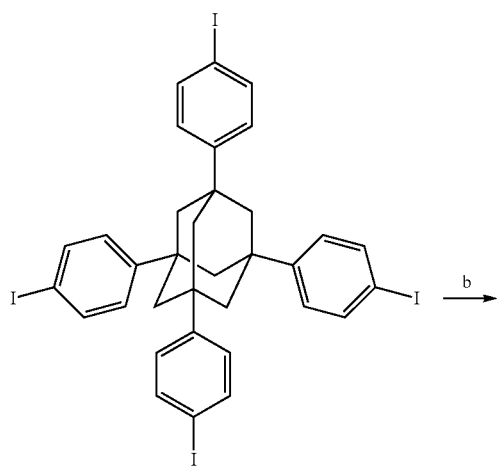

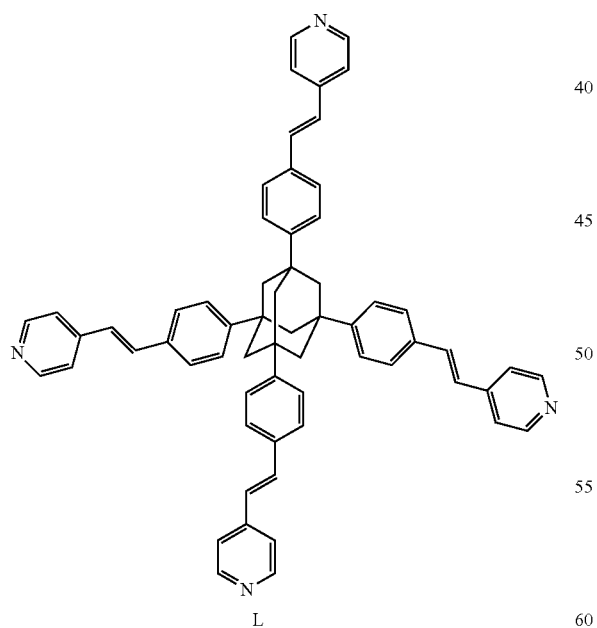

Crystals of L4 were grown from chloroform as the solvent and ether as the antisolvent. FIG. 71 illustrates the crystalline structure of L4. FIG. 71, panel A illustrates the distances between pyridine groups in Å that include 20.897 and 19.471. FIG. 71, panel B illustrates the adamantane core size in Å, where the distance between carbons is 3.537, 3.599, and 3.537. FIG. 71, panel C illustrates the angles of carbon bonds comprising the adamantane core.

Full single crystal XRD data are as follows. L4 has an empirical formula of C$_{62}$H$_{52}$N$_4$ and a formula weigh of 853.07 g. The crystal space group was tetragonal, P-4 with unit cell dimensions of a=13.6468(9) Å, α=90 deg.; b=13.6468(9) Å, β=90 deg.; and c=7.0913(4) Å, γ=90 deg. with a volume of 1320.65(19) Å$^3$.

Example 11

Synthesis of Ligand C

Ligand C was prepared by the synthetic route shown in the scheme below. The tetrakis(4-aminophenyl)methane (B) was prepared following the route set forth in Le Fur, et al., *Chem. Commun.*, 2003, 2966-2967. Tetrakis(4-aminophenyl)methane (B) (381 mg., 1 mmol) and 4-nitrosopyridine N-oxide D (Gowenlock, et al., *J. Chem. Res.* 1995, 358) (558 mg, 4.5 mmol) were dissolved in 8 ml of glacial acetic acid. The solution was heated to 80° C. for 14 hours and allowed cooled to room temperature. A precipitate formed and was collected by filtration, washed with NaHCO$_3$ solution and water to obtain an orange solid, Ligand C, in 55% yield. $^1$H NMR (300 MHz, CDCl$_3$) δ 8.29 (d, J=7.4 Hz, 8H), 7.90 (d, J=8.7 Hz, 8H), 7.83 (d, J=7.4 Hz, 8H), 7.53 (d, J=8.7 Hz, 8H).

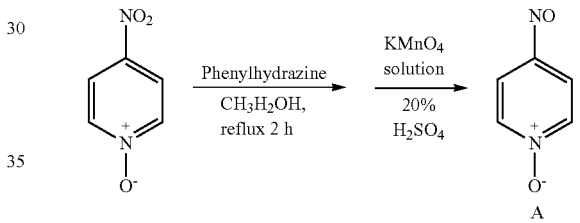

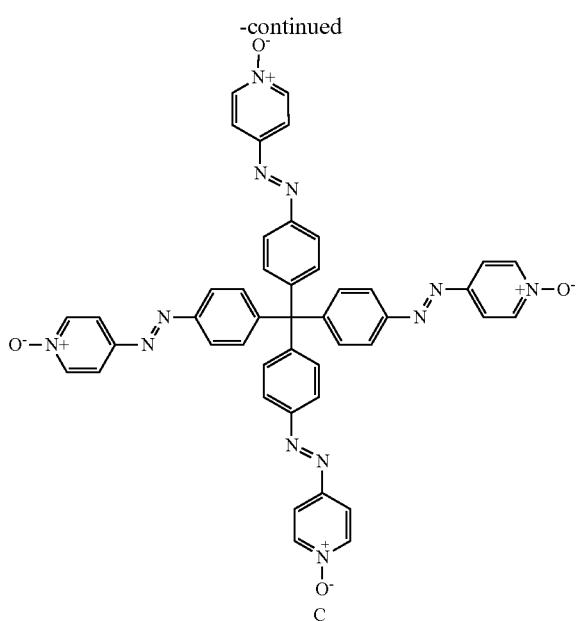

C

Example 12

Synthesis of Ligand E

Ligand E was prepared by the synthetic route shown in the scheme below. 4-Nitrosopyridine N-oxide (D) was prepared by the method set forth in Murashima et al., Inorg., Chem., 2012, 51, 4982. The tetrakis(4-aminophenyl)methane (B) was prepared as described in Example 11. Tetrakis(4-aminophenyl)methane (B) (381 mg., 1 mmol) and 4-nitrosopyridine N-oxide (D) (558 mg, 4.5 mmol) were dissolved in 8 ml of glacial acetic acid. The solution was heated to 80° C. for 14 hours and allowed cooled to room temperature. A precipitate formed and was collected by filtration, washed with NaHCO3 solution and water to get an orange solid, Ligand E.

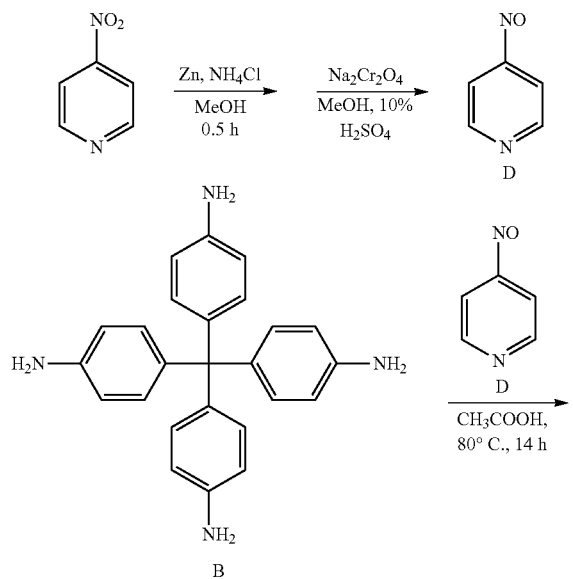

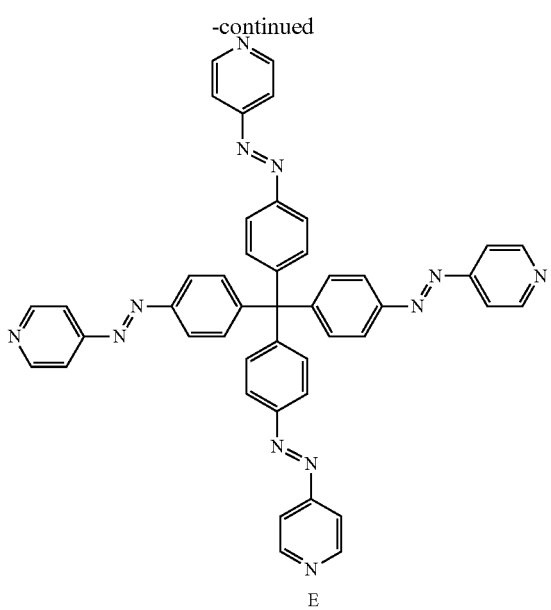

E

Example 13

Synthesis of L3-Cu(NO3)

A CHCl$_3$ solution of L3 (3 mg/ml) was prepared in a vial. Subsequently a double volume of DMF was added to the solution and sonicated for 1.5 hours. Cu(NO$_3$)$_2$·3H$_2$O was dissolved in DMF (concentration 7.1 mM). The reaction solution was prepared by transferring Cu(NO$_3$)$_2$·3H$_2$O (1 ml) and L3 (3 ml) to a pressure tube. The tube was sealed and heated for 2 days at 105° C. without stirring and with exclusion of light. Thereafter, the tube was cooled to room temperature over 9-10 hours in steps of 10° C./h. A light yellow/green precipitate appeared. The precipitate was left in the reaction solution, in the pressure tube, at room temperature and with light exclusion for 4 days.

After stopping the solvothermal reaction the precipitate was present as an elongated structure and roughly cylindrical structure. SEM images collected within 4 days detected relevant size and morphology variations for both typologies. FIG. 72, panels A-D illustrate SEM images of the solid structures at the end of the cooling process (FIG. 72, panel A), after 1 hour (FIG. 72, panel B), after 2 hours (FIG. 72, panel C), and after 4 days (FIG. 72, panel D).

The elongated structures changed depending upon aging time. The elongated structures had a rectangular cross-action (side dimension of about 700 nm and 400 nm) and a wide polydispersity in length (~10-40 µm, FIG. 73, panel A). The elongated structures often merged at the ends to form aggregates (FIG. 73, panel B). The aggregates were the building blocks of further structures at they lined up and joined each other forming cuboidal rods (FIG. 73, panel C). The cuboidal rods occurred at the end of the cooling process when partially formed rods (side size of the cross-action ~2-4 µm, length ~10 µm) were imaged (FIG. 73, panel D). The cuboidal rods were mostly complete after one day of cooling (FIG. 73, panel B, and FIG. 73, panel E). Some cuboidal rods were of a length of ~200 µm and some merged roughly radially. After further aging, the cuboidal rods shortened (FIG. 72, panel C and FIG. 73, panel F) to lengths of ~10 µm (FIG. 72, panel D, and FIG. 72, panel G).

Time dependent transformation of the cylindrical structures was observed. The structures were present in large numbers at the end of the cooling process. At the first stage, the shape structure approximated perfect cylindrical geometry, deviating by slightly narrowing at the center of the cylinder body (FIG. 74, panel A). Alternatively, the structure possessed irregular protrusions on a cylinder base (FIG. 74, panel B). In both structures, the cylinder had a base ~1.5 mm, and a height of 2 µm.

After one day the narrowing along the body cylinder defined two symmetric regions. On the two external faces a small ring close to the base center formed and lines extended radially from the center, similar to petals from a pistil (FIG. 74, panel C). The radial lines continued laterally onto the structure's thickness. The distance between the center of the internal ring and the external edges was ~4 µm. After further aging, the lines defined "petal-like" regions in the initial cylindrical shape and in some cases a shape resembling perfectly sculpted dual daisies with twelve petals that were symmetrically attached from the backside (FIG. 74, panels D and E). The petal-like shapes formed as structures free in solution (FIG. 74, panels C, D, and E) and attached to rod structures at different orientations (FIG. 75, panels B-F).

Example 14

Cuboidal Hollow MOFs and their Aggregates (L3/Cu(NO$_3$)$_2$ Ratio 1:4)

A CHCl$_3$ solution of L3 (3 mg/ml) was prepared in a vial. Subsequently a double volume of DMF was added to the solution and sonicated for 1 hour. Cu(NO$_3$)$_2$.3H$_2$O was dissolved in DMF (concentration 14.2 mM). The reaction solution was prepared by transferring Cu(NO$_3$)$_2$.3H$_2$O (1 ml) and L3 solution (3 ml) to a pressure tube. The tube was sealed and heated for 2 days at 105° C. without stirring and with exclusion of light. Thereafter, the tube was cooled to room temperature over 9-10 hours at a rate of 10° C./h. Upon cooling, a light yellow precipitate appeared.

Thereafter, the solution was transferred from the pressure tube to a vial and left at room temperature with exclusion of light. As the sample aged, the precipitate became larger and yellow in color.

SEM measurements showed elongated structures with circular cross sections having an internal radius of ~330 nm and 1.3 µm, and a rectangular cross-sections of ~674 and 361 nm. The elongated structures had a wide polydispersity in lengths (~5-20 µm) (FIG. 76, panels A and B). The circular cross sections were hollow (FIG. 76, panels C and D), whereas both hollow and solid morphologies were found in the rectangular cross action typology (FIG. 76, panel E).

When the solution and the precipitate underwent the same solvothermal reaction (as the prior solution), the solution and precipitate turned into a yellowish color and the system became monodisperse. The new structures formed a different elongated structure with cuboidal geometry (cuboidal structure=CS) (FIG. 77, panels A-D).

EDS measurements indicated the presence of copper in the cuboidal structures along with the elements constituting the ligand (carbon, nitrogen) and solvents (carbon, nitrogen, oxygen, chlorine) (FIG. 77, panel I). TEM diffraction patterns indicated crystallinity (FIG. 77, panel G), thereby, along with EDS, the CSs were identified as MOFs.

The CSs had defects, such as, undefined edges (FIG. 77, panels B, C, and D) and missing areas on the faces (FIG. 77, panel C). Phenomena of contact and penetration twin were evident (FIG. 77, panel C). SEM and high-angle annular dark-field imaging S-TEM (HAADF) measurements proved that CSs were hollow. Using the latter technique, a transversal scan of the structures was performed. The typical profile for the hollow structures indicated (i) was lower and flat in correspondence to the inner part of the CS and (ii) increased lateral edges (FIG. 77, panel E). The triangular shape of the profile extremities suggested a non-uniform density of the CS walls. High-magnification TEM micrographs were collected, which revealed brighter and lined contrast at the longitudinal edges and layers with different length and irregular fringes at the ends (FIG. 77, panel H). Layers that confer a stepwise profile to the ends were also visible by SEM (FIG. 77, panel H, bottom right side).

It is believed that in schematized CS each face of the cuboids were formed by groups of laminae joined perpendicularly at the edges (FIG. 77, panel H). The presence of spikes at the ends (FIG. 77, panels B, D, and H bottom right side) indicates a longitudinal growth front following the plane direction that progresses separately for each plane within a layer FIG. 77, panel F). The laminae on the same face grew independently, thereby resulting in layers of different length as indicated by TEM images and STEM scansion. The latter had wall high-angle annular dark-field imaging.

CSs were left in the reaction solution at room temperature with light exclusion and SEM images were collected daily. SEM images indicated a numerical decrease in CSs (FIG. 78, panels A-F). Graphical and statistical representations of this numerical decrease as a function of aging time are found in FIG. 78, panels G and H.

As the number of CSs decreased, new structures appeared, hierarchical aggregates (HAs) that were elongated cuboidal units arranged in different directions as 3D objects. (FIG. 79, panel A-F). When several elongated cuboidal units were present, the units were disposed radially from a common central region yielding a "hedgehog-like" structure (FIG. 79, panel C). As the sample aged, the number of elongated units increased in the HA. After ageing 5 days, the elongated units were disposed in one hemisphere of the circumscribed sphere (FIG. 79, panels A and B). By the 10$^{th}$ day, the HA became symmetrical (FIG. 79, panel C). After 12 days of ageing, the HAs' symmetry was fully developed as a high number of the space directions were covered by the unit disposition (FIG. 79, panel D). By the 15$^{th}$ (FIG. 79, panel E) and 20$^{th}$ day (FIG. 79, panel F) deteriorated when elongated cuboidal units overlapped and differed in length.

The external cross-section of the elongated units of the HA remained unchanged during the aging process, in contrast the length continued to increase. (FIG. 78, panel H). As the length increased, the variation of the end morphology increased. HAs were hollow units open at one extremity characterized by an uneven length at the end "spike-type" profile (FIG. 79, panel G). Thereafter with continued aging, the ends of the CS diminished (FIG. 79, panel H) and after 12 days, the ends were evenly matched (FIG. 79, panel I). After further aging, the ends sealed closure (FIG. 79, panel L). SEM measurements on cut structures proved that cavities were still present along the elongated units (FIG. 80, panel A).

Once the end closed, non-symmetrical growth occurred on the sealed end as the elongation of the cuboid faces, which formed spikes (FIG. 79, panel M).

Shape similarity between HA units and CS without evidence of dissolution and recrystallization, suggested that HAs were formed by the assembly of the starting CS MOFs. SEM images illustrated the ongoing process where elongation units merged, for instance the coupling of two CS units at the midpoint (FIG. 80, panel A). The CS coupling was partial (FIG. 80, panel B) or with several CS units (FIG. 80, panels C and D).

Example 15

Rose-Like MOFs (L3/Cu(NO$_3$)$_2$ Ratio=1:6)

Preparation: a CHCl$_3$ solution of the ligand (3 mg/ml) was prepared in a vial. Subsequently a double volume of DMF was added to the solution and sonicated for 1.5 hours.

Cu(NO$_3$)$_2$.3H$_2$O was dissolved in DMF (concentration 21.3 mM). The reaction solution was prepared by transferring 1 ml and 3 ml of the Cu(NO$_3$)$_2$.3H$_2$O and ligand solution respectively from the vials to a pressure tube. Then, the tube was sealed and heated for 2 days at 105° C. without stirring and with exclusion of light. Lastly, it was cooled to room temperature over 9-10 hours in steps of 10° C./h. This resulted in a green precipitate and in the structures reported in FIG. 81, panel A and panel B.

APPENDIX

Scheme 1: Chemical structures of the polypyridyl ligands L1-L4

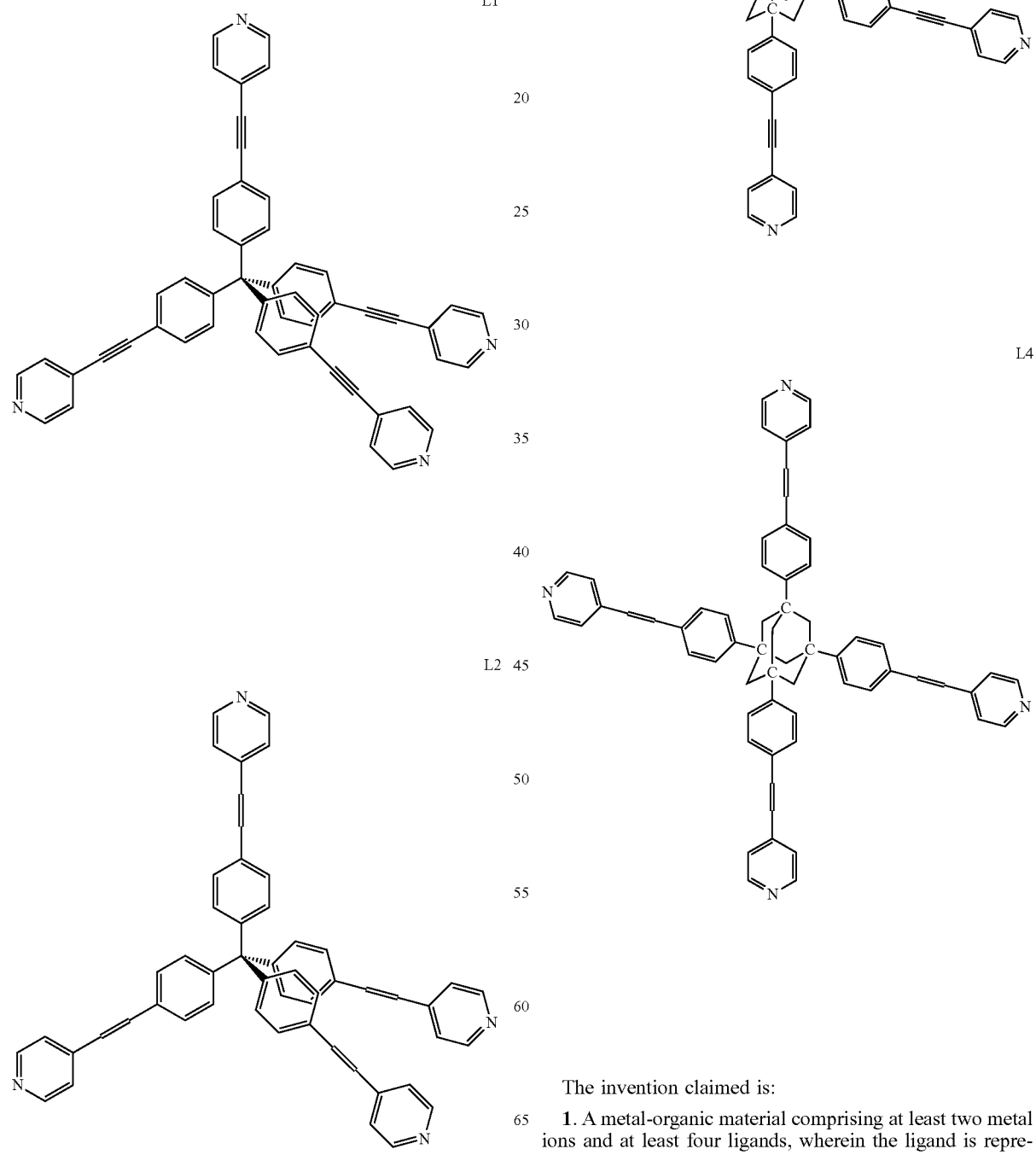

The invention claimed is:

1. A metal-organic material comprising at least two metal ions and at least four ligands, wherein the ligand is represented by formula L4

L4

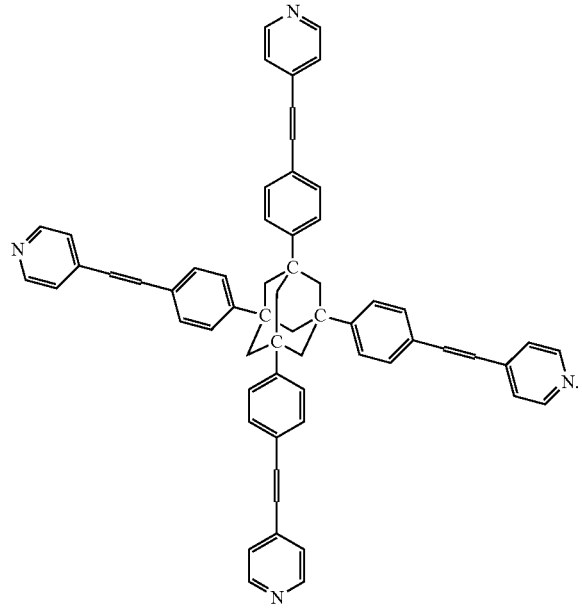

L3

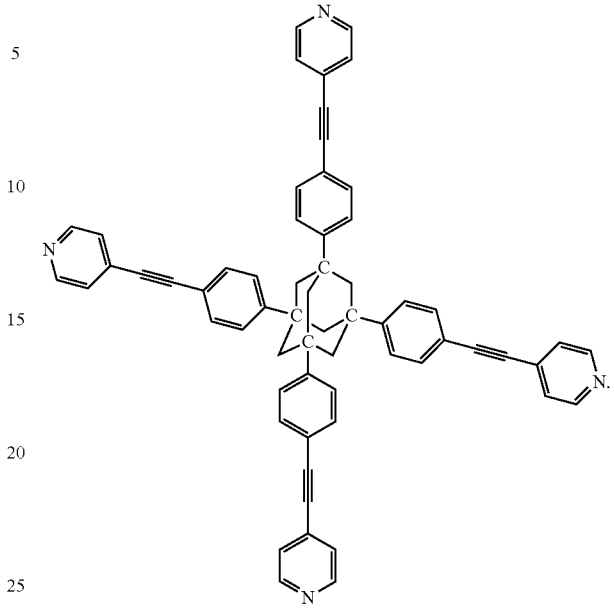

2. The metal-organic material according to claim 1, wherein the metal ion is $Ni^{2+}$ or $Cu^{2+}$ and is present as a salt.

3. The metal-organic material according to claim 1, wherein the metal to ligand ratio is 1:2 to 1:10.

4. The metal-organic material according to claim 1, wherein the metal to ligand ratio is 1:2 to 1:4.

5. The metal-organic material according to claim 1, wherein the metal ion is present as a salt of NiBr, $NiNO_3$, or $CuNO_3$.

6. The metal-organic material according to claim 1, wherein the material is crystalline.

7. The metal-organic material according to claim 6, wherein the crystalline material is in the shape of an egg, barrel, or hexagonal prism.

8. The metal-organic material according to claim 1, wherein the material is coated with Au nanoparticles.

9. The metal-organic material according to claim 1, wherein metal ions are $Ni^{2+}$ and $Cu^{2+}$ in a ratio of 1:1.

10. The metal-organic material according to claim 1, wherein the metal ions are present as NiBr and $NiNO_3$ in a 1:1 ratio.

11. A metal-organic material comprising at least two metal ions and at least four ligands, wherein the ligand is represented by formula L3

12. The metal-organic material according to claim 11, wherein the metal ion is $Ni^{2+}$ or $Cu^{2+}$ and is present as a salt.

13. The metal-organic material according to claim 11, wherein the metal to ligand ratio is 1:2 to 1:10.

14. The metal-organic material according to claim 11, wherein the metal to ligand ratio is 1:2 to 1:4.

15. The metal-organic material according to claim 11, wherein the metal ion is present as a salt of $NiBr_2$, $Ni(NO_3)_2$, or $Cu(NO_3)_2$.

16. The metal-organic material according to claim 11, wherein the material is crystalline.

17. The metal-organic material according to claim 16, wherein the crystalline material has a rectangular cross-section.

18. The metal-organic material according to claim 17, wherein the rectangular cross section is from about 400 nm to about 700 nm.

19. The metal-organic material according to claim 16, wherein crystalline material is cylinder shaped.

20. The metal-organic material according to claim 17, wherein the rectangular cross section is from about 674 nm to about 361 nm.

21. The metal-organic material according to claim 16, wherein the crystalline material is in an elongated cuboidal shape.

22. A compound of formula L3, formula L4, formula C, or formula E:

L4
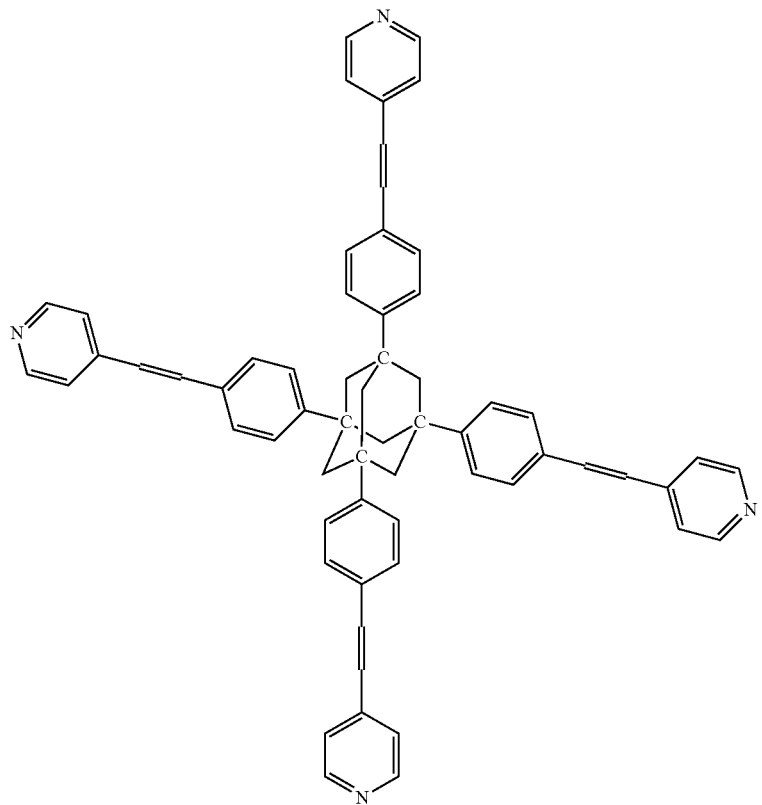
L3
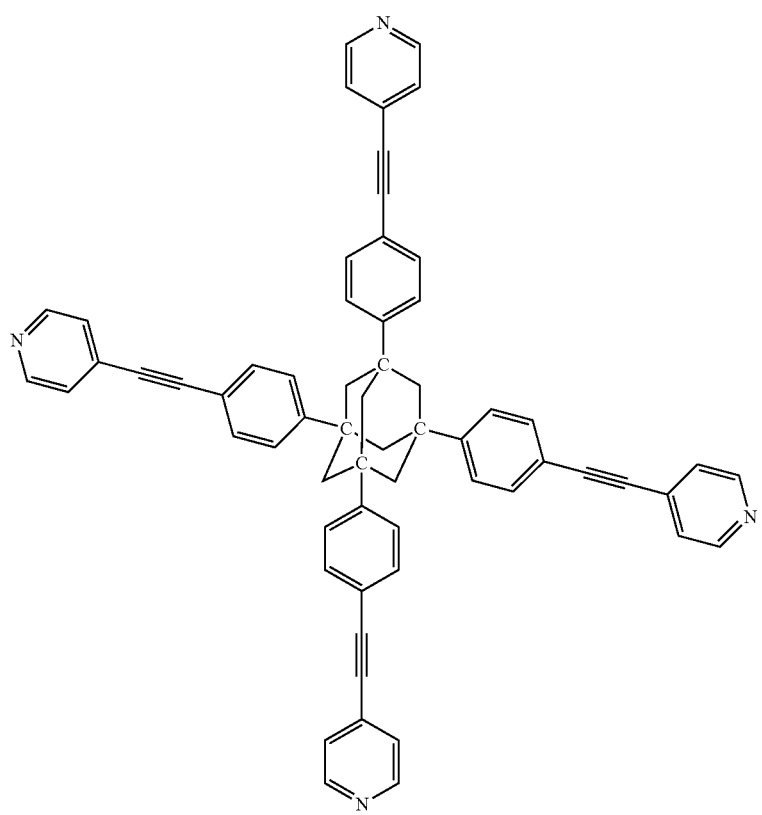

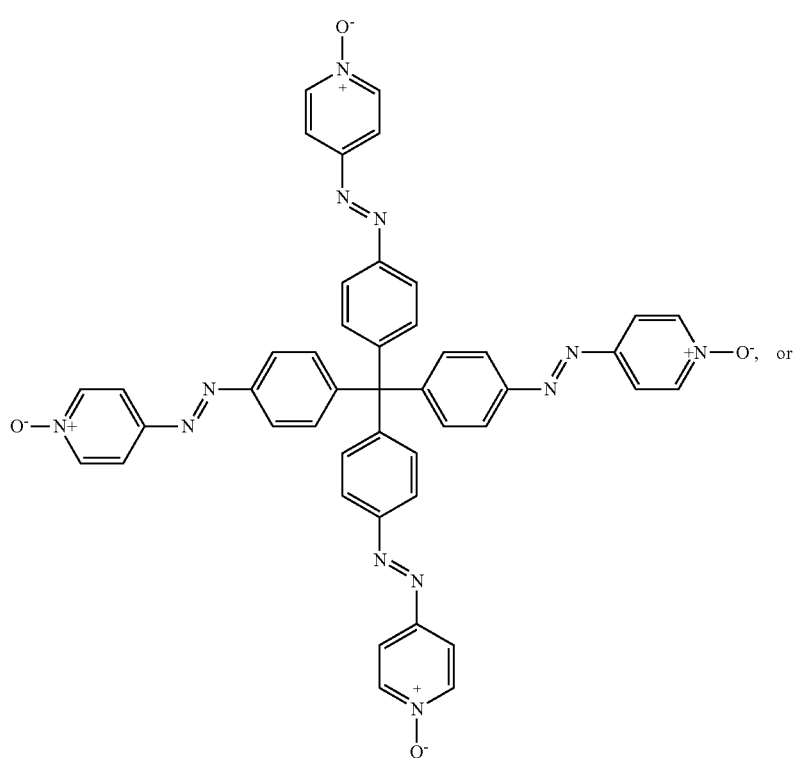
Formula C
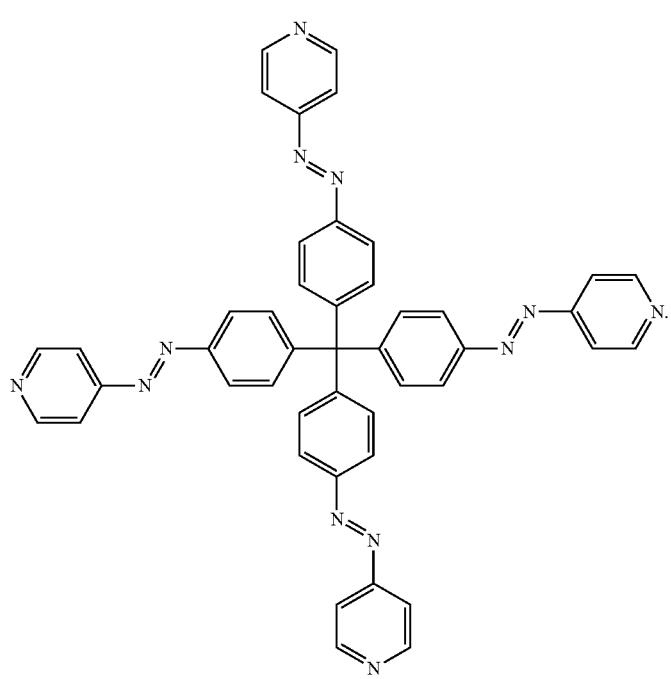
Formula E
23. The compound according to claim 22, wherein the compound is in crystalline form.
24. The compound according to claim 23, wherein the distance between the nitrogen atoms of the pyridine ring is about 20.89 Å or 19.47 Å.
* * * * *